US012780837B2

(12) United States Patent
Park et al.

(10) Patent No.: US 12,780,837 B2
(45) Date of Patent: Nov. 3, 2026

(54) PYRIMIDODIAZEPINE DERIVATIVES OR USES THEREOF

(71) Applicant: SPARK BIOPHARMA, INC., Seoul (KR)

(72) Inventors: Seung Bum Park, Seoul (KR); Young Hee Shin, Seoul (KR)

(73) Assignee: SPARK BIOPHARMA, INC., Seoul (KR)

( * ) Notice: Subject to any disclaimer, the term of this patent is extended or adjusted under 35 U.S.C. 154(b) by 606 days.

(21) Appl. No.: 18/025,481

(22) PCT Filed: Aug. 31, 2021

(86) PCT No.: PCT/KR2021/011710

§ 371 (c)(1),
(2) Date: Mar. 9, 2023

(87) PCT Pub. No.: WO2022/055168

PCT Pub. Date: Mar. 17, 2022

(65) Prior Publication Data

US 2023/0322805 A1 Oct. 12, 2023

(30) Foreign Application Priority Data

Sep. 9, 2020 (KR) ........................ 10-2020-0115104

(51) Int. Cl.
*C07D 498/18* (2006.01)
*A61P 25/28* (2006.01)
(Continued)

(52) U.S. Cl.
CPC ............ *C07D 498/18* (2013.01); *A61P 25/28* (2018.01); *C07D 487/04* (2013.01); *C07D 513/18* (2013.01)

(58) Field of Classification Search
CPC .. A61K 31/551; A61K 31/553; A61K 31/554; C07D 487/04; C07D 487/18; C07D 498/18; C07D 513/18; A61P 25/28
See application file for complete search history.

(56) References Cited

FOREIGN PATENT DOCUMENTS

| | | |
|---|---|---|
| KR | 10-2012-0093940 A | 8/2012 |
| WO | WO-2010/053825 A1 | 5/2010 |

(Continued)

OTHER PUBLICATIONS

Shin et al., Phenotypic Discovery of Neuroprotective Agents by Regulation of Tau Proteostasis via Stress-Responsive Activation of PERK Signaling, Angewandte Chemie, vol. 60, 1831-1838, Nov. 18, 2020, with supplemental information (Year: 2020).*

(Continued)

*Primary Examiner* — Sarah Pihonak
*Assistant Examiner* — Padmaja S Rao
(74) *Attorney, Agent, or Firm* — Harness, Dickey & Pierce, P.L.C.

(57) ABSTRACT

The present invention relates to a pyrimidodiazepine derivative or a pharmaceutically acceptable salt thereof and a use thereof. A pyrimidodiazepine derivative or a pharmaceutically acceptable salt thereof according to the present invention can bind specifically to DNAJC3 and PDIA3, which are inhibitory of PERK signaling activation, to prevent the inhibition against PERK signaling. Thus, having an advantage of effectively suppressing or inhibiting tau aggregation, the pyrimidodiazepine derivative or a pharmaceutically acceptable salt thereof can not only be used in a pharmaceutical composition capable of fundamentally preventing or treating tauopathies associated with the activation of tau protein, but also can find applications in various studies on (Continued)

the development of therapeutic agents for tauopathies, and the expression or activity inhibition of tau protein.

15 Claims, 31 Drawing Sheets

Specification includes a Sequence Listing.

(51) Int. Cl.
*C07D 487/04* (2006.01)
*C07D 513/18* (2006.01)

(56) References Cited

FOREIGN PATENT DOCUMENTS

WO WO-2010/132015 A1 11/2010
WO WO-2018062732 A1 * 4/2018 ........... C07D 487/04

OTHER PUBLICATIONS

International Search Report from corresponding PCT Application No. PCT/KR2021/011710, dated Dec. 23, 2021.
Kim, J. et al. Diversity-oriented synthetic strategy for developing a chemical modulator of protein-protein interaction. Nature Communications. 2016, vol. 7, pp. 1-10.
Shin, Y.-H. et al. Phenotypic discovery of neuroprotective agents by regulation of Tau proteostasis via stress-responsive activation of PERK signaling. Angewandte Chemie. Nov. 18, 2020, vol. 60, pp. 1831-1838.
Office Action from corresponding European Patent Application No. 22865008.1, dated Oct. 1, 2025.
Zhang, C. X., et al.; "STING signaling remodels the tumor microenvironment by antagonizing myeloid-derived suppressor cell expansion", Cell Death & Differentiation, 2019, 26; 2314-2328.

* cited by examiner

PYRIMIDODIAZEPINE DERIVATIVES OR USES THEREOF

CROSS-REFERENCE TO RELATED APPLICATIONS

This application is a national phase application of PCT Application No. PCT/KR2021/011710, filed on Aug. 31, 2021, which claims benefit of Korean Patent Application No. 10-2020-0115104, filed on Sep. 9, 2020. The entire disclosures of the applications identified in this paragraph are incorporated herein by references.

SEQUENCE LISTING

This application contains references to amino acid sequences and/or nucleic acid sequences which have been submitted concurrently herewith as the sequence listing TXT file entitled "000093usnp_SequenceListing_ST25", file size 1,836 bytes, created on 5 Aug. 2026. The aforementioned sequence listing is hereby incorporated by reference in its entirety pursuant to 37 C.F.R. § 1.52 (e) (5).

TECHNICAL FIELD

The present invention relates to novel pyrimidodiazepine derivatives and uses thereof, and more particularly, to pyrimidodiazepine derivatives acting on the PERK signaling pathway, and pharmaceutical compositions for preventing or treating tauopathy comprising the same.

BACKGROUND ART

Entering the 21st century, human lifespan has become longer, the incidence of neurodegenerative diseases has increased accordingly, and social costs for this are increasing exponentially, but drugs that have been verified as treatments for neurodegenerative diseases are extremely limited, and their effects can also be seen as insignificant.

On the other hand, diseases characterized by the accumulation of misfolded proteins are called proteinopathies. One of the hallmarks of many neurodegenerative diseases is the accumulation of secondary abnormal protein aggregates resulting from inefficient protein quality control (PQC) processes. One of the best known protein disorders is Alzheimer's disease (AD). Various proteins, including tau protein and amyloid β(Aβ), have been pointed out as the cause of Alzheimer's disease. Among them, both tau protein and amyloid β are proteins present in brain neurons. Tau protein appears inside the cell and amyloid β appears on the surface of the cell. It is known that when tau protein and amyloid β are misfolded, these proteins aggregate with each other to form plaques, and neurofibrillary tangles (NFT), in which tau protein tangles with each other, occur, destroying nerve cells.

NFT symptoms are observed not only in Alzheimer's disease but also in other diseases including frontotemporal dementia (FTD), progressive supranuclear palsy and traumatic brain injury (TBI). These are collectively referred to as tauopathies. The main treatments for tauopathy include the use of tau immunotherapy, modulators of tau post-translational modifications, inhibitors of tau aggregation, and enhancers of protein clearance mechanisms that promote tau degradation.

Several tau-targeted immunotherapy drugs are currently being evaluated in clinical trials, but are still in the early stages of development, and there is still no approved therapeutic or prophylactic agent for tauopathy, mostly due to limited knowledge of the pathologically associated mechanisms of tau protein in tauopathy.

Endoplasmic reticulum (ER) stress is known to be involved in neurodegenerative disorders including tauopathies. The endoplasmic reticulum is a structure that uses various chaperones to ensure that initially misfolded proteins are correctly folded before transport through secretory vesicles. Stress stimuli to the ER caused by accumulation of misfolded proteins and changes in intracellular calcium levels activate an adaptive signaling pathway for cell survival known as the unfolded protein response (UPR). This process resets ER homeostasis by temporarily reducing protein synthesis and activating protein clearance pathways. When ER stress becomes chronic, the UPR triggers apoptosis to eliminate irreversibly damaged cells. Various ER stress markers or UPR proteins were found along with accumulated NFTs in post-mortem brain tissues of patients with tauopathy, and a relationship was observed between the degree of protein aggregation and the disease state. Although tauopathy has been reported to be exacerbated by chronic ER stress, development of tauopathy therapeutics targeting ER stress is insignificant.

PRIOR ART LITERATURE

Republic of Korea Patent Publication No. 10-2019-7012934

DISCLOSURE OF INVENTION

Technical Problem

The present inventors synthesized a compound capable of inhibiting tau aggregation by acting on the PERK signaling pathway, and based on this, the present invention was completed. Accordingly, an object of the present invention is to provide a novel compound having tau aggregation inhibitory activity.

In addition, another object of the present invention is to provide a pharmaceutical composition for preventing or treating tauopathy comprising the novel compound as an active ingredient.

However, the technical problem to be achieved by the present invention is not limited to the above-mentioned problems, and other problems not mentioned will be clearly understood by those skilled in the art from the following description.

Solution to Problem

In order to achieve the above object, in one aspect, the present invention provides a compound represented by the following Formula 1, or a pharmaceutically acceptable salt thereof:

[Formula 1]

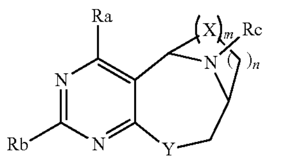

wherein

X is $CH_2$; CO; $COCF_3$; NH; $NCH_3$; O; S; or $SO_2$;

Y is O; S; SO; $SO_2$; or NRy;

m is an integer of 0 or 1;

n is an integer of 0, 1 or 2;

Ry is hydrogen; $C_1$-$C_{20}$ linear or branched alkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; —COR'; —$SO_2$R'; —SOR'; —COOR'; —CONHR'; or —CONR'R";

Ra is hydrogen; $C_1$-$C_{20}$ linear or branched alkyl; $C_1$-$C_{20}$ linear or branched alkenyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; 5- to 6-membered heterocyclyl containing 1 to 2 N atoms in which any one or more hydrogens are substituted with $C_1$-$C_5$ linear or branched alkyl, or 6- to 10-membered aryl; or —$NRa_1Ra_2$;

Rb is hydrogen; $C_1$-$C_{20}$ linear or branched alkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; —NR'R"; —SR'; —$SO_2$R'; or —SOR';

Rc is hydrogen; $C_1$-$C_{20}$ linear or branched alkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; —COR'; —SOR'; —$SO_2$R'; —COOR'; —CONHR'; or —CONR'R";

$Ra_1$ and $Ra_2$ of —$NRa_1Ra_2$ in the definition of Ra are each independently hydrogen; $C_1$-$C_{20}$ linear or branched alkyl; $C_1$-$C_{10}$ linear or branched aminoalkyl in which at least one hydrogen is substituted with an amine; arylalkyl in which any one hydrogen of $C_1$-$C_{10}$ linear or branched alkyl is substituted with $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; heteroarylalkyl in which any one hydrogen of $C_1$-$C_5$ alkyl is substituted with 6-membered heteroaryl containing one N; phenoxyalkyl in which any one hydrogen of $C_1$-$C_{10}$ linear or branched alkyl is substituted with a phenoxy group; $C_6$-$C_{20}$ aryl unsubstituted or substituted with one or more selected from the group consisting of $C_1$-$C_{10}$ linear or branched alkoxy and azide; —COR'; —$SO_2$R'; —SOR'; —COR'R"; or —COOR'; and R' and R" in the definitions of Ry, Rb, Rc, $Ra_1$ and $Ra_2$ are each independently hydrogen; $C_1$-$C_{10}$ linear or branched alkyl; $C_3$-$C_{10}$ cycloalkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkynyl, $C_1$-$C_{10}$ linear or branched alkoxy, and nitro; benzyl; 5- to 20-membered heteroaryl containing 1 to 3 heteroatoms selected from N, O and S.

In addition, the present invention provides a tau aggregation inhibitor comprising the compound represented by the Formula 1, or a pharmaceutically acceptable salt thereof, which inhibits tau aggregation by preventing inhibition of PERK signal transduction through binding with PDIA3, DNAJC3, or both.

In addition, the present invention provides a pharmaceutical composition for preventing or treating tauopathies, comprising the compound represented by Formula 1 or a pharmaceutically acceptable salt thereof.

In addition, the present invention provides a method for preventing or treating tauopathies, comprising administering to a subject in need thereof the compound represented by Formula 1 or a pharmaceutically acceptable salt thereof.

In addition, the present invention provides a use of the compound represented by Formula 1 or a pharmaceutically acceptable salt thereof for preventing or treating tauopathies in a subject.

Advantageous Effects of Invention

The pyrimidodiazepine derivative or a pharmaceutically acceptable salt thereof according to the present invention can specifically bind to DNAJC3 and PDIA3, which inhibit PERK signal activation, thereby preventing PERK signal inhibition, thereby effectively inhibiting or inhibiting tau aggregation. Therefore, it can be used as a pharmaceutical composition that can fundamentally prevent or treat tauopathy associated with activation of tau protein, as well as it can be used in various studies on the development of agents for the treatment of tauopathy and inhibition of expression or activity of tau protein.

MODE FOR THE INVENTION

Figure 3:
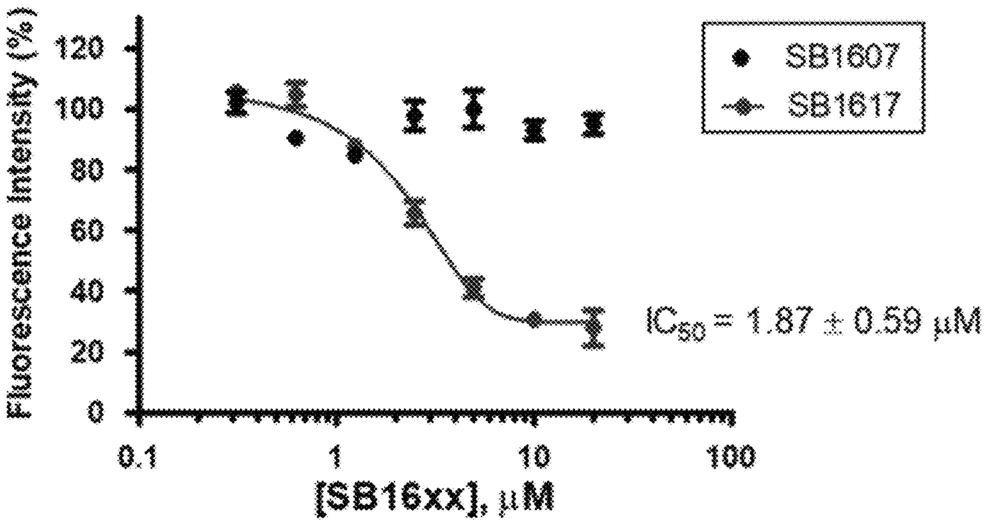

FIG. 3 graphically depicts dose-dependent data on the change in Venus fluorescence intensity when BiFC-tau Venus HEK293 cells were co-treated with various concentrations of SB1617 or SB1607 and 80 nM thapsigargin for 20 hours.

Figure 4:
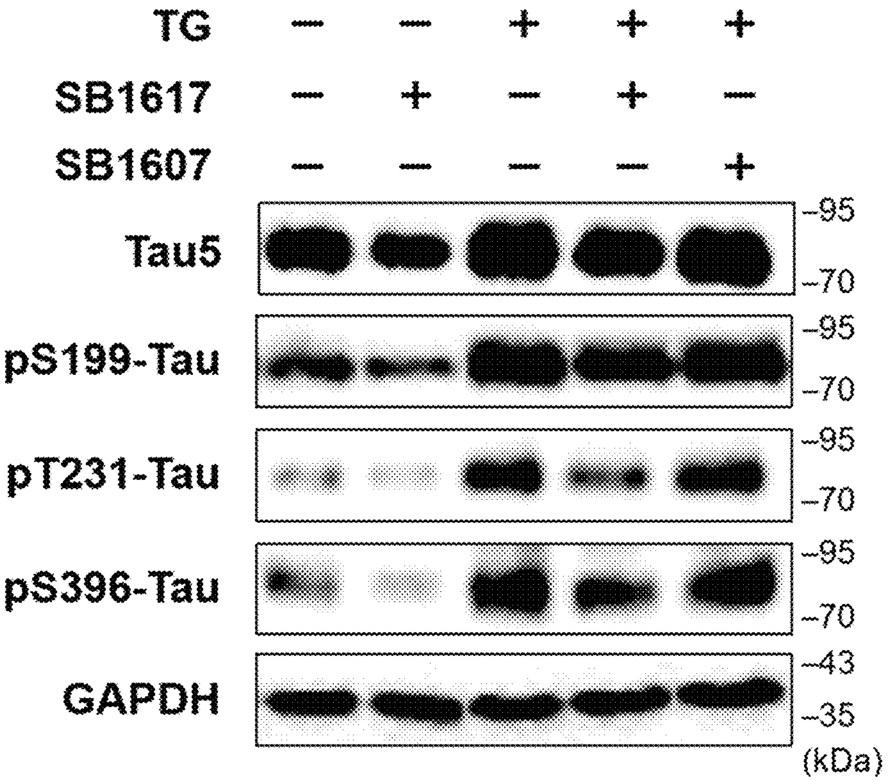

FIG. 4 shows the results of immunoblot analysis measuring total tau (Tau5) and phospho-tau (S199, T231) levels when SB1617, SB1607, and 80 nM thapsigargin were treated in BiFC-tau Venus HEK293 cells for 20 hours.

Figure 5:
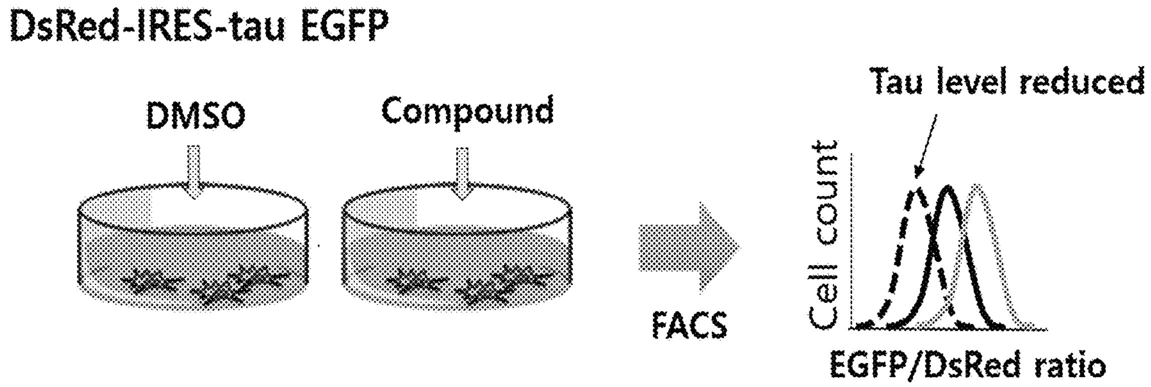

FIG. 5 shows an example of an IRES integrated cell system for measuring tau proteolysis according to the present invention.

Figure 6:
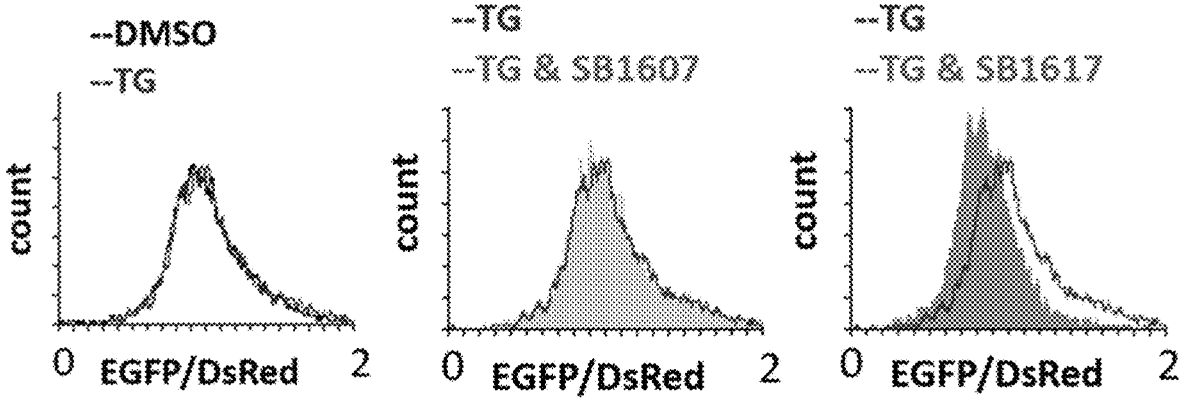

FIG. 6 shows flow cytometry data measured in DsRed-IRES-tau EGFP HEK293 cells treated with 100 nM TG together with 5 μM SB1617 or SB1607 for 20 hours.

Figure 7:
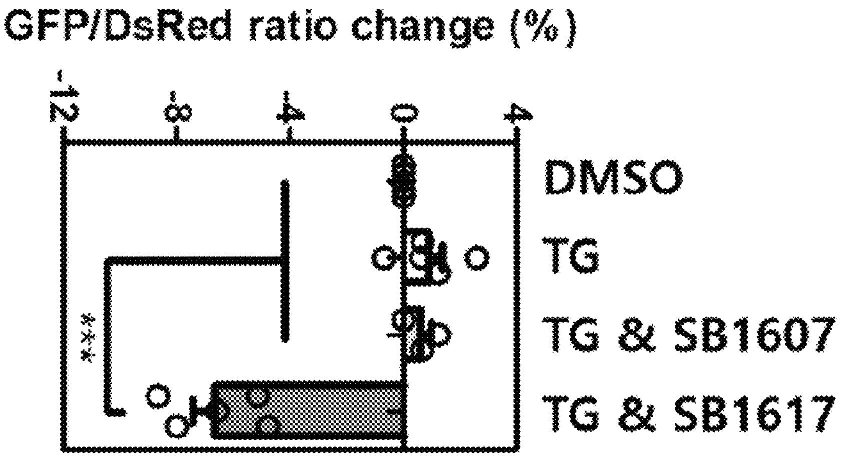

FIG. 7 shows the result of comparing the EGFP-to-DsRed signal ratio through one-way analysis of variance (ANOVA) using Bonferroni's post hoc analysis.

Figure 8:
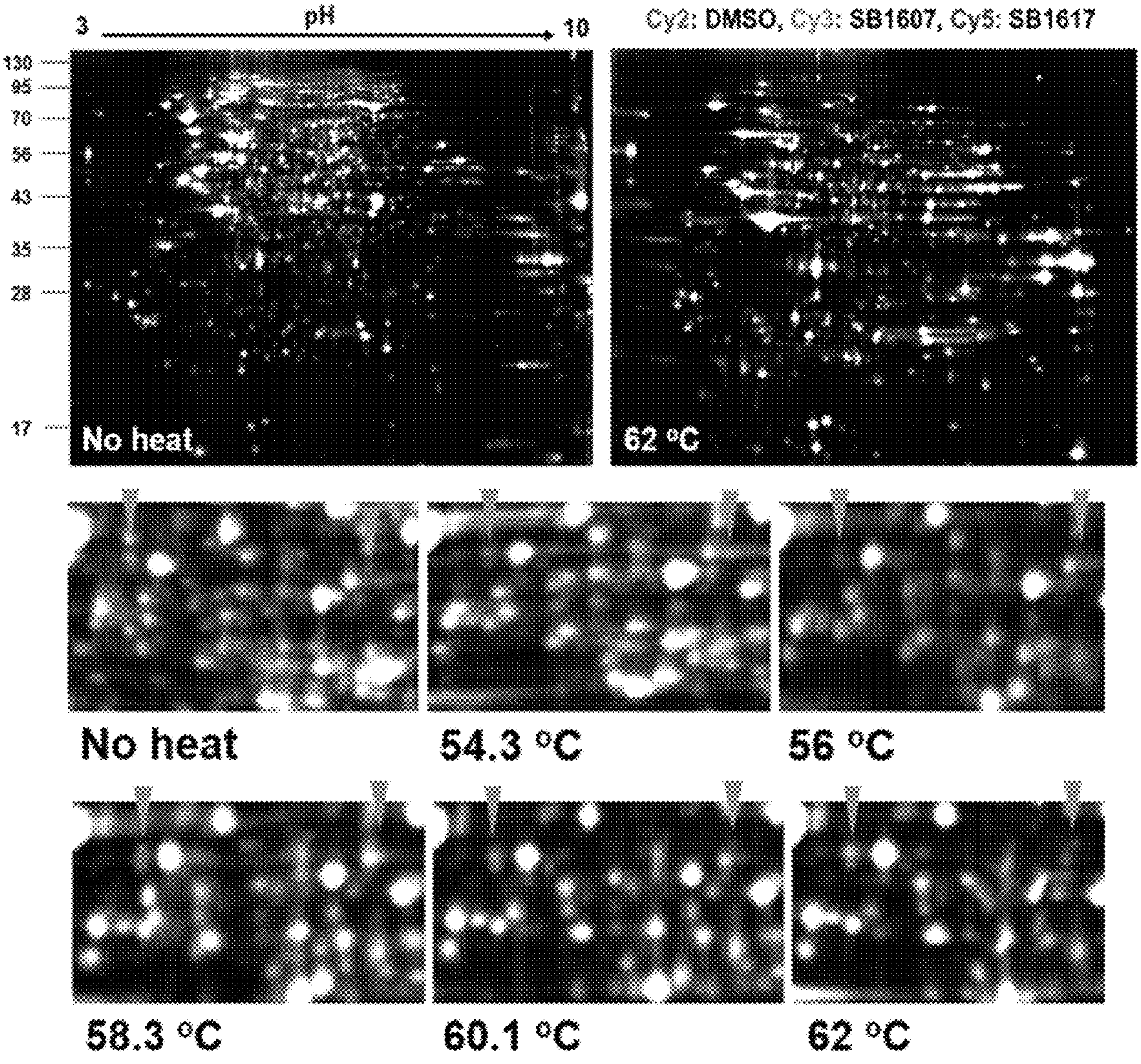

FIG. 8 shows an analysis image using TS-FITGE 2D gel electrophoresis.

Figure 9:
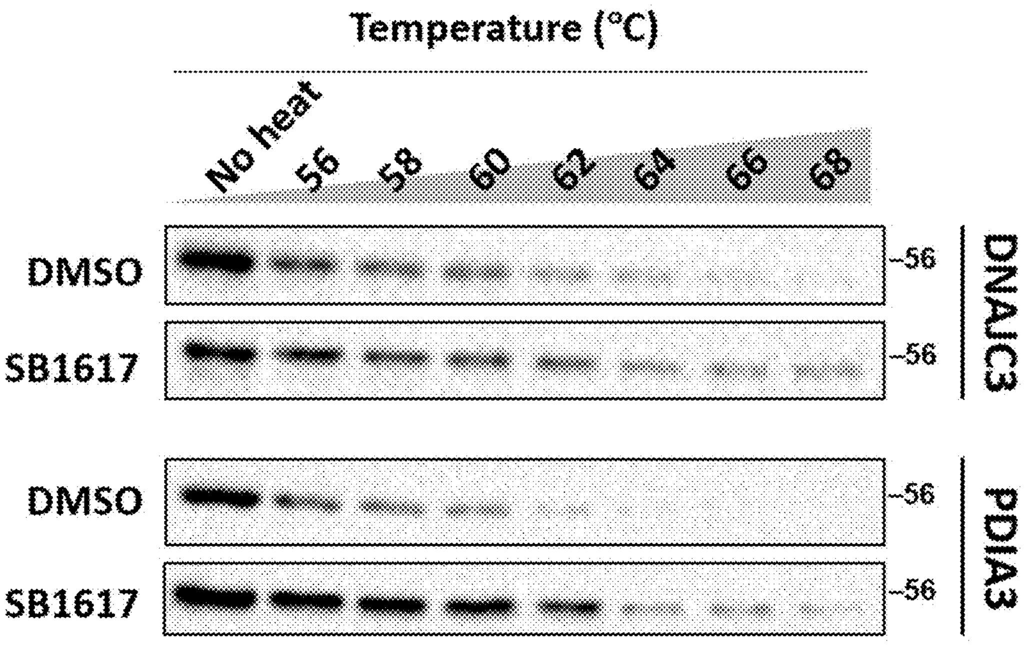

FIG. 9 shows the results of CETSA analysis confirming the specific binding of the pyrimidodiazepine derivatives according to the present invention to DNAJC3 and PDIA3.

Figure 10:
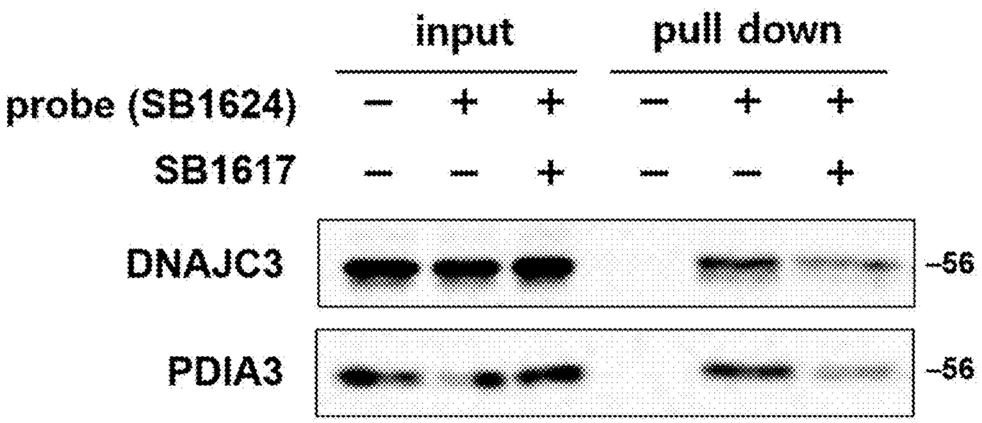

FIG. 10 shows the results of pull-down analysis by SB1624, a light-responsive probe for DNAJC3 and PDIA3.

Figure 11:
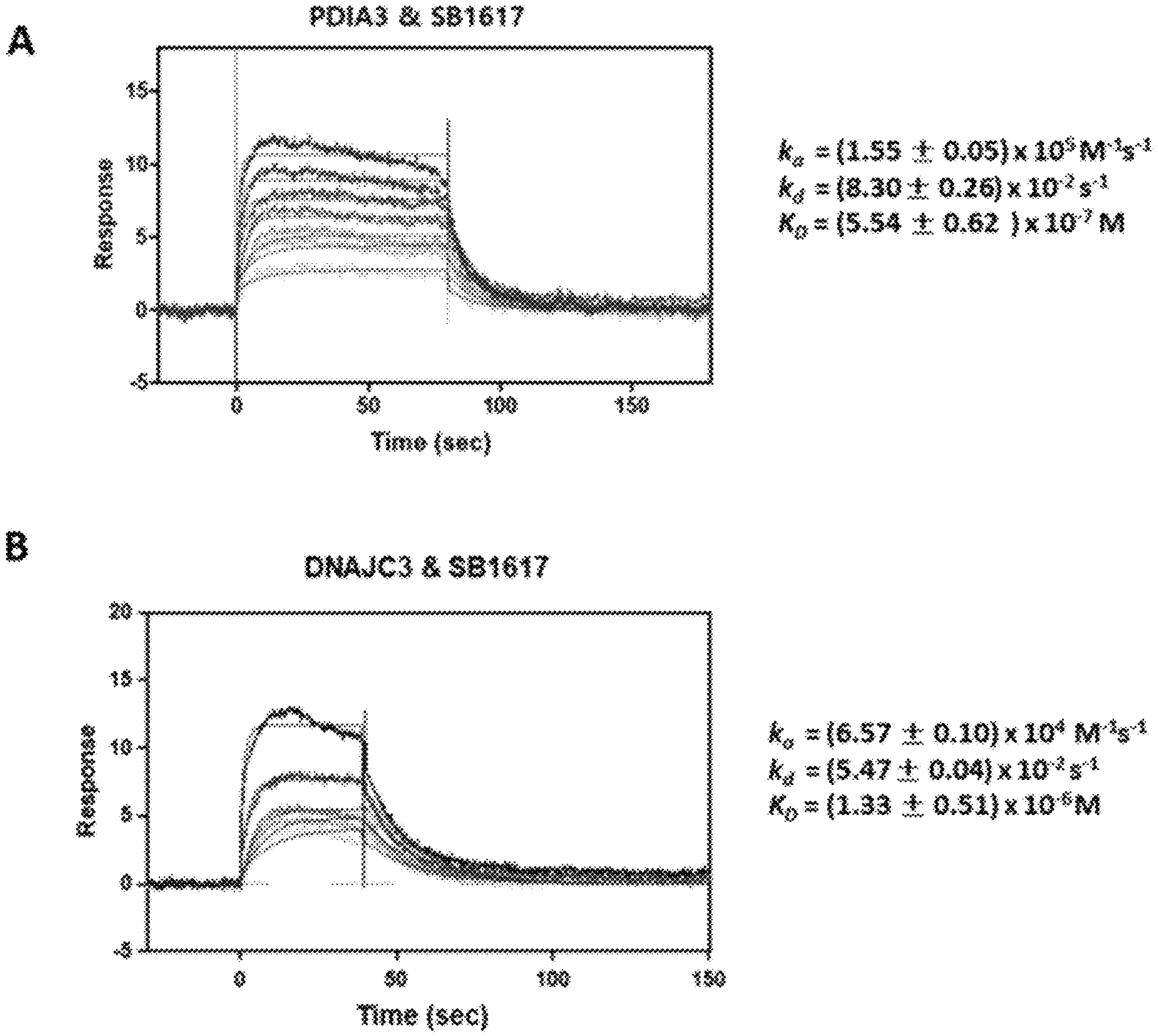

FIG. 11 shows the results of measuring the interaction of the pyrimidodiazepine derivative (SB1617) according to the present invention with (A) PDIA3 and (B) DNAJC using surface plasmon resonance spectroscopy.

Figure 12:
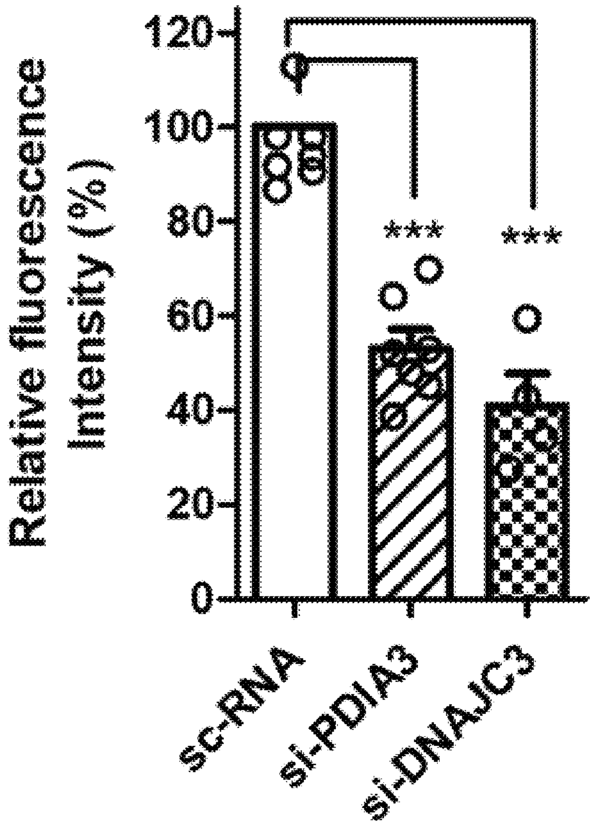

FIG. 12 shows the results of measuring the change in BiFC-tau-Venus fluorescence intensity according to the inhibition of PDIA3 or DNAJC3 expression.

Figure 13:
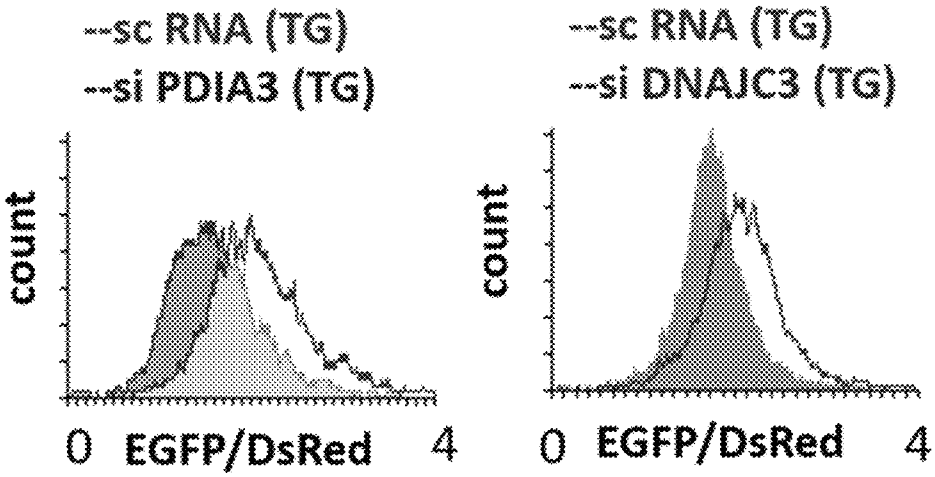

FIG. 13 shows the results of flow cytometry for confirming the change in the EGFP-tau/DsRed ratio according to the inhibition of PDIA3 or DNAJC3 expression.

Figure 14:
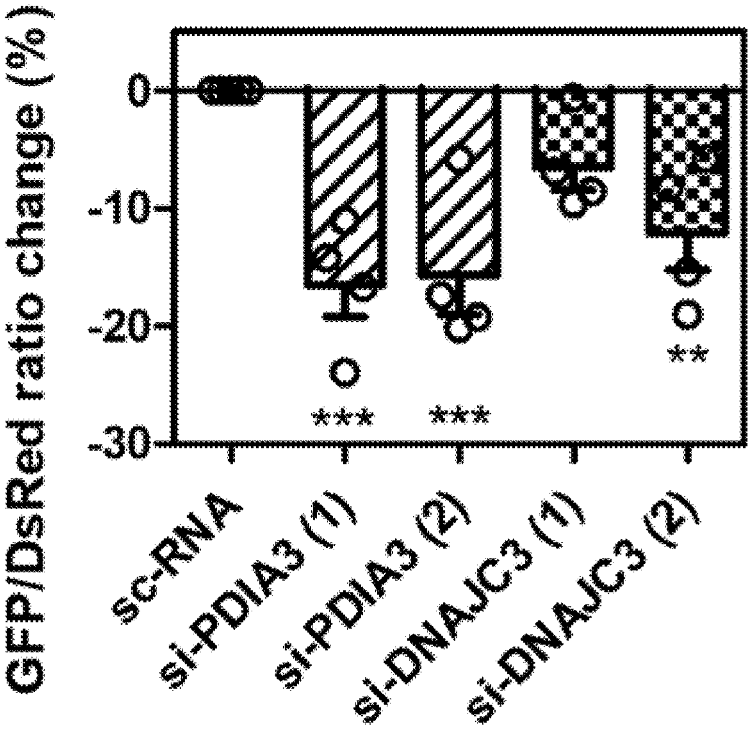

FIG. 14 shows the results of quantifying the change in the EGFP-tau/DsRed ratio according to the inhibition of PDIA3 or DNAJC3 expression.

Figure 15:
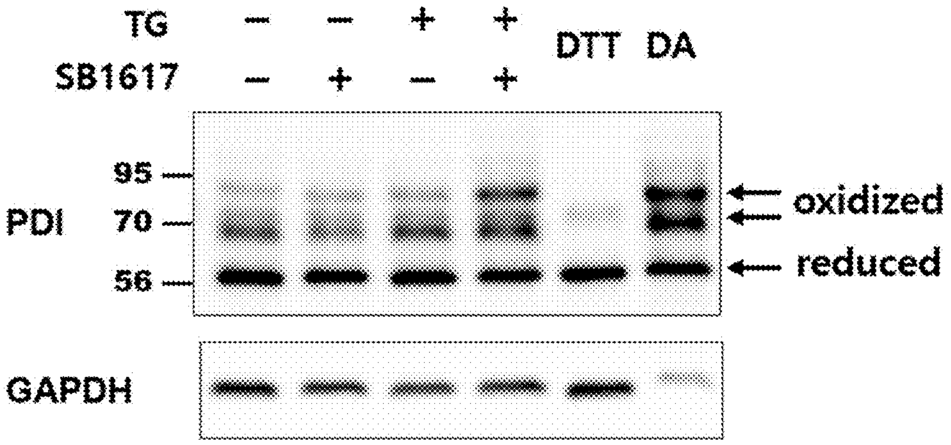

FIG. 15 shows the results of PEG-maleimide modification analysis for monitoring the oxidation state of PDI through alteration of PDIA3 reductase activity by the pyrimidodiazepine derivative (SB1617) according to the present invention.

Figure 16:
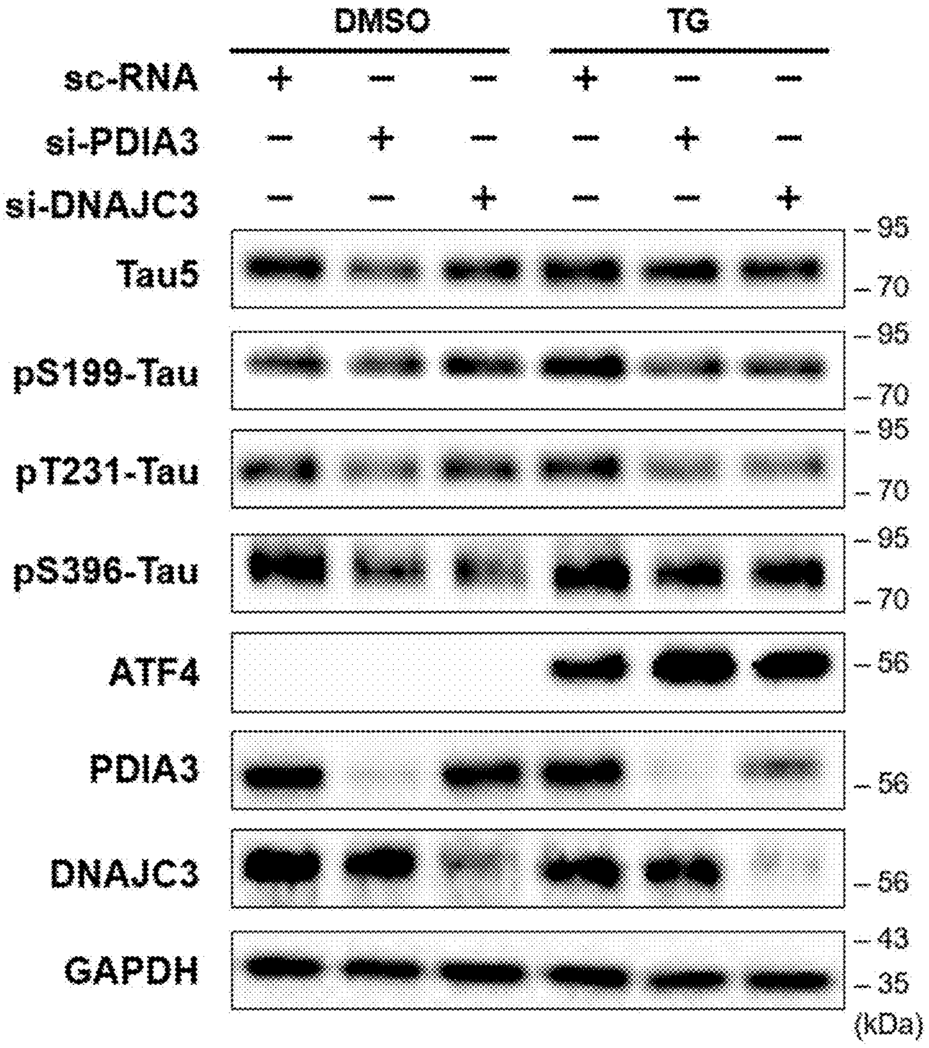

FIG. 16 shows the results of introducing siRNA against DNAJC3 or PDIA3 in HEK293 BiFC-Tau cells and confirming alteration of the PERK downstream pathway through immunoblot analysis.

Figure 17:
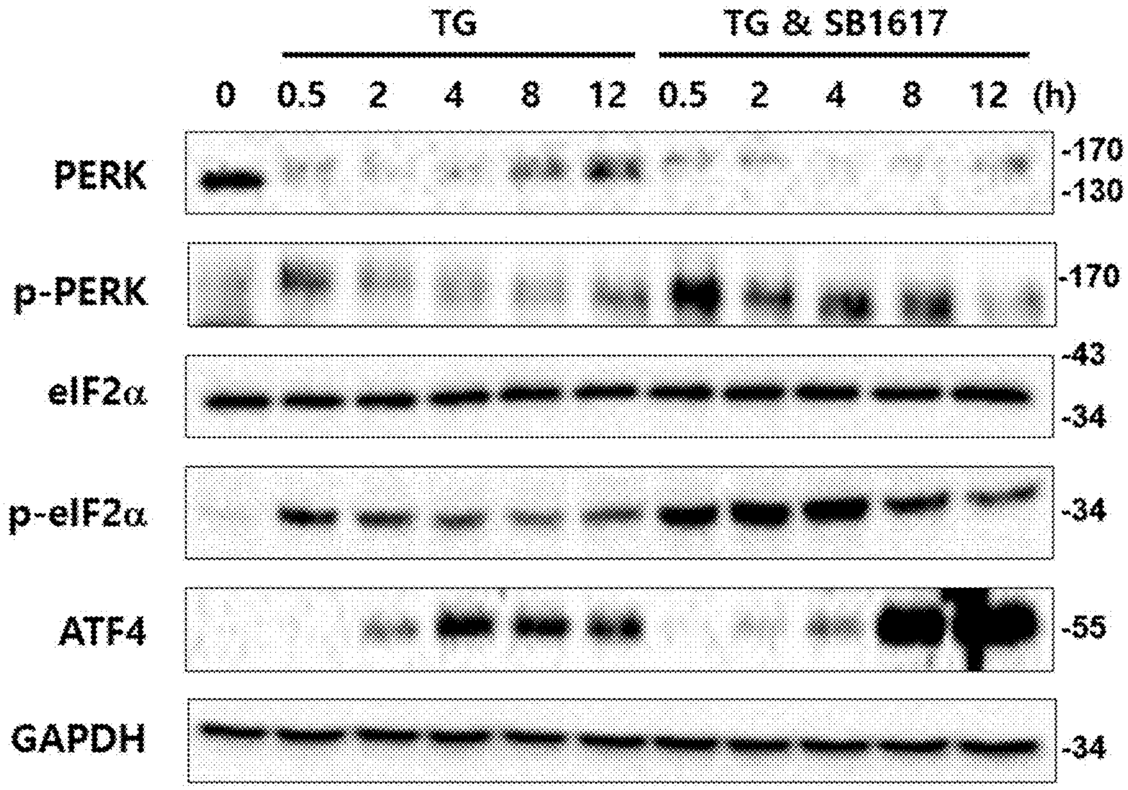

FIG. 17 shows the results of time course analysis of PERK activation in human neuroblastoma SH-SY5Y cells treated with a pyrimidodiazepine derivative (SB1716) according to the present invention when thapsigargin was added.

Figure 18:
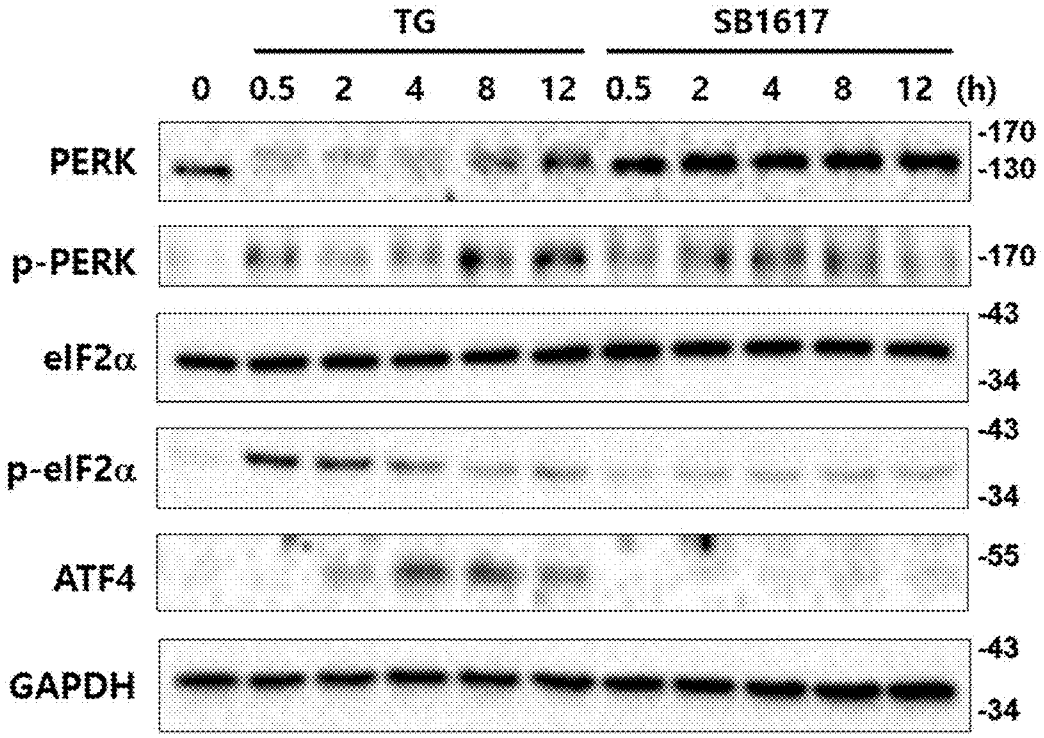

FIG. 18 shows the results of time course analysis of PERK activation in human neuroblastoma SH-SY5Y cells treated with a pyrimidodiazepine derivative (SB1716) according to the present invention when thapsigargin was not added.

Figure 19:
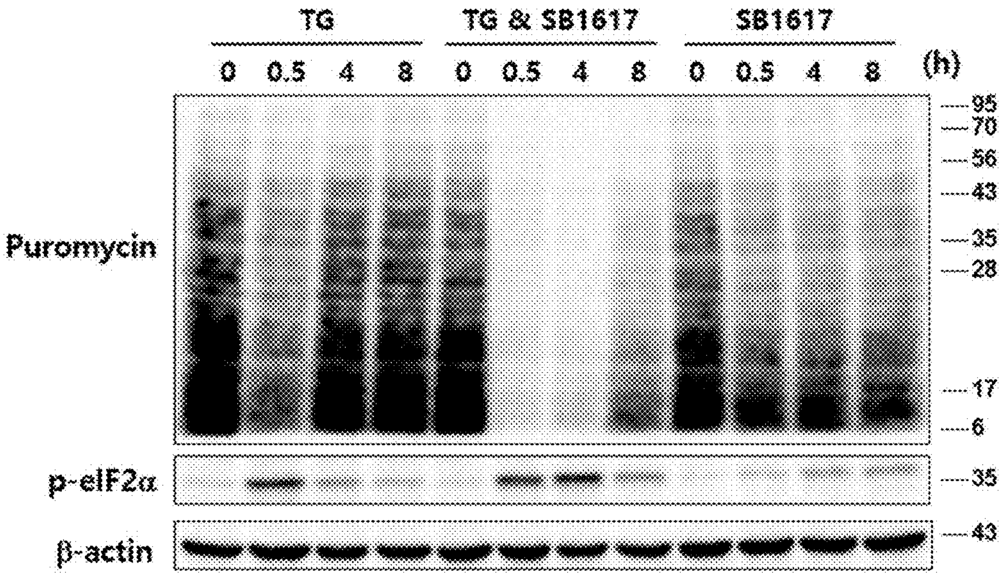

FIG. 19 shows the results of immunoblot analysis to confirm the ability to regulate translation by the pyrimidodiazepine derivative (SB1716) according to the present invention.

Figure 20:
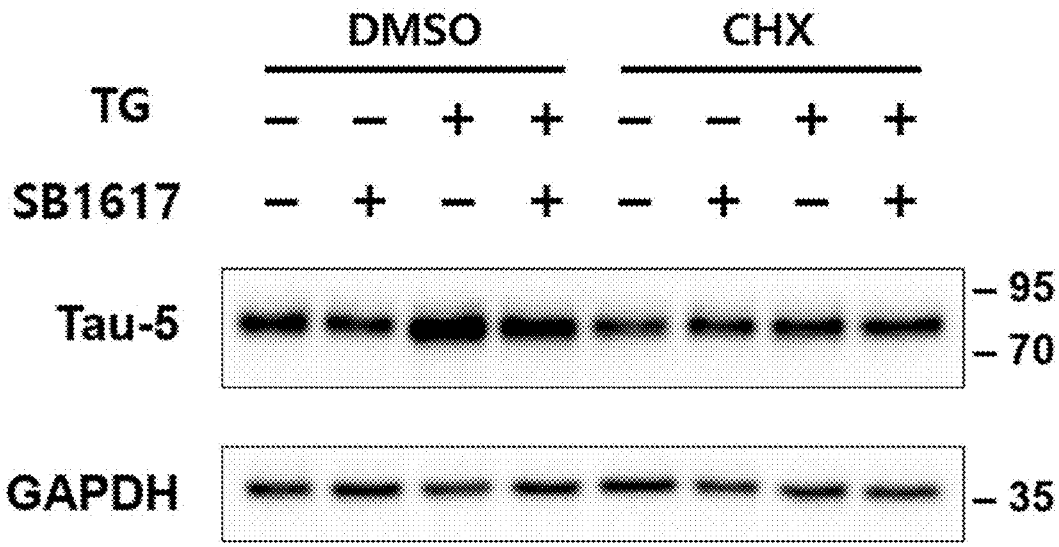

FIG. 20 shows the results of immunoblot analysis of the total tau level when treated with 10 μM pyrimidodiazepine derivative (SB1716) according to the present invention in the absence and presence of 200 nM TG and 20 μg/mL cycloheximide (CHX) in HEK293 BiFC-tau cells for 8 hours.

Figure 21:
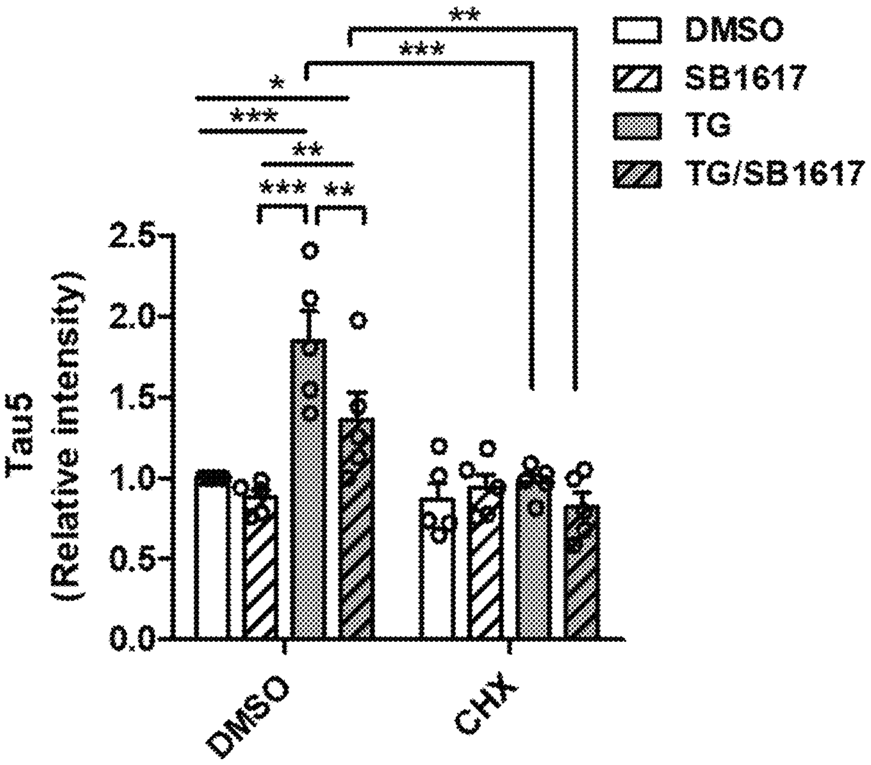

FIG. 21 is a graph quantifying the result of confirming the total tau level by immunoblot analysis when treated with 10 μM pyrimidodiazepine derivative (SB1716) according to the present invention in the absence and presence of 200 nM TG and 20 μg/mL cycloheximide (CHX) in HEK293 BiFC-tau cells for 8 hours.

Figure 22:
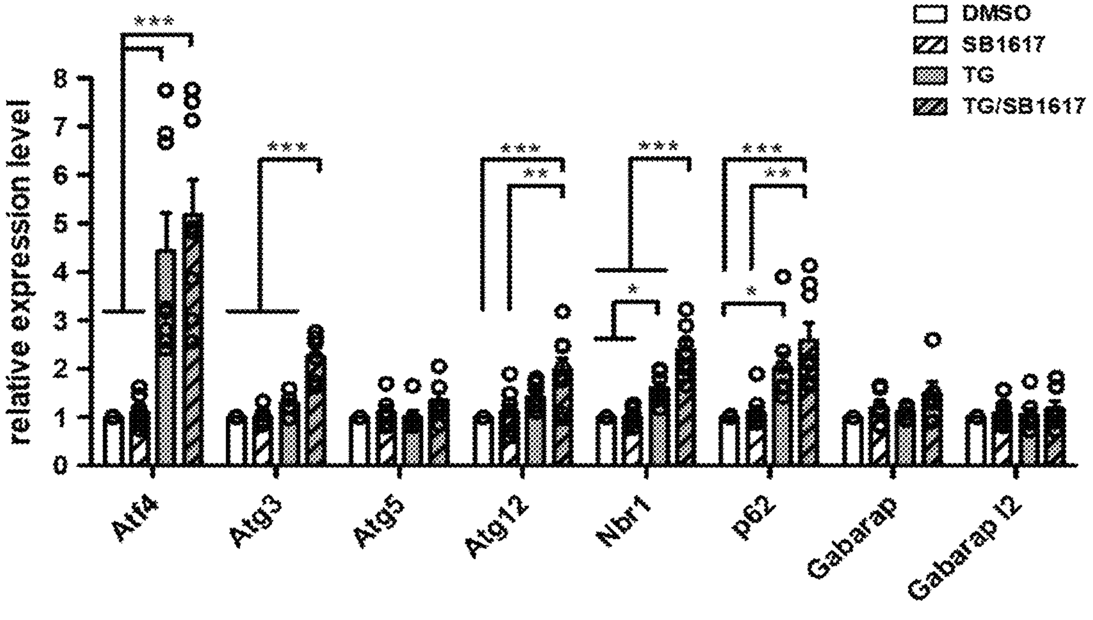

FIG. 22 shows the results of treating SH-SY5Y cells with 5 μM pyrimidodiazepine derivatives (SB1716) according to the present invention with or without 1 μM thapsigargin for 8 hours, and then analyzing autophagy-related genes regulated by ATF4 by RT-qPCR.

Figure 23:
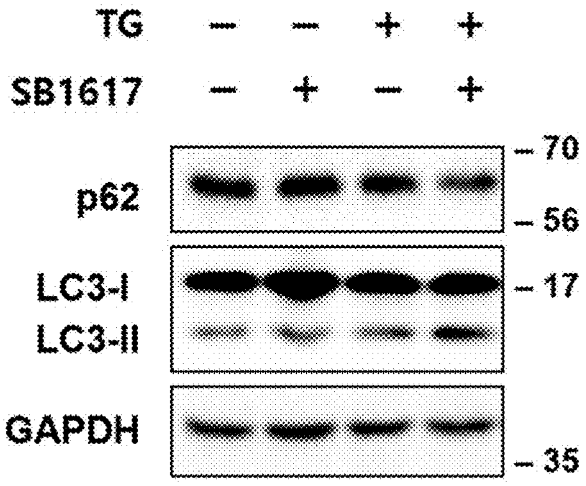

FIG. 23 shows the results of immunoblot analysis of conversion of LC3-I to LC3-II and p62 levels when HEK293 BiFC-tau cells were treated with 5 μM pyrimidodiazepine derivatives (SB1716) according to the present invention in the presence or absence of 500 nM TG for 6 hours.

Figure 24:
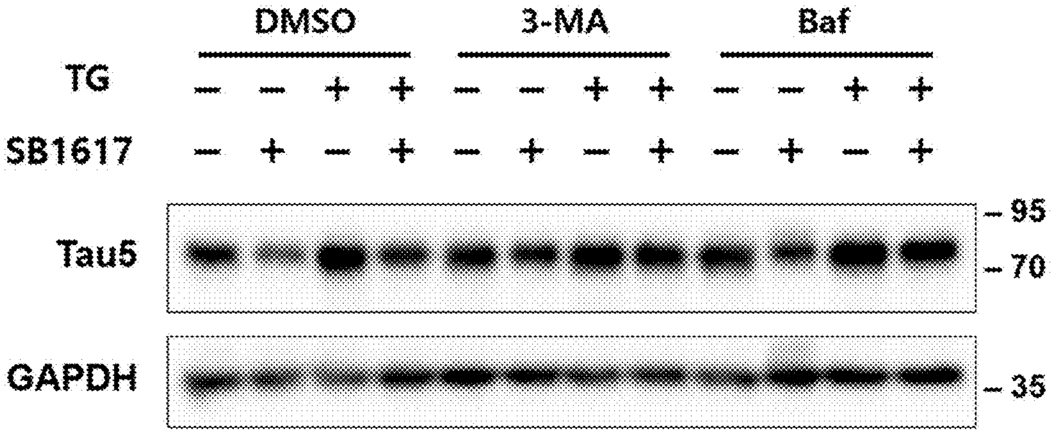

FIG. 24 shows the total tau levels according to the treatment of pyrimidodiazepine derivatives (SB1716) and TG according to the present invention in the absence and presence of the autophagy inhibitors 3-methyladenine (3-MA) and bafilomycin A1 (Baf) in HEK293 BiFC-tau cells by immunoblot analysis.

Figure 25:
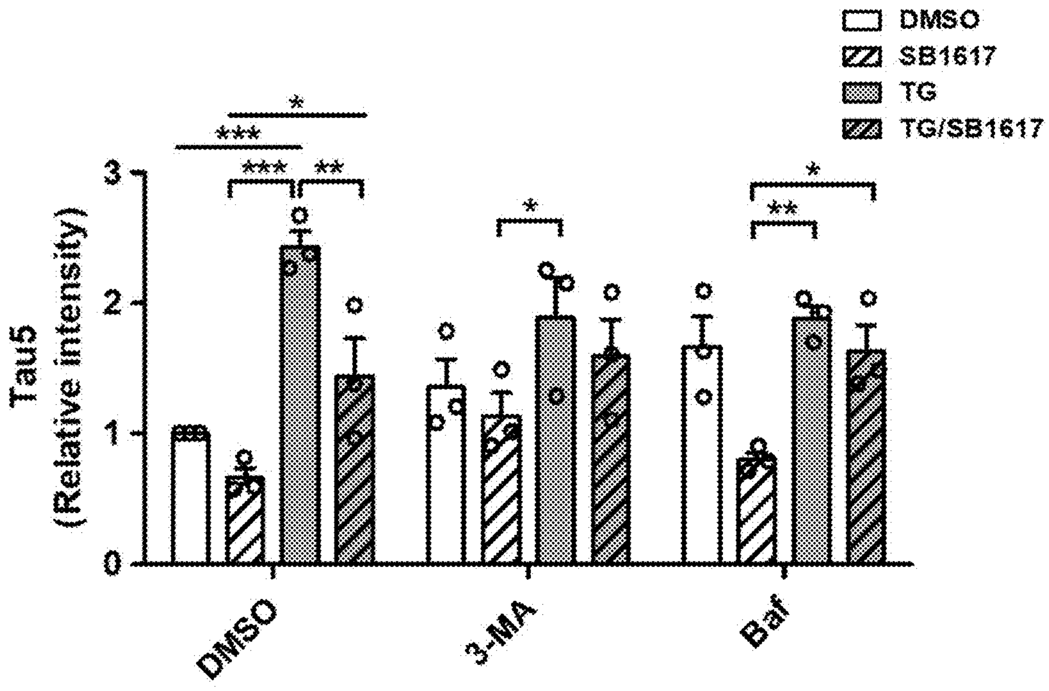

FIG. 25 is a graph quantifying the result of confirming the total tau level according to the treatment of pyrimidodiazepine derivatives (SB1716) and TG according to the present invention in the absence and presence of the autophagy inhibitors 3-methyladenine (3-MA) and bafilomycin A1 (Baf) in HEK293 BiFC-tau cells by immunoblot analysis.

Figure 26:
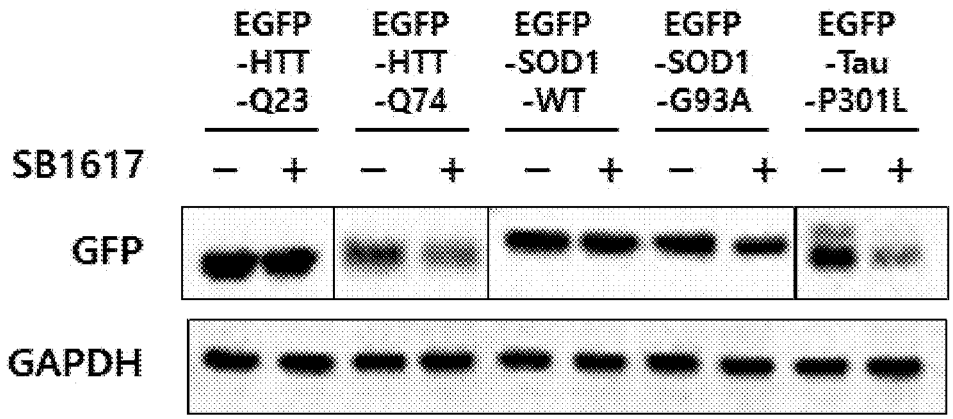

FIG. 26 shows the results of confirming changes in the mutation levels of tau P301L, SOD1 (G93A), and HET (Q74) according to the treatment of the pyrimidodiazepine derivative (SB1716) according to the present invention.

Figure 27:
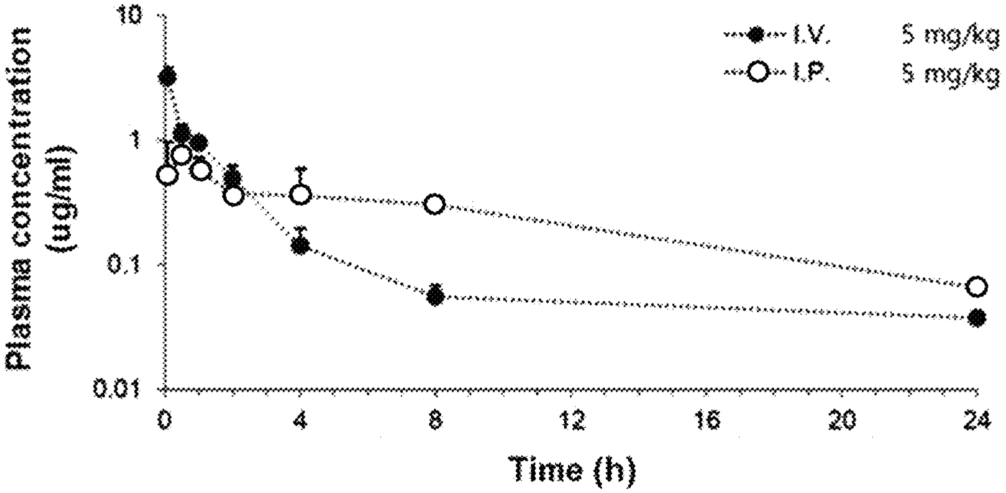

FIG. 27 shows the results of in vivo pharmacokinetic analysis of the pyrimidodiazepine derivative (SB1716) according to the present invention using male ICR mice.

Figure 28:
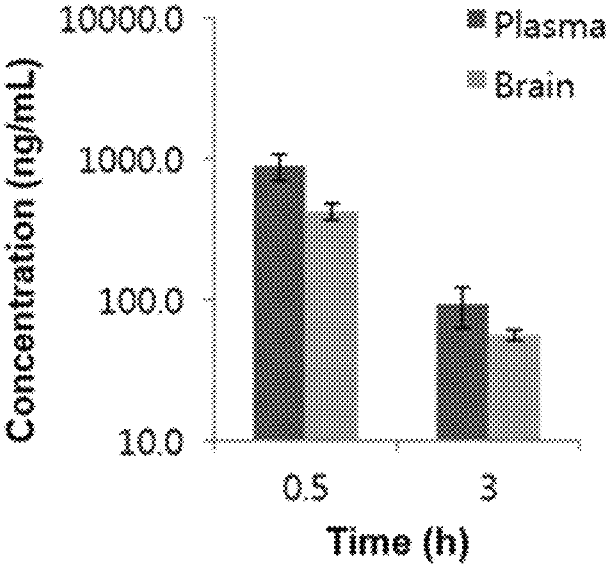

FIG. 28 shows the results of in vivo blood-brain barrier permeability evaluation of the pyrimidodiazepine derivative (SB1716) according to the present invention using male ICR mice.

Figure 29:
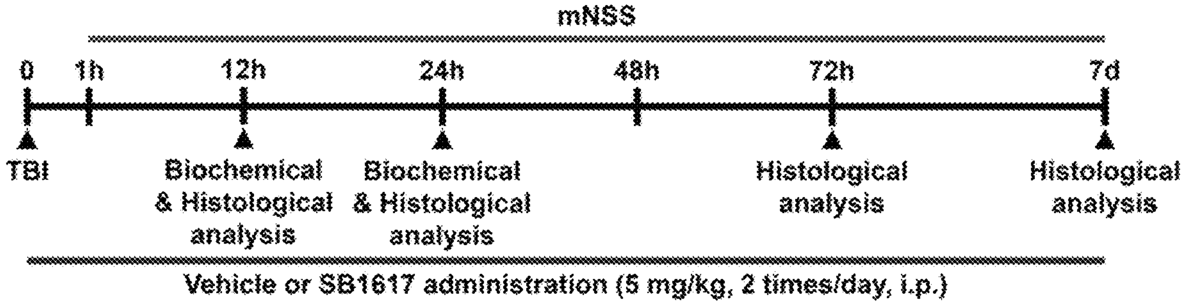

FIG. 29 schematically illustrates the experimental design in the TBI mouse model.

Figure 30:
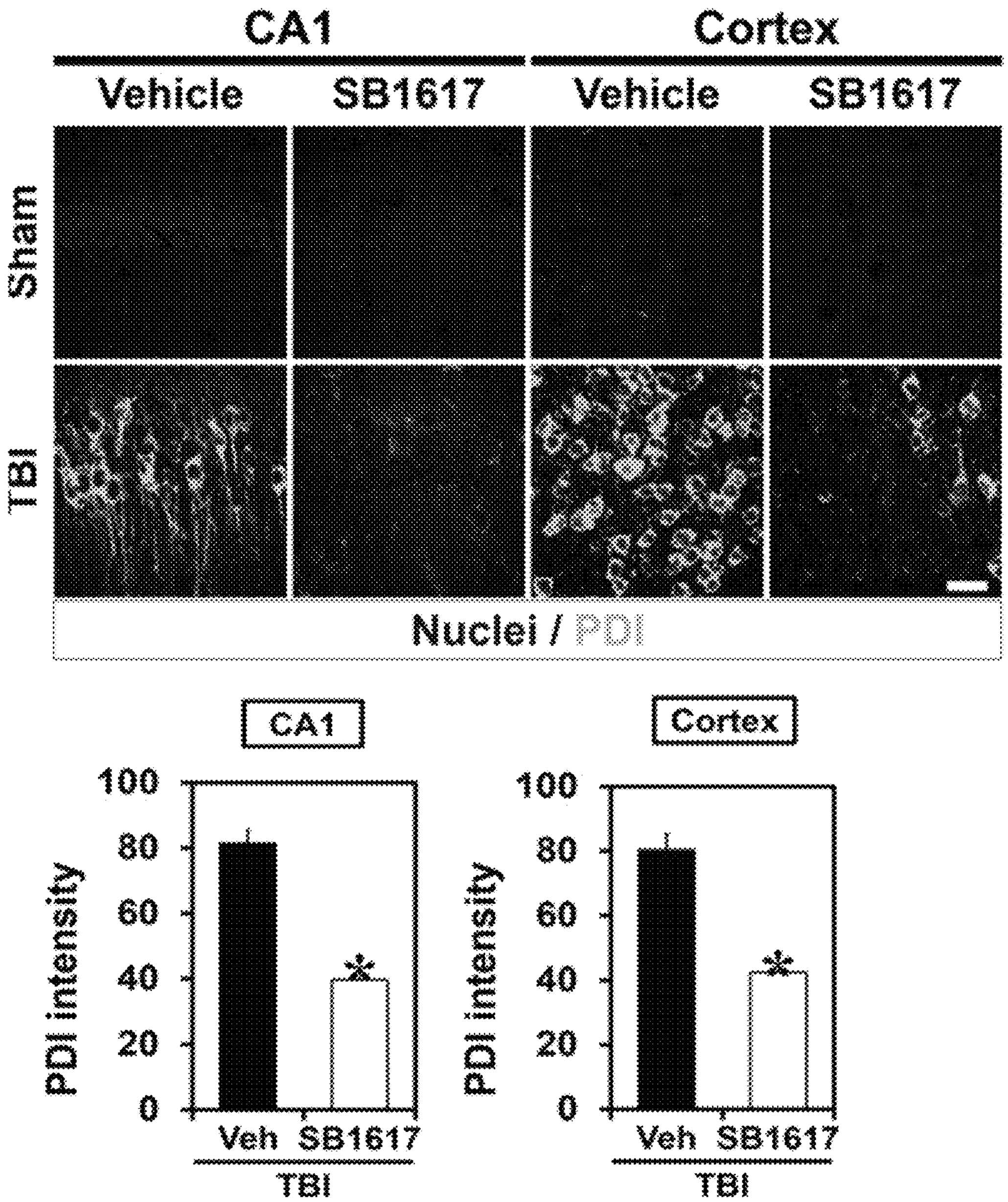

FIG. 30 shows the results of confirming the change in PDI level according to the treatment with the pyrimidodiazepine derivative (SB1716) according to the present invention in the ipsilateral hippocampal CA1 and cortex of the sham group and the TBI mouse model.

Figure 31:
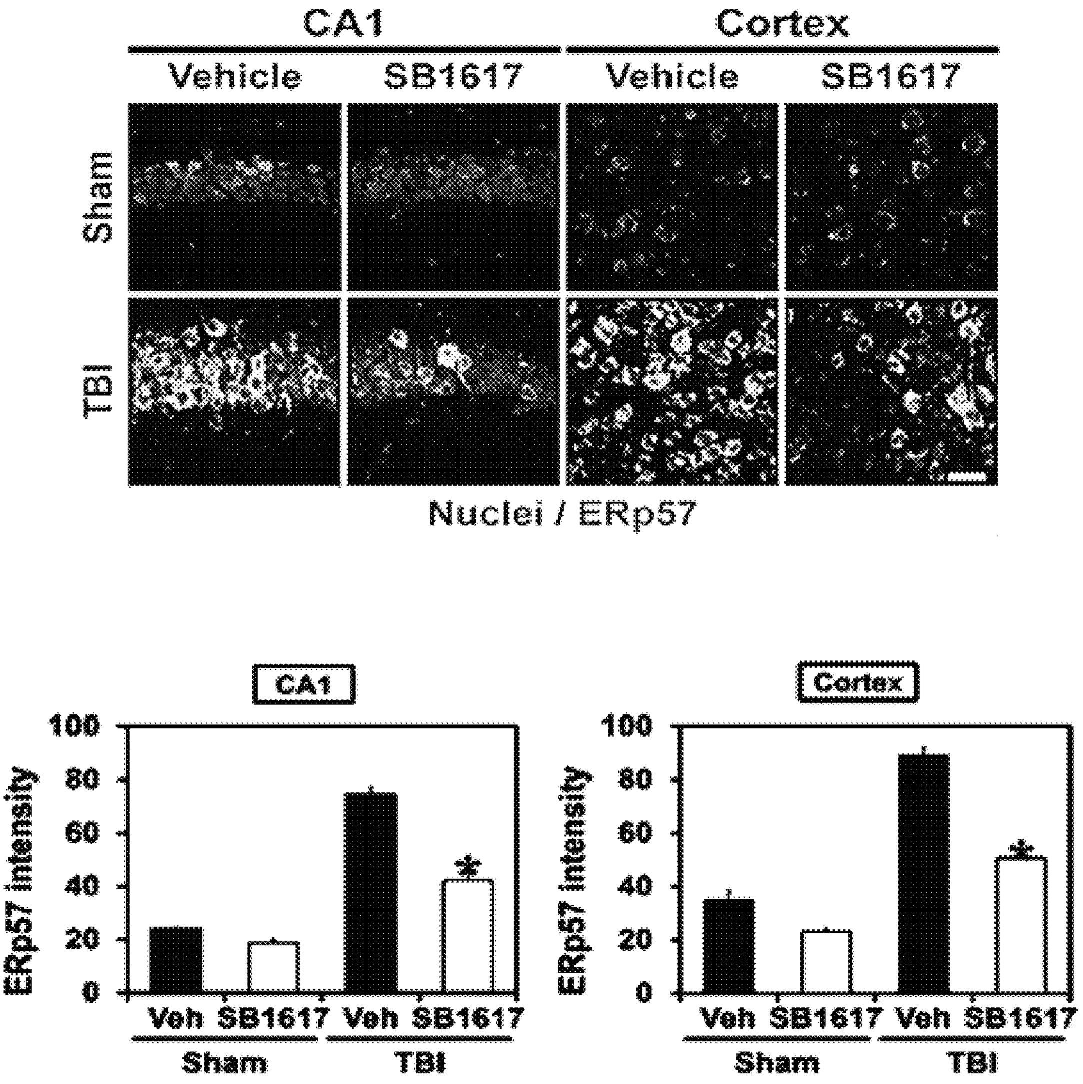

FIG. 31 shows the results of confirming the change in the level of ERp57 (PDIA3) according to the treatment with the pyrimidodiazepine derivative (SB1716) according to the present invention in the ipsilateral hippocampal CA1 and cortex of the sham group and the TBI mouse model.

Figure 32:
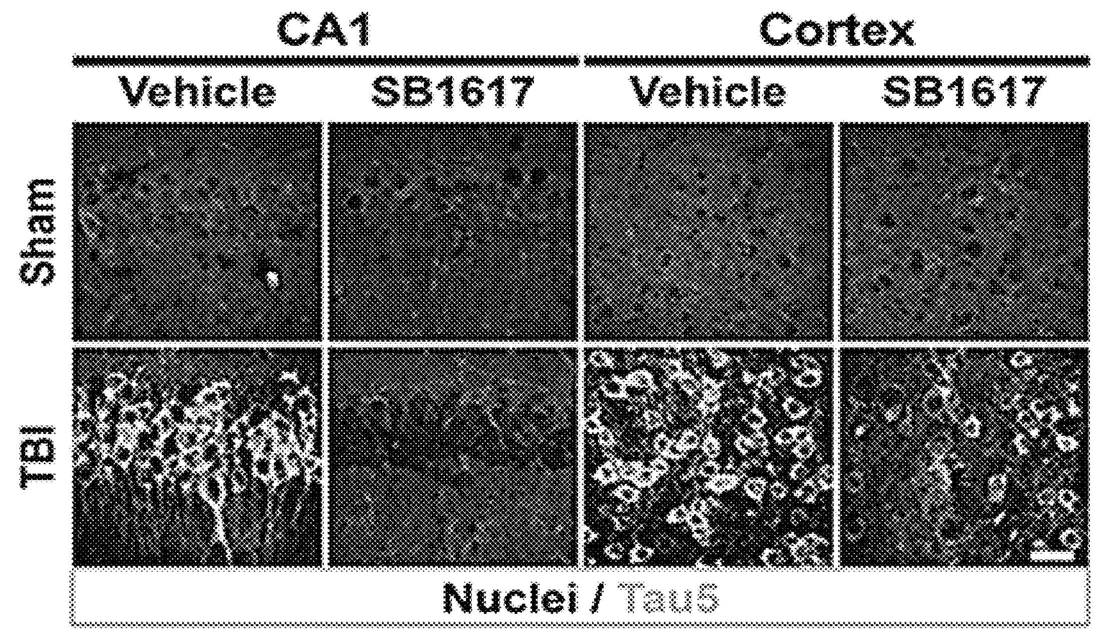
Figure 32:
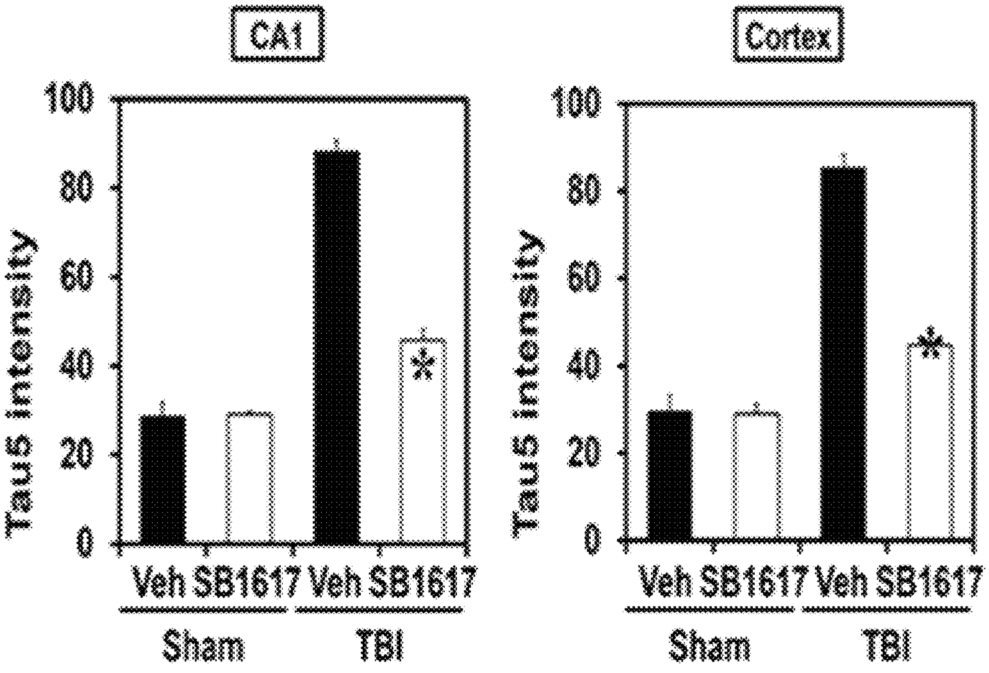

FIG. 32 shows the results confirming the change in the level of Tau5 according to the treatment with the pyrimidodiazepine derivative (SB1716) according to the present invention in the ipsilateral hippocampal CA1 and cortex of the sham group and the TBI mouse model.

Figure 33:
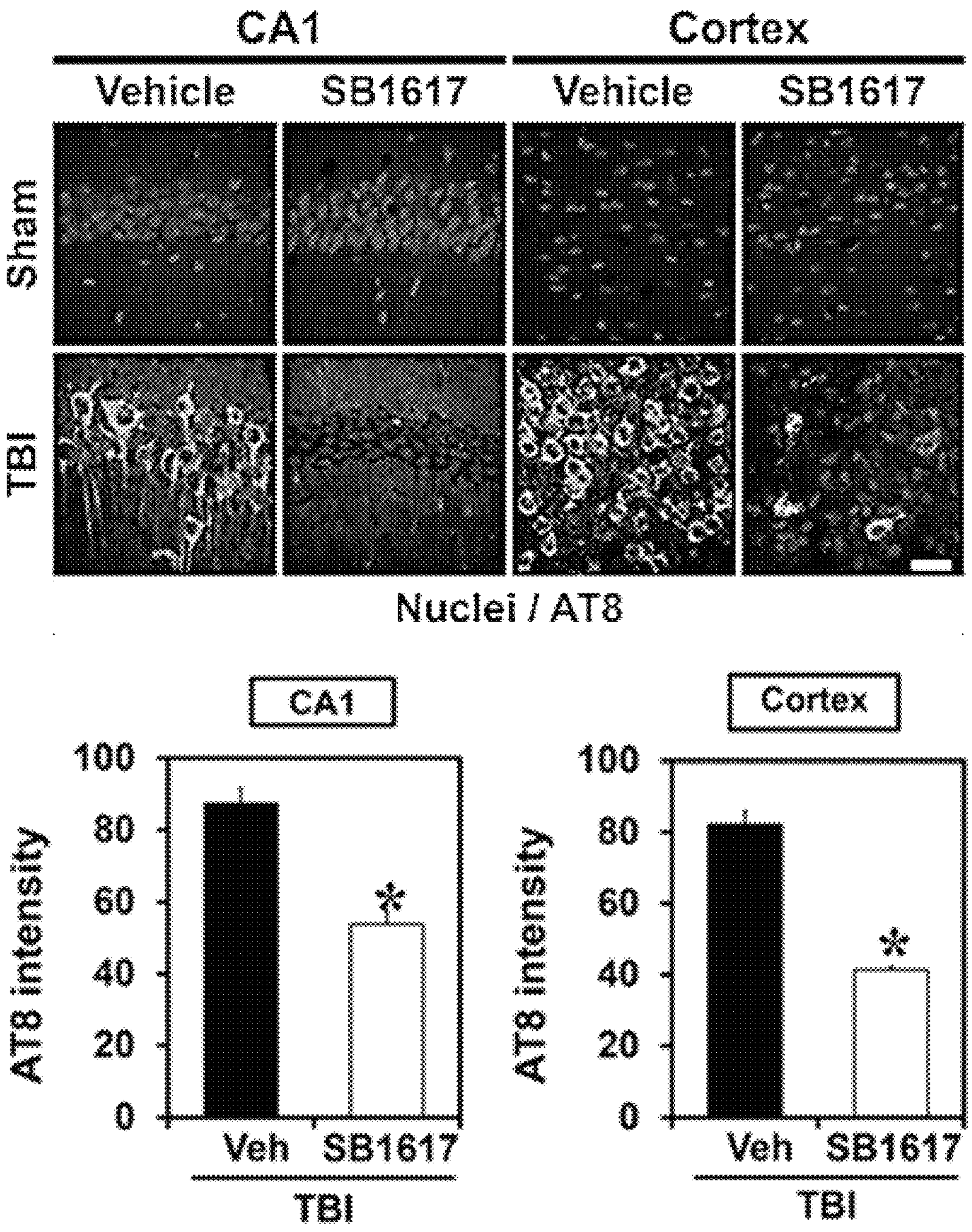

FIG. 33 shows the results of confirming the change in the level of AT8 according to the treatment with the pyrimidodiazepine derivative (SB1716) according to the present invention in the ipsilateral hippocampal CA1 and cortex of the sham group and the TBI mouse model.

Figure 34:
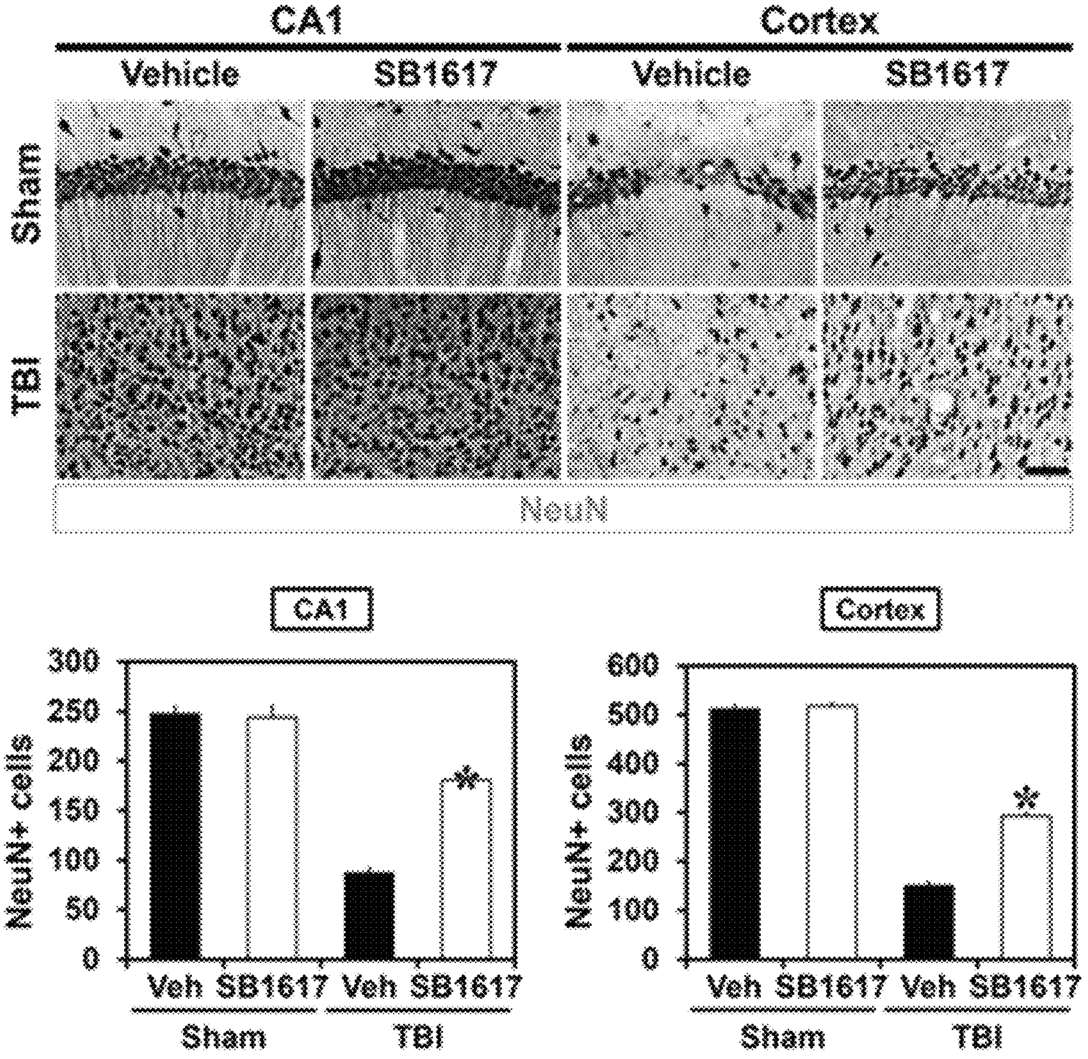

FIG. 34 shows the results of confirming the neuroprotective activity according to the treatment of the pyrimidodiazepine derivative (SB1716) according to the present invention in the ipsilateral hippocampal CA1 and cortex of the sham group and the TBI mouse model.

Figure 35:
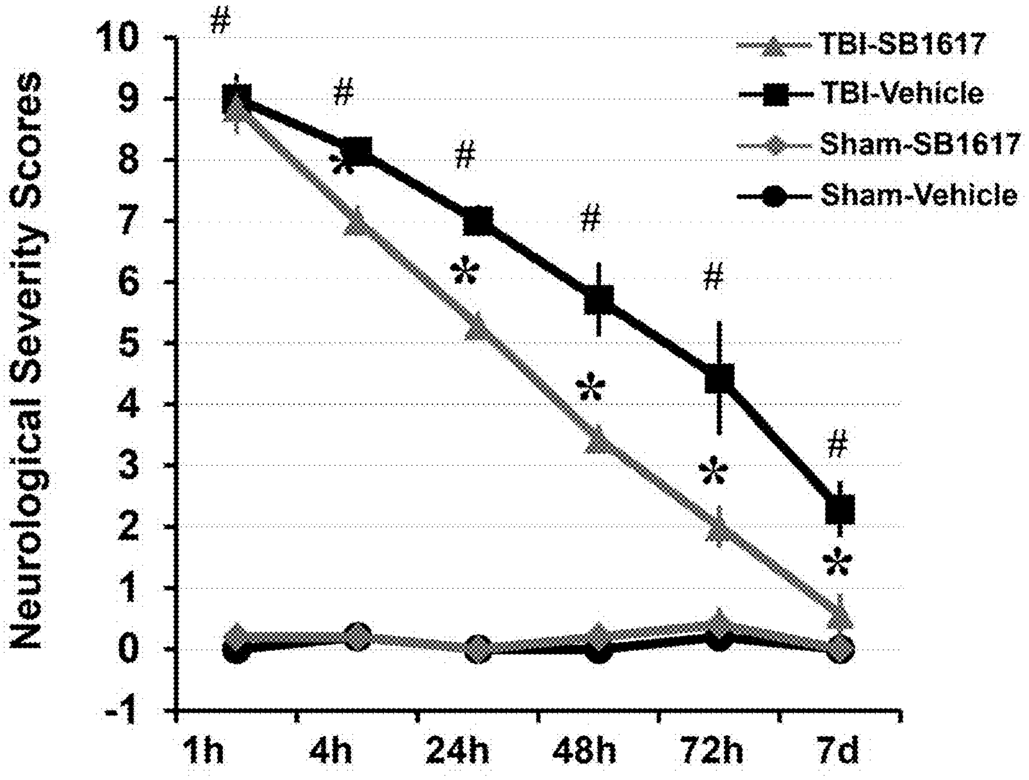

FIG. 35 shows the results of NSS (neurologic severity score) evaluation according to treatment with a pyrimidodiazepine derivative (SB1716) according to the present invention in the sham group and TBI mouse model.

Figure 36:
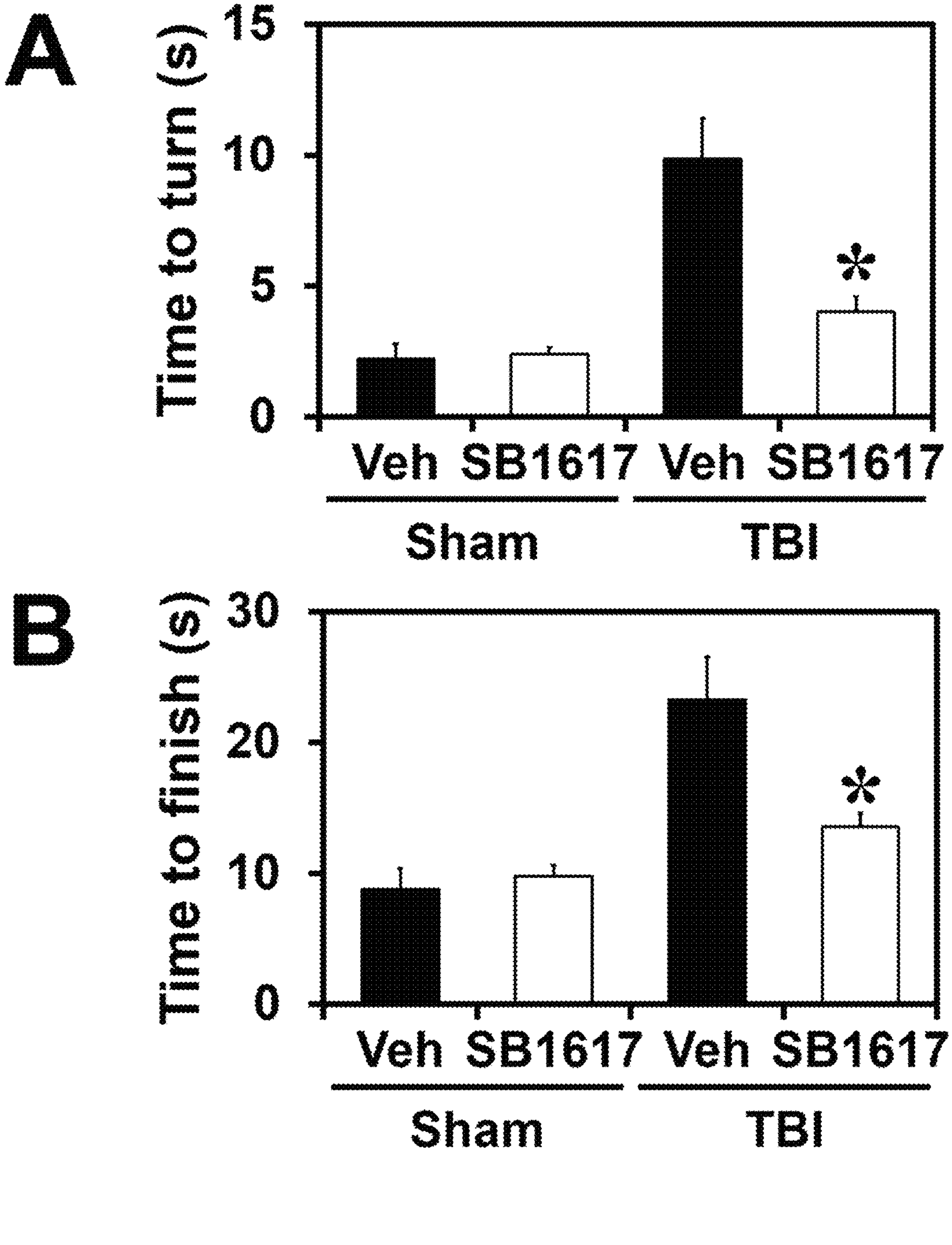

FIG. 36 shows the results of the pole climbing test in the sham group and the TBI mouse model.

Figure 37:
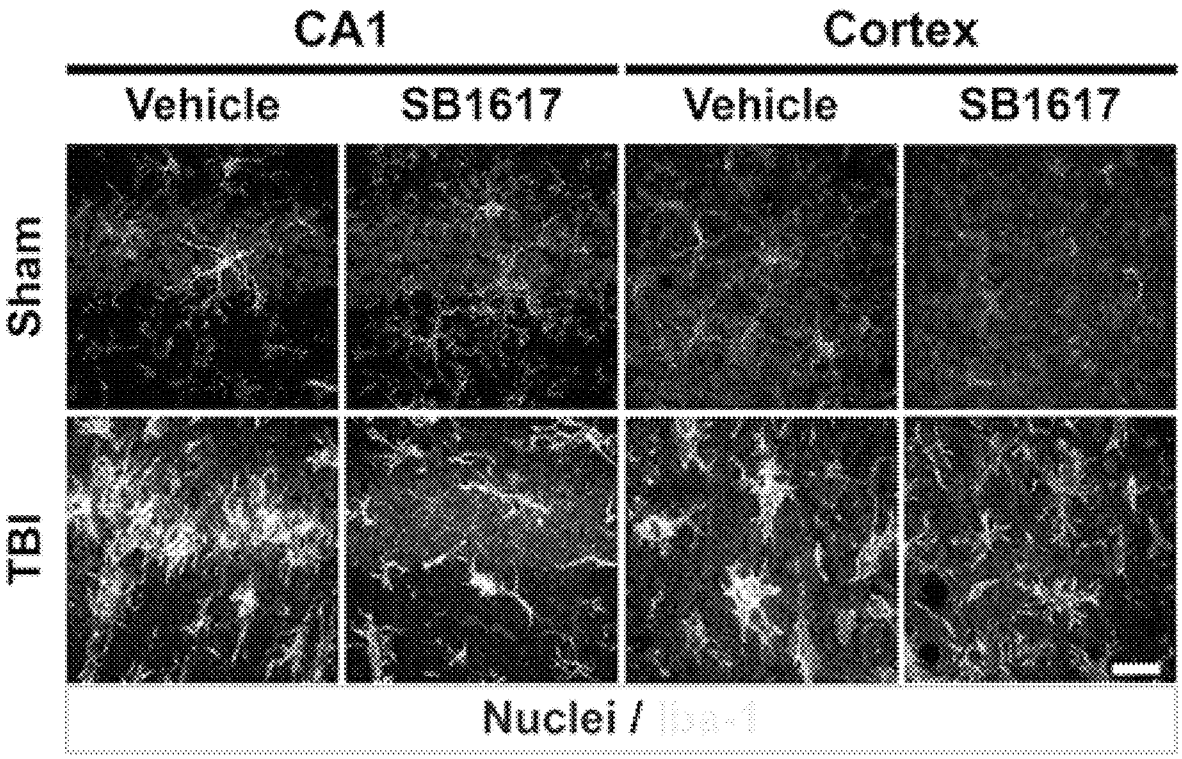

FIG. 37 shows the results of confirming changes in Iba-1 levels in the ipsilateral hippocampal CA1 and cortex of the mouse model treated with vehicle or SB1617 72 hours after sham surgery and TBI induction.

Figure 38:
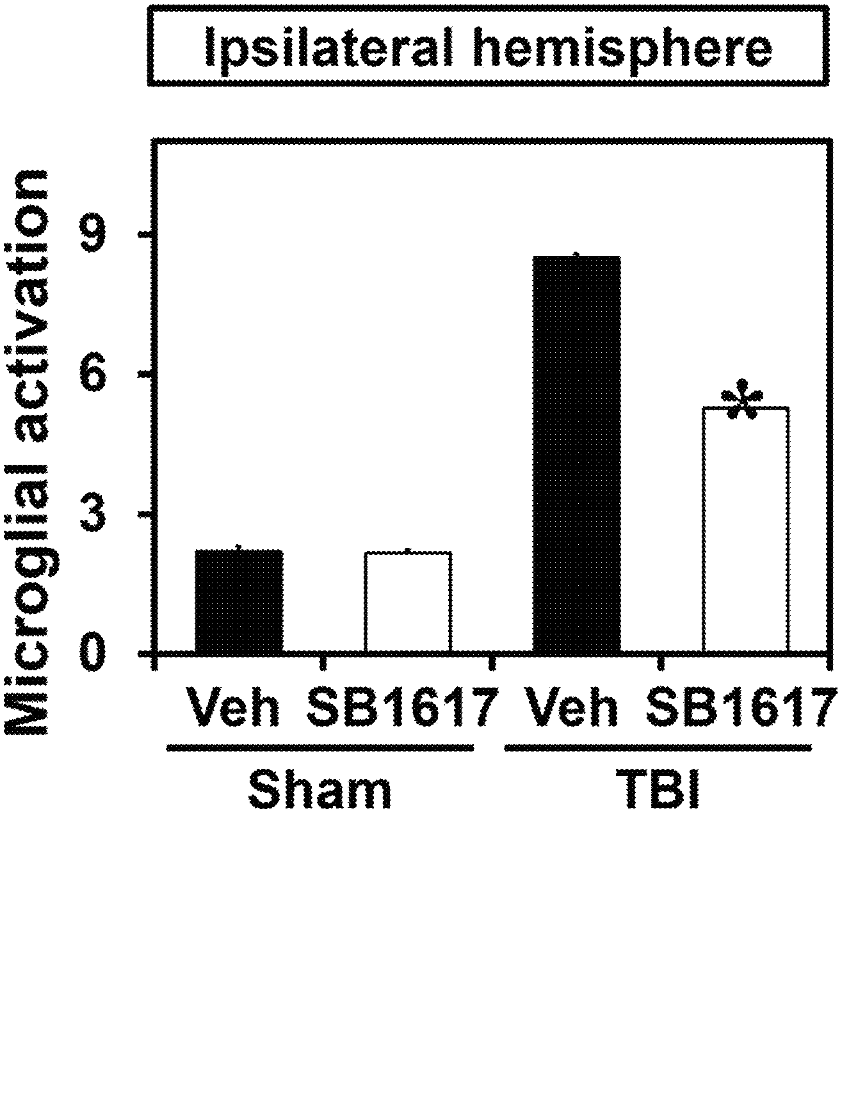

FIG. 38 shows the result of confirming the level of microglia activation according to treatment with vehicle or SB1617 in the ipsilateral hemisphere of the sham group and TBI mouse model.

Figure 39:
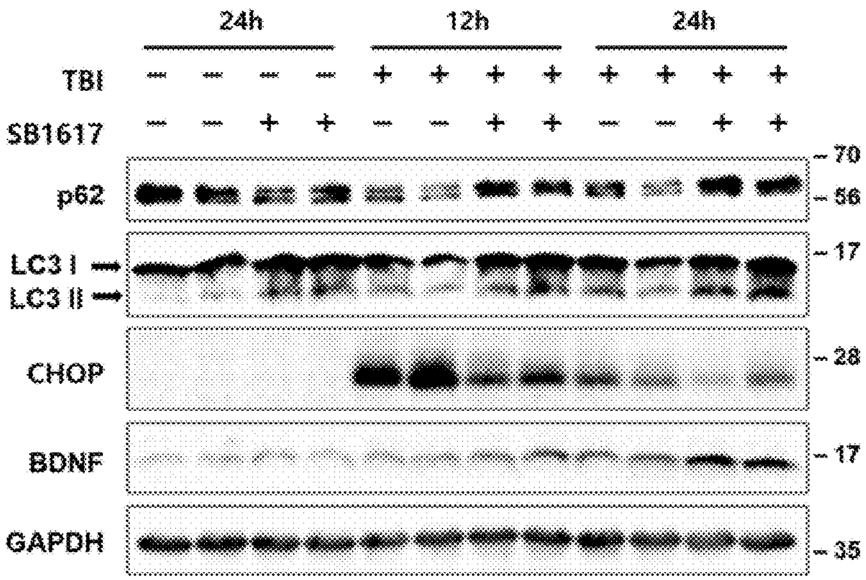

FIG. 39 shows the results of confirming p62, LC3-I to LC3-II conversion, BDNF and CHOP levels in the ipsilateral perilesional cortex of vehicle- or SB1617-treated mice at 12 and 24 hours after sham surgery or TBI induction by Western blotting analysis.

Figure 40:
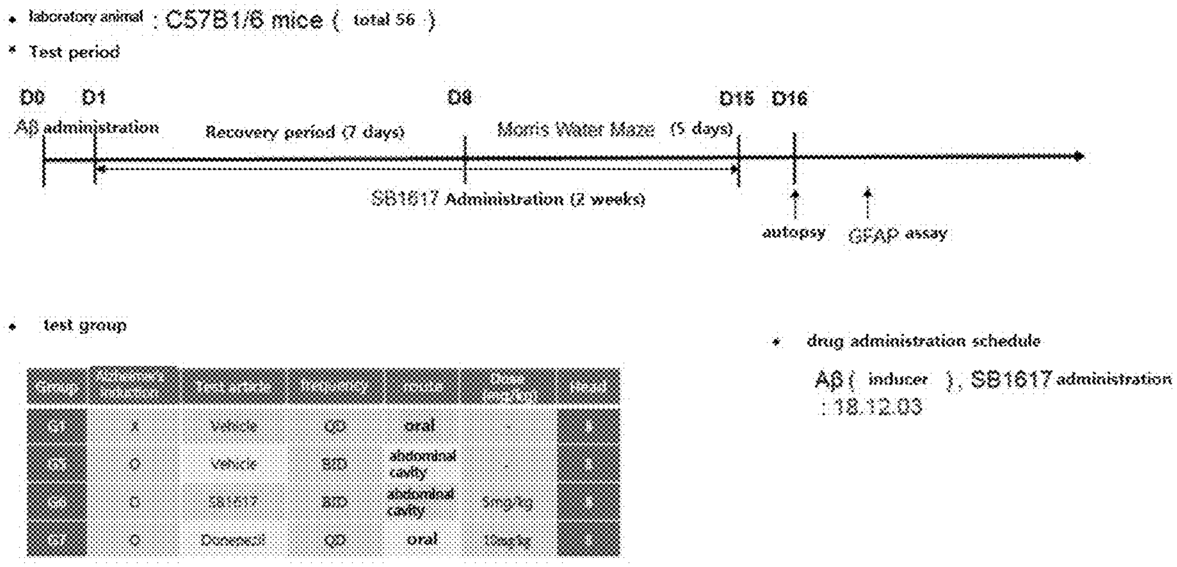

FIG. 40 schematically illustrates the experimental design in an acute Alzheimer's mouse model.

Figure 41:
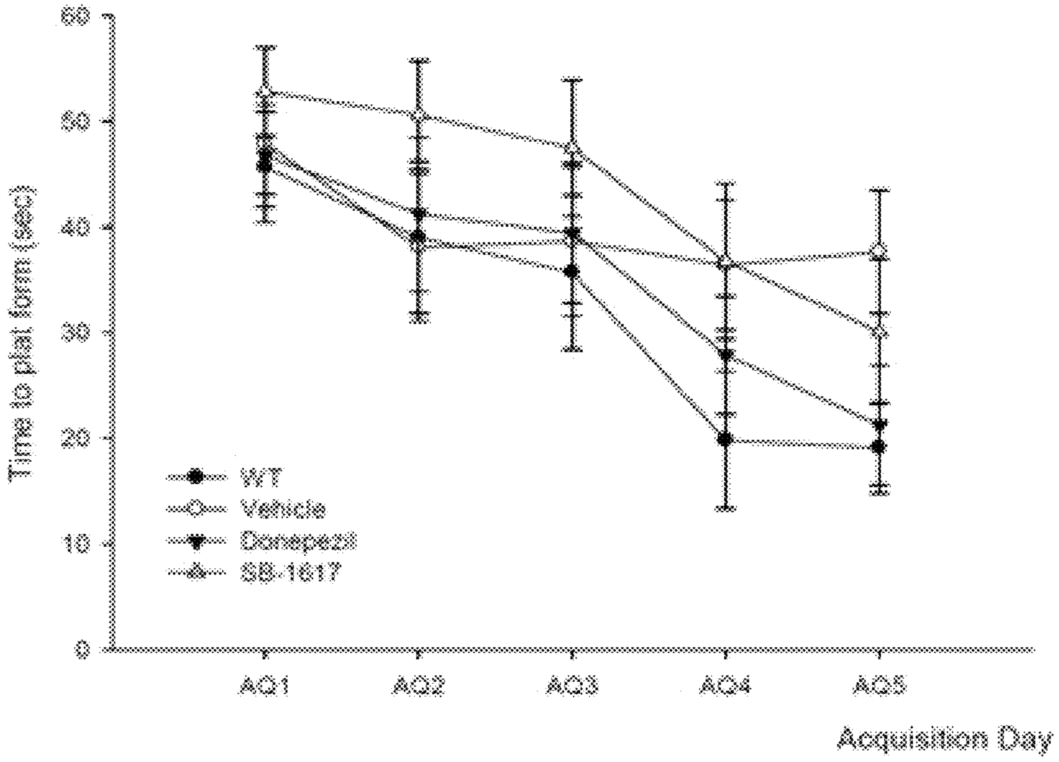

FIG. 41 shows the results confirming the therapeutic efficacy of the pyrimidodiazepine derivative (SB1716) according to the present invention through an Acquisition test in an acute Alzheimer's mouse model.

Figure 42:
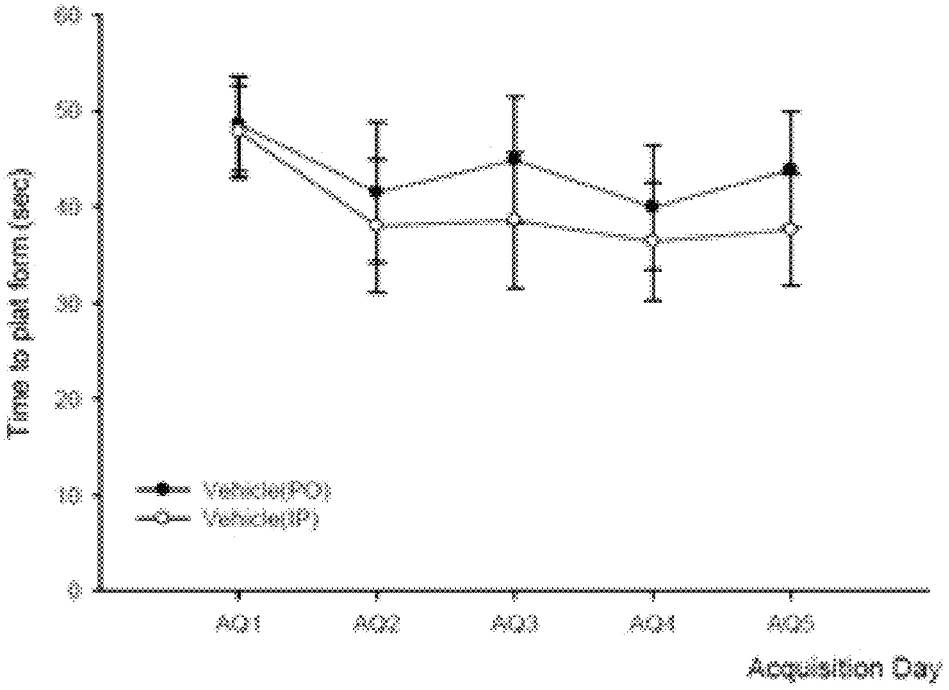

FIG. 42 shows the results of confirming the difference in learning ability according to the route of administration in an acute Alzheimer's mouse model.

Figure 43:
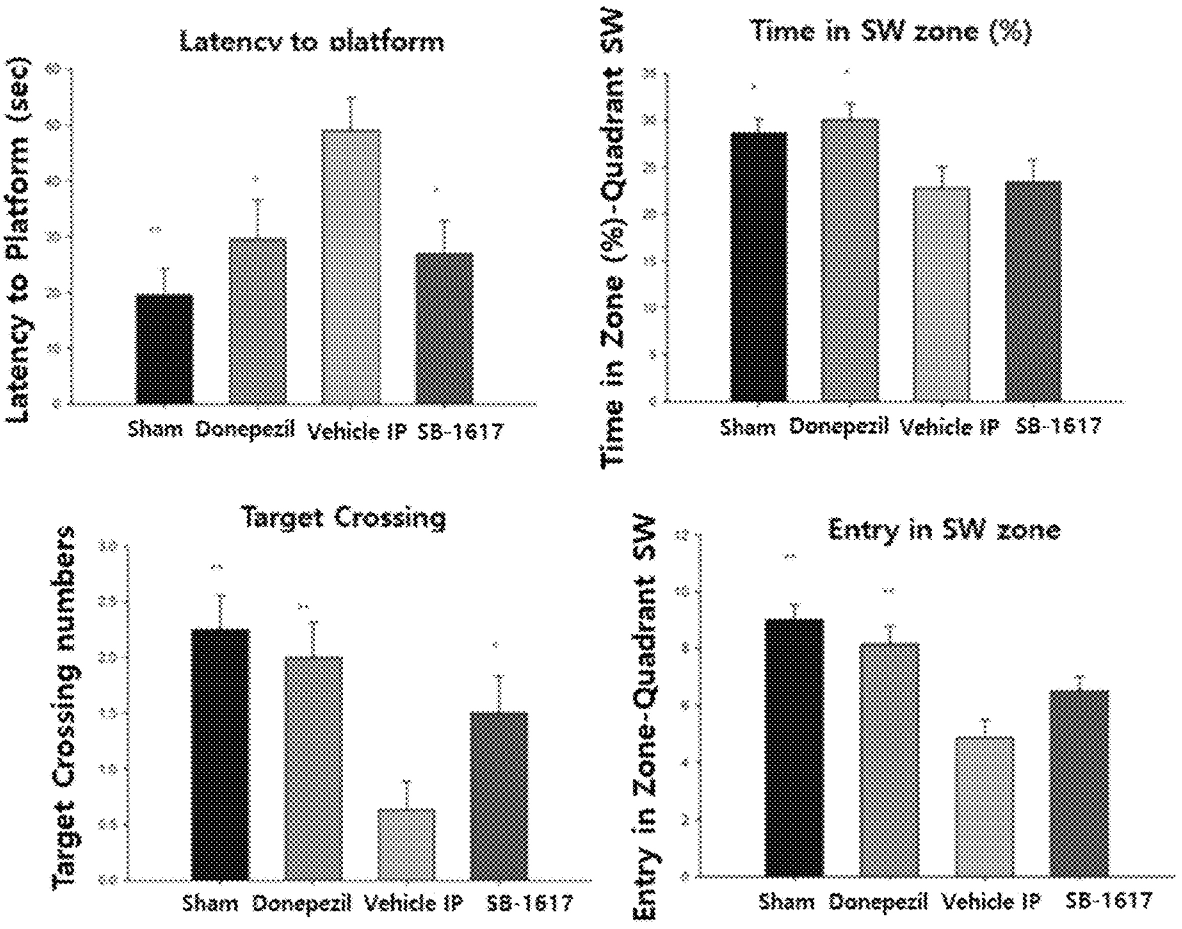

FIG. 43 shows the results of confirming the therapeutic efficacy of the pyrimidodiazepine derivative (SB1716) according to the present invention through a probe test in an acute Alzheimer's mouse model.

The present inventors discovered a pyrimidodiazepine derivative compound that inhibits tau aggregation, identified a target protein using TS-FITGE technology, and through additional mechanistic studies, confirming that the efficacy of the pyrimidodiazepine derivative compound for inhibiting tau aggregation is based on preventing inhibition of PERK signal activation through specific binding to DNAJC3 and PDIA3, and based on this, the present invention was completed.

Hereinafter, the present invention will be described in detail.

The present invention provides a compound represented by the following Formula 1, or a pharmaceutically acceptable salt thereof:

[Formula 1]

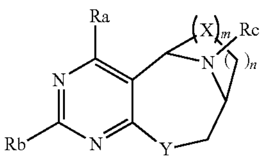

wherein the definitions of X, Y, m, n, Ra, Rb, and Rc are the same as described above.

According to one embodiment of the present invention, the compound represented by Formula 1 may be a compound represented by any one of the following Formulas 2 to 10 or a pharmaceutically acceptable salt thereof:

[Formula 2]

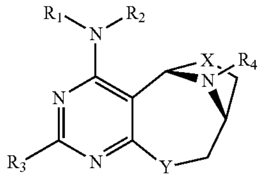

[Formula 3]

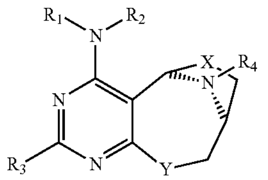

[Formula 4]

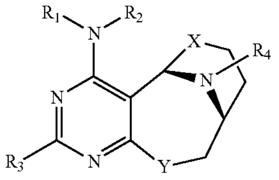

[Formula 5]

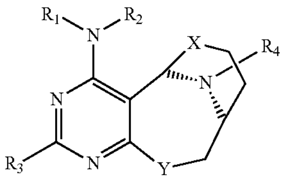

-continued

[Formula 6]

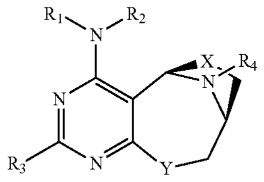

[Formula 7]

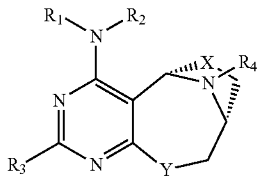

[Formula 8]

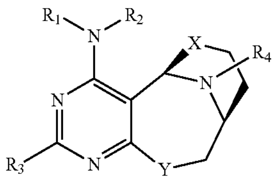

[Formula 9]

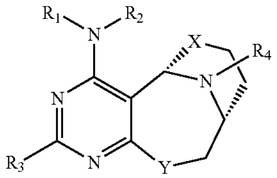

[Formula 10]

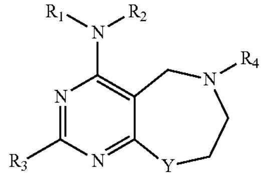

wherein

X and Y are the same as defined in claim 1;

$R_1$ and $R_2$ are each independently hydrogen; $C_1$-$C_{20}$ linear or branched alkyl; $C_1$-$C_{10}$ linear or branched aminoalkyl in which at least one hydrogen is substituted with an amine; arylalkyl in which any one hydrogen of $C_1$-$C_{10}$ linear or branched alkyl is substituted with $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; heteroarylalkyl in which any one hydrogen of $C_1$-$C_5$ alkyl is substituted with a 6-membered heteroaryl containing one N; phenoxyalkyl in which any hydrogen of $C_1$-$C_{10}$ linear or branched alkyl is substituted with a phenoxy group; $C_6$-$C_{20}$ aryl unsubstituted or substituted with one or more substituents selected from the group consisting of $C_1$-$C_{10}$ linear or branched alkoxy and azide; —COR'; —$SO_2$R'; —SOR'; —COR'R"; or —COOR';

$R_3$ is hydrogen; $C_1$-$C_{20}$ linear or branched alkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; —NR'R"—SR'; —$SO_2$R'; or —SOR';

$R_4$ is hydrogen; $C_1$-$C_{20}$ linear or branched alkyl; $C_6$-$C_{20}$ aryl unsubstituted or substituted with one or more selected from the group consisting of halogen, $C_1$-$C_{10}$ linear or branched alkyl, $C_1$-$C_{10}$ linear or branched alkoxy, and azide; —COR'; —SOR'; —$SO_2$R'; —COOR';-CONHR'; or —CONR'R";

R' and R" in the definitions of $R_1$ to $R_4$ are each independently hydrogen; $C_1$-$C_{10}$ linear or branched alkyl; $C_3$-$C_{10}$ cycloalkyl; $C_6$-$C_{20}$ aryl unsubstituted or substituted with one or more selected from the group consisting of halogen, $C_1$-$C_{10}$ linear or branched alkyl, $C_1$-$C_{10}$ linear or branched alkynyl, $C_1$-$C_{10}$ linear or branched alkoxy and nitro; benzyl; 5- to 20-membered heteroaryl containing 1 to 3 heteroatoms selected from N, O and S.

According to another embodiment of the present invention, in Formulas 2 to 10, X is O, S, or $SO_2$; Y is NRy, wherein Ry is hydrogen, $C_1$-$C_{10}$ linear or branched alkyl, or —COR', wherein R' is the same as defined in Formula 1; $R_1$ is arylalkyl in which any one hydrogen of $C_1$-$C_{10}$ linear or branched alkyl is substituted with $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; $R_2$ is hydrogen or $C_1$-$C_{20}$ linear or branched alkyl; $R_3$ is hydrogen or $C_1$-$C_{20}$ linear or branched alkyl; $R_4$ is —SOR' or —$SO_2$R', wherein R' may be the same as defined in Formulas 2 to 10 above.

According to another embodiment of the present invention, in Formulas 2 to 10, $R_1$ may be a group represented by the following Formula 11, and $R_4$ may be a group represented by the following Formula 12:

[Formula 11]

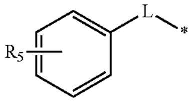

[Formula 12]

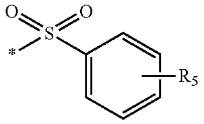

wherein

L is a single bond or $C_1$-$C_{10}$ linear or branched alkyl;

$R_5$ is hydrogen; halogen; $C_1$-$C_{20}$ linear or branched alkyl; $C_1$-$C_{10}$ linear or branched alkoxy; azide; or $C_6$-$C_{20}$ aryl unsubstituted or substituted with one or more substituents selected from the group consisting of $C_1$-$C_{10}$ linear or branched alkyl and halogen;

$R_6$ is halogen, $C_1$-$C_{10}$ linear or branched alkyl, $C_1$-$C_{10}$ linear or branched alkynyl, $C_1$-$C_{10}$ linear or branched alkoxy, or nitro.

According to another embodiment of the present invention, the compound of the present invention or a pharmaceutically acceptable salt thereof may be represented by Formula 2.

According to another embodiment of the present invention, the compound represented by Formula 1 may be a compound represented by Formula 13 or a pharmaceutically acceptable salt thereof:

[Formula 13]

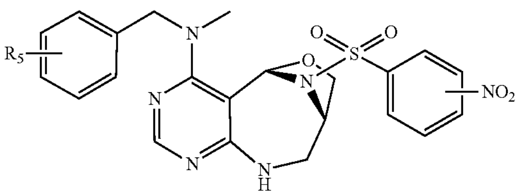

wherein $R_5$ is hydrogen; halogen; $C_1$-$C_{20}$ linear or branched alkyl; $C_1$-$C_{10}$ linear or branched alkoxy; azide; or $C_6$-$C_{20}$ aryl unsubstituted or substituted with one or more substituents selected from the group consisting of $C_1$-$C_{10}$ linear or branched alkyl and halogen.

According to another embodiment of the present invention, $R_5$ in Formula 13 may be hydrogen; halogen; or azide.

In one specific embodiment, the compound may be any one compound selected from the group consisting of the following compounds 101 to 136:

101

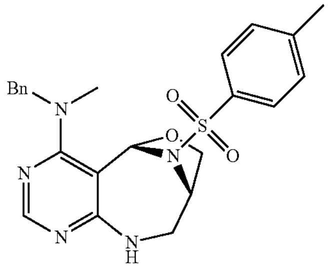

102

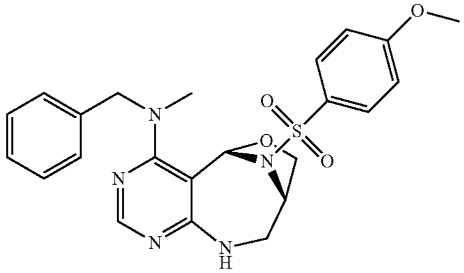

103

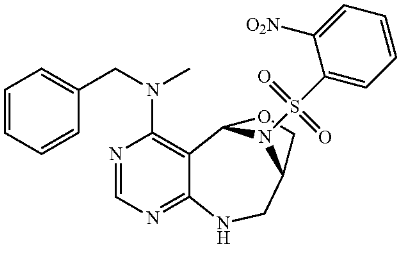

-continued
104
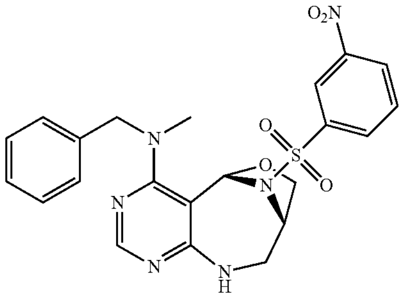
105
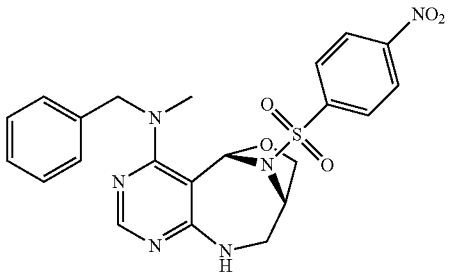
106
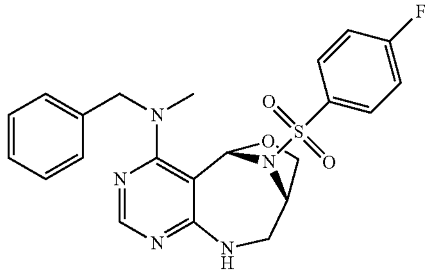
107
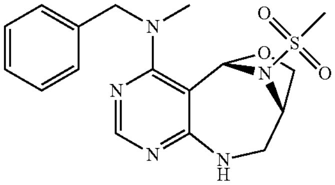
108
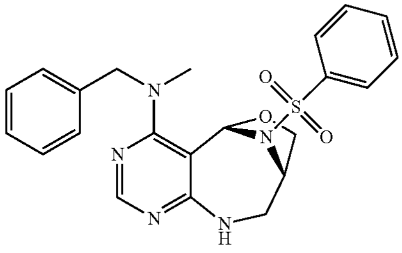
109
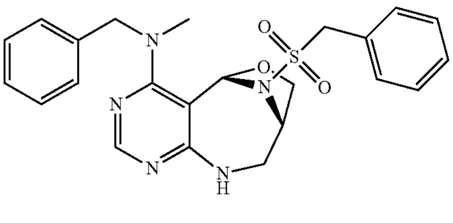
-continued
110
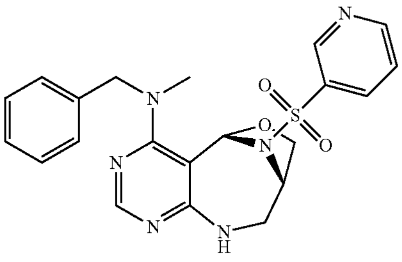
111
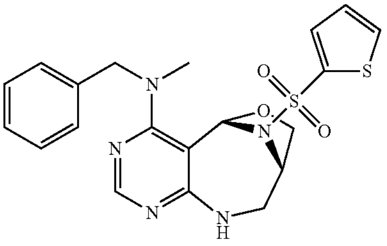
112
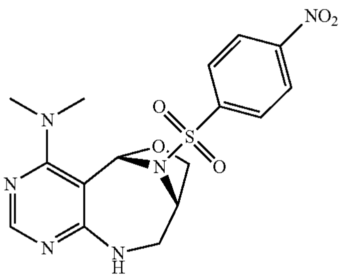
113
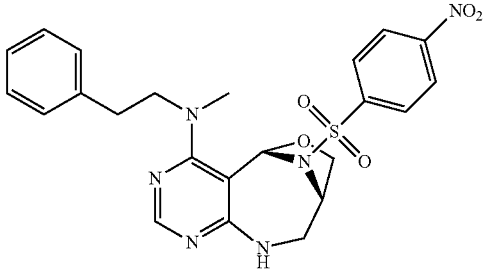
114
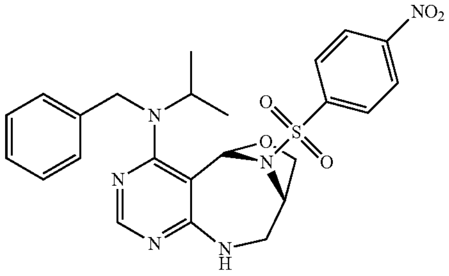
115
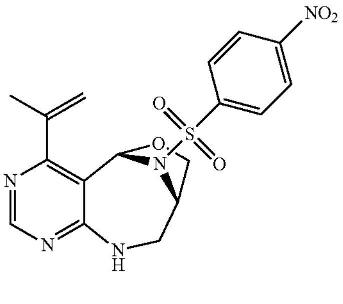

-continued
116
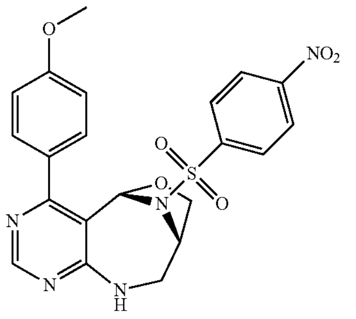
117
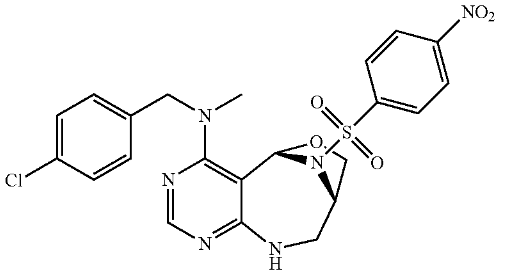
118
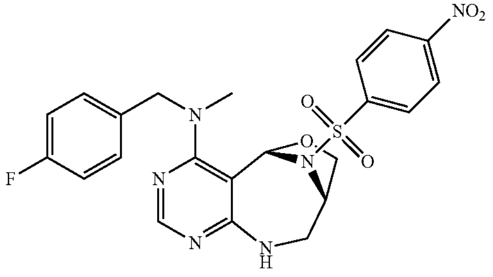
119
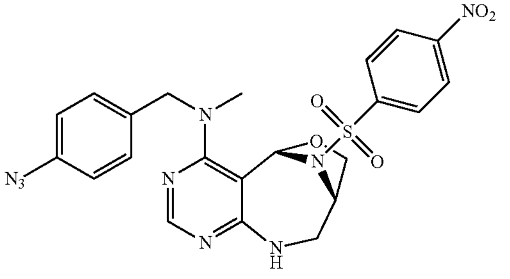
120
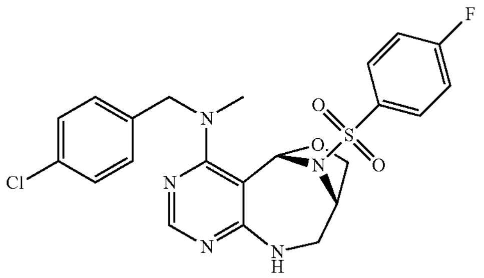
-continued
121
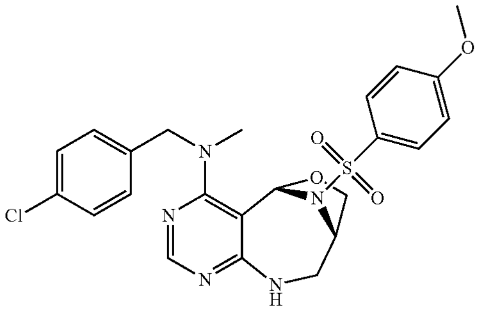
122
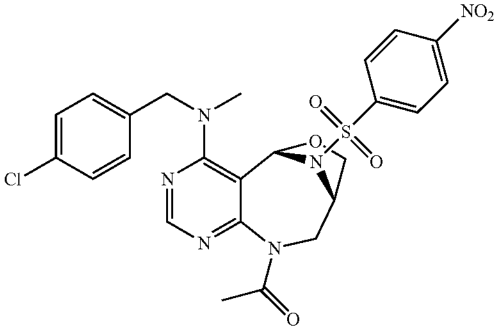
123
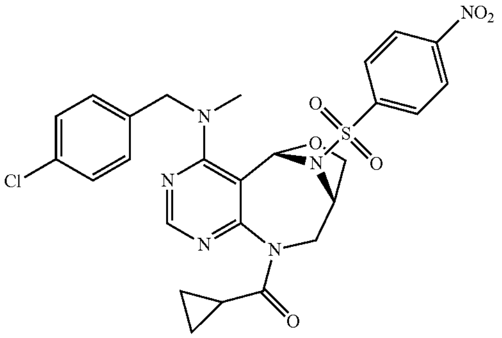
124
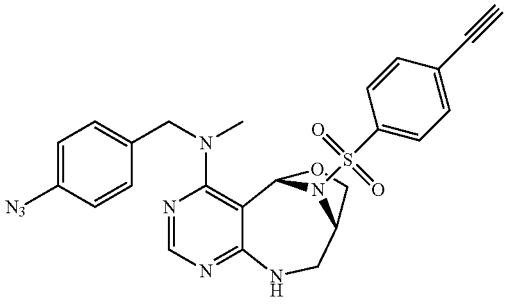
125
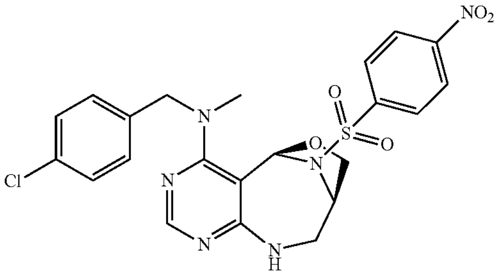

-continued
126
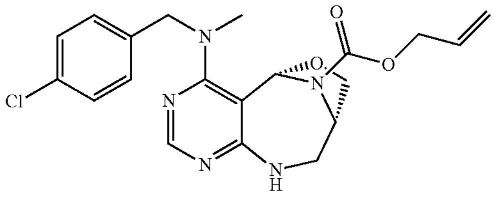
127
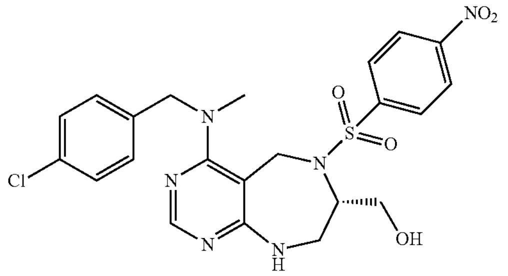
128
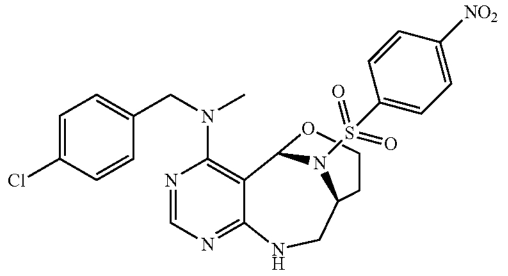
129
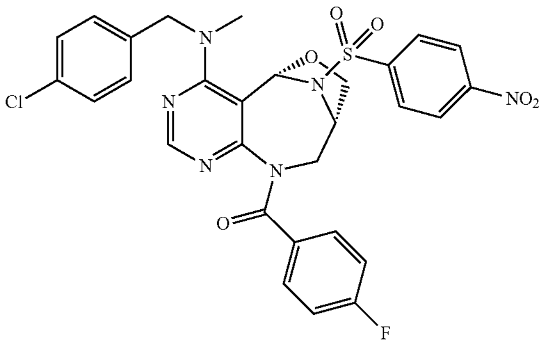
130
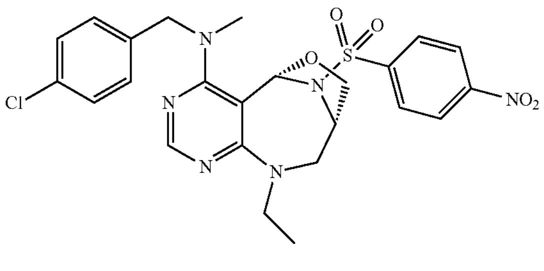
-continued
131
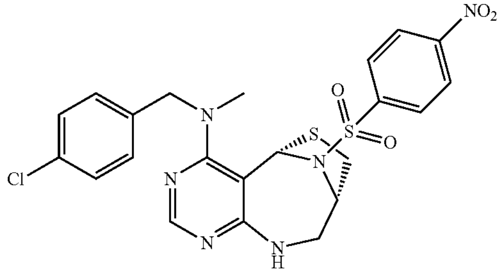
132
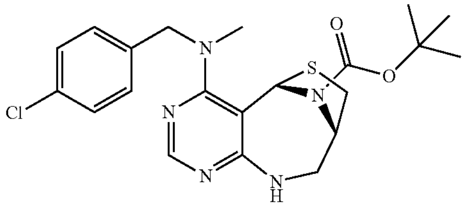
133
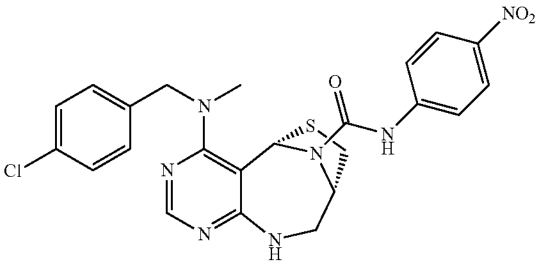
134
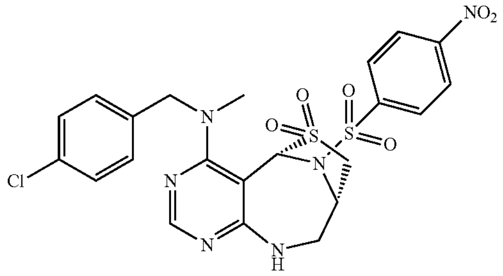
135
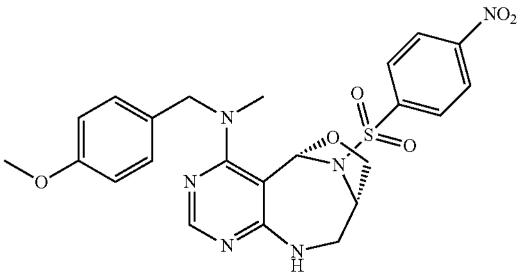

-continued

136

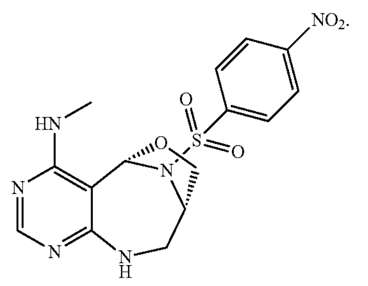

As used herein, the term "pyrimidodiazepine derivative" refers to, but is not limited thereto, a derivative having pyrimidodiazepine as a parent nucleus.

As used herein, the term "pharmaceutically acceptable salt" refers to a salt in a form that can be used pharmaceutically among salts in which cations and anions are bonded by electrostatic attraction, typically, it may be a metal salt, a salt with an organic base, a salt with an inorganic acid, a salt with an organic acid, a salt with a basic or acidic amino acid, and the like. For example, the metal salt may be an alkali metal salt (sodium salt, potassium salt, etc.), an alkaline earth metal salt (calcium salt, magnesium salt, barium salt, etc.), an aluminum salt, and the like. A salt with bases may be a salt with triethylamine, pyridine, picoline, 2,6-lutidine, ethanolamine, diethanolamine, triethanolamine, cyclohexylamine, dicyclohexylamine, N,N-dibenzylethylenediamine, and the like. A salt with inorganic acids may be a salt with hydrochloric acid, hydrobromic acid, nitric acid, sulfuric acid, phosphoric acid, and the like. A salt with organic acids may be a salt with formic acid, acetic acid, trifluoroacetic acid, phthalic acid, fumaric acid, oxalic acid, tartaric acid, maleic acid, citric acid, succinic acid, methanesulfonic acid, benzenesulfonic acid, p-toluenesulfonic acid, and the like. A salt with a basic amino acid may be a salt with arginine, lysine, ornithine, and the like. A salt with an acidic amino acid may be a salt with aspartic acid or glutamic acid, and the like.

For the purpose of the present invention, the pharmaceutically acceptable salt may be interpreted as an acid addition salt or base addition salt of a pyrimidodiazepine derivative suitable for the treatment of patients who are expected to develop tauopathy or have developed the disease, but is not particularly limited thereto.

In the present invention, "halogen" is a fluorine, chlorine, bromine or iodine.

In the present invention, "alkyl" means a saturated hydrocarbon group having straight or branched carbon. For example, but is not limited thereto, it may be methyl, ethyl, propyl, isopropyl, butyl, pentyl, hexyl, 1-methylethyl, 1-methylpropyl, 2-methylpropyl, 1,1-dimethylpropyl or 1,1-dimethylbutyl, and the like.

In the present invention, "$C_1$-$C_{20}$ linear or branched alkyl" means a linear or branched saturated hydrocarbon group having 1 to 20 carbons. For example, but is not limited thereto, it may be methyl, ethyl, propyl, butyl, pentyl, iso-propyl, sec-butyl, tert-butyl, neo-pentyl, sec-pentyl, iso-pentyl, hexyl, heptyl, octyl, nonyl or decyl, and the like.

In the present invention, "C1-C10 linear or branched alkyl" means a linear or branched saturated hydrocarbon group having 1 to 10 carbons. For example, it may be methyl, ethyl, propyl, butyl, pentyl or isopropyl, and the like.

In the present invention, "C1-C10 linear or branched aminoalkyl in which one or more hydrogens are substituted with an amine" means alkyl in which one or more hydrogens in a linear or branched saturated hydrocarbon group having 1 to 10 carbons is substituted with an amine group —NH2, —NHR', —NR'R". Wherein, R' and R" each independently mean an alkyl group. For example, it may be aminomethyl, 2-(dimethylamino)ethyl, 2-(methylethylamino)propyl or 3-(propylamino)butyl, and the like.

In the present invention, "C1-C10 linear or branched alkoxy" means a linear or branched saturated hydrocarbon group having 1 to 10 carbons in which any one or more hydrogens are substituted with a hydroxy group. For example, it may be hydroxymethyl, 2-hydroxyethyl, 1-hydroxypropyl, 3-hydroxy-4-methylpentyl or 3,4-dihydroxyheptyl, and the like.

In the present invention, "C1-C20 linear or branched alkenyl" means a linear or branched hydrocarbon group having 1 to 20 carbons and having an unsaturated double bond. For example, but is not limited thereto, it may be ethylene, propene or 2-methylbut-2-ene, and the like.

In the present invention, "C1-C10 linear or branched alkynyl" means a linear or branched hydrocarbon group having 1 to 10 carbons and having an unsaturated triple bond. For example, but is not limited thereto, it may be acetylene, propane, butine or 3-methylbut-1-tine, and the like.

In the present invention, "C3-C10 cycloalkyl" means a saturated hydrocarbon group of 3 to 10 carbons forming a ring. For example, but is not limited thereto, it may be cyclopropyl, cyclobutyl, cyclopentyl or cyclohexyl, and the like.

In the present invention, "substituted C6-C20 aryl" generically refers to an aryl group in which one or more hydrogens are substituted with another functional group in a residue obtained by removing one hydrogen from the carbon of an aromatic hydrocarbon having 6 to 20 carbons. For example, but is not limited thereto, it may be fluorophenyl, chlorophenyl, toluene, methylphenyl, methoxyphenyl, nitrophenyl, cyanophenyl or aminonaphthyl, and the like.

In the present invention, "unsubstituted C6-C20 aryl" generically refers to a residue obtained by removing one hydrogen from the nucleus of an aromatic hydrocarbon having 6 to 20 carbons. For example, but is not limited thereto, it may be phenyl or naphthyl, and the like.

In the present invention, "arylalkyl in which any one hydrogen of C1-C10 linear or branched alkyl is substituted with substituted or unsubstituted C6-C20 aryl" generically refers to a residue in which a substituted or unsubstituted aryl group having 6 to 20 carbons is substituted with an alkyl group having 1 to 10 carbons. It may be, but is not limited thereto, benzyl, phenylethyl, methylbenzyl (tolubenzyl) or naphthylmethyl (menapthyl), and the like.

In the present invention, "heteroarylalkyl in which any one hydrogen of C1-C5 alkyl is substituted with 6-membered heteroaryl containing one N" generically refers to a residue in which an unsubstituted heteroaryl group having 5 carbons and 1 nitrogen is substituted with an alkyl group having 1 to 5 carbons. It may be, but is not limited thereto, (pyridin-2-yl)methyl, (pyridin-3-yl)ethyl, (pyridin-4-yl) ethyl or 2-(pyridin-4-yl)pentyl, and the like.

In the present invention, "phenoxyalkyl in which any one hydrogen of C1-C10 linear or branched alkyl is substituted with a phenoxy group" generically refers to a residue in which a phenoxy group (—OPh) is substituted with an alkyl group having 1 to 10 carbons. It may be, but is not limited thereto, phenoxymethyl, 2-phenoxyethyl, 2-phenoxypropyl, or 3-methyl-2-phenoxybutyl, and the like.

In the present invention, "5- to 6-membered heterocyclyl containing 1 to 2 N atoms in which any one or more hydrogens are substituted with $C_1$-$C_5$ linear or branched alkyl, or 6- to 10-membered aryl" generically refers to a residue in which a ring compound of 5 to 6 carbons in which 1 to 2 carbons are substituted with nitrogens, and any one or more hydrogens bonded to the carbon or nitrogen are substituted with $C_1$-$C_5$ linear or branched alkyl or 6- to 10-membered aryl. It may be, but is not limited thereto, 2-phenylpiperidin-1-yl, 2-phenylpyrrolidin-1-yl or 4-methyl-2-phenylpiperazin-1-yl, and the like.

The compound according to the present invention inhibits tau aggregation by preventing inhibition of PERK signal activation through specific binding to DNAJC3 and PDIA3, thereby preventing and/or treating various diseases caused by tau aggregation.

Therefore, as another aspect of the present invention, there is provided a tau aggregation inhibitor comprising the compound represented by the Formula 1 or a pharmaceutically acceptable salt thereof, which inhibits tau aggregation by preventing inhibition of PERK signal transduction through binding with PDIA3, DNAJC3, or both.

In another aspect of the present invention, the present invention provides a pharmaceutical composition for preventing or treating tauopathies, comprising the pyrimidodiazepine derivative represented by Formula 1 or a pharmaceutically acceptable salt thereof.

In addition, as another aspect of the present invention, there is provided a method for preventing or treating tauopathies, comprising administering to a subject in need thereof the compound represented by Formula 1 or a pharmaceutically acceptable salt thereof.

In addition, as another aspect of the present invention, there is provided a use of the compound represented by Formula 1 or a pharmaceutically acceptable salt thereof for preventing or treating tauopathies in a subject.

In the present invention, "tauopathy" refers to a neurodegenerative disease in which cranial nerves are damaged by accumulation of denatured tau protein (a family closely related to intracellular microtubule-related proteins) in brain tissue.

In the present invention, examples of tauopathy, but are not limited thereto, it may be any one selected from the group consisting of Alzheimer's disease, frontotemporal dementia, progressive supranuclear palsy, traumatic brain injury, Pick's disease, Chronic traumatic encephalopathy, Argyrophilic grain disease, corticobasal degeneration, Parkinson's disease, Huntingtin's disease, and Amyotrophic lateral sclerosis.

As used herein, the term "prevention" refers to all actions that suppress or delay the onset of the disease by administering a pharmaceutical composition containing the pyrimidodiazepine derivative or a pharmaceutically acceptable salt thereof provided in the present invention to a subject expected to develop tauopathy as an active ingredient.

As used herein, the terms "improvement" and "treatment" refer to all actions that clinically intervene to change the natural process of an individual or cell to be treated, which can be performed during the course of a clinical pathological condition or to prevent it. Desired therapeutic effects include preventing the occurrence or recurrence of the disease, alleviating symptoms, reducing any direct or indirect pathological consequences of the disease, preventing metastasis, reducing the rate of disease progression, alleviating or palliating the disease state, remission or improving prognosis.

For the purpose of the present invention, the treatment can be interpreted to include all actions that improve the course of tauopathy by administering a pharmaceutical composition containing a benzothiazole derivative or a pharmaceutically acceptable salt thereof as an active ingredient to a patient with tauopathy, but is not particularly limited thereto.

Meanwhile, the pharmaceutical composition of the present invention may further include suitable carriers, excipients or diluents commonly used in the preparation of pharmaceutical compositions. A composition containing a pharmaceutically acceptable carrier may be in various oral or parenteral formulations. When formulated, it may be prepared using diluents or excipients such as commonly used fillers, extenders, binders, wetting agents, disintegrants, and surfactants. Solid dosage forms for oral administration may include tablets, pills, powders, granules, capsules, and the like. Such a solid preparation may be prepared by mixing one or more compounds with at least one excipient, for example, starch, calcium carbonate, sucrose or lactose, gelatin, and the like.

In addition to simple excipients, lubricants such as magnesium stearate and talc may also be used. Liquid preparations for oral administration include suspensions, solutions for internal use, emulsions, syrups, and the like. In addition to water and liquid paraffin, which are commonly used simple diluents, various excipients such as wetting agents, sweeteners, aromatics, and preservatives may be included. Formulations for parenteral administration may include sterilized aqueous solutions, non-aqueous solutions, suspensions, emulsions, freeze-dried formulations, and suppositories. Propylene glycol, polyethylene glycol, vegetable oils such as olive oil, and injectable esters such as ethyl oleate may be used as non-aqueous solvents and suspending agents. As a base for suppositories, witepsol, macrogol, tween 61, cacao butter, laurin paper, glycerogelatin, and the like may be used.

In addition, the pharmaceutical composition of the present invention may have any one formulation selected from the group consisting of tablets, pills, powders, granules, capsules, suspensions, internal solutions, emulsions, syrups, sterilized aqueous solutions, non-aqueous solutions, suspensions, emulsions, freeze-dried formulations and suppositories.

The pharmaceutical composition of the present invention is administered in a pharmaceutically effective amount.

As used herein, the term "administration" refers to introducing the pharmaceutical composition of the present invention to a subject by any suitable method, and the route of administration may be administered through various oral or parenteral routes as long as it can reach the target tissue.

The pharmaceutical composition of the present invention can be appropriately administered to a subject according to a conventional method, administration route, and dosage used in the art according to the purpose or necessity. Examples of routes of administration include oral, parenteral, subcutaneous, intraperitoneal, intrapulmonary, and intranasal administration, and parenteral injection includes intramuscular, intravenous, intraarterial, intraperitoneal, or subcutaneous administration.

In addition, an appropriate dosage and frequency of administration may be selected according to a method known in the art, and the amount and frequency of administration of the pharmaceutical composition of the present invention to be actually administered may be appropriately determined by various factors such as the type of symptom to be treated, route of administration, gender, health condition, diet, age and weight of the subject, and severity of the disease.

As used herein, the term "pharmaceutically effective amount" refers to an amount sufficient to suppress or alleviate pain in chemotherapy-induced peripheral neuropathy at a reasonable benefit/risk ratio applicable to medical use, and the effective dose level can be determined according to subject type and severity, age, sex, activity of drug, sensitivity to drug, time of administration, route of administration and excretion rate, duration of treatment, factors including concomitantly used drugs and other factors well known in the medical field. The composition of the present invention may be administered as an individual therapeutic agent or in combination with other therapeutic agents, and may be administered sequentially or simultaneously with conventional therapeutic agents. And it can be single or multiple administrations. It is important to administer the amount that can obtain the maximum effect with the minimum amount without side effects in consideration of all the above factors, and can be easily determined by those skilled in the art.

In addition, as another aspect of the present invention, the present invention provides a method for preventing or treating tauopathies, comprising administering to a subject in need thereof the composition comprising a pyrimidodiadiazepine derivative or a pharmaceutically acceptable salt thereof as an active ingredient.

As used herein, the term "individual" refers to all animals, including humans, who are likely to develop the above-described tauopathy or have the disease. By administering the composition of the present invention to a subject in need thereof, tauopathy can be alleviated or treated.

Hereinafter, a preferred embodiment is presented to aid understanding of the present invention. However, the following examples are provided to more easily understand the present invention, and the content of the present invention is not limited by the following examples.

Example 1: Experimental Method

1-1. Experimental Design

A cell-based phenotypic screen was performed by monitoring tau protein dimerization under ER stress conditions using the HEK293 BiFC-tau Venus cell system. In a preliminary SAR study, the potency of the initial target compound was improved, and the potency of the lead compound obtained (SB1617) was evaluated by immunoblot assay in tau-overexpressing cells (to quantify pathological p-tau and tau levels). In addition, the potential role of the new compound (SB1617) in regulating protein homeostasis was investigated by evaluating tau clearance in bicistronic DsRed-IRES-EGFP-tau cells. In addition, a label-free target identification method based on TS-FITGE was used to identify the cellular target protein of the novel compound (SB1617). In addition, relevant targets were validated through phenotypic experiments (knockdown of candidate targets, PDIA3 and DNAJC3 in tau-overexpressing cell lines), in vitro binding assays and cell-based assays. In addition, the potential mechanism of action of the new compound (SB1617) was explored using cell-based biological methods, and its efficacy was evaluated in vivo using a mouse model of traumatic brain injury.

1-2. Cell Culture

The BiFC-tau stable HEK293 human embryonic kidney cell line was provided by the Korea Institute of Science and Technology(KIST), and was cultured in Dulbecco's Modified Eagle's Medium(DMEM, Gibco) supplemented with 10% fetal bovine serum(FBS, Gibco), 1% penicillin(100 units/mL)/streptomycin(100 μg/mL, Gibco), Fungizone (0.25 μg/mL, Gibco) and Geneticin(100 μg/mL, Gibco). SH-SY5Y human neuroblastoma cells (CRL-226, ATCC) were cultured in DMEM/F12 (Gibco) supplemented with 10% FBS, 1% penicillin/streptomycin and Fungizone. All cells were confirmed to be *Mycoplasma* negative using the EZ-*Mycoplasma* detection kit (DoGenBio) in 37° C. incubator with 5% $CO_2$.

1-3. Cell Line Generation Using Lentiviral Production and Transduction

A lentiviral expression system was used to stably express DsRed_IRES_Tau-EGFP in the HEK293 cell line.

For virus production, HEK293 cells were seeded in 100-mm culture dishes, and were co-transfected with 3 μg of lentiviral transfer plasmid encoding pLenti-DsRed_IRES_MAPT:EGFP(Addgene, #92196), 3 μg of pCMV-VSV-G envelope plasmid(Addgene, #8454), 3 μg of plasmid(Addgene, #12260) using psPAX2 packaging Lipofectamine (ThermoFisher Scientific), pEGFP-Q23(Addgene #40261) and pEGFP-Q74(Addgene #40262). HEK293 cells were infected by adding viral stocks to 6-well cell culture dishes overnight. After infection, cells were selected by adding Geneticin for 7 to 10 days. Cells were then further sorted by double-positive (DsRed and EGFP) gating using a FACS Aria II (BD Bioscience). Stable cell lines were cultured in DMEM supplemented with 10% FBS, 1% penicillin/streptomycin, Fungizone (0.25 μg/mL) and Geneticin (100 μg/mL) and maintained in 37° C. incubator with 5% $CO_2$.

1-4. Plasmid and siRNA transfection

Plasmids pRK5-EGFP-Tau (#46904) and pRK-EGFP-Tau P301L (#46908) were purchased from Addgene. Plasmids pCMV-SOD1-EGFP and pCMV-SOD1 G93A-EGFP were provided by Seoul National University College of Medicine. Plasmids were transfected in HEK293T cells using Lipofectamine and Opti-MEM (Gibco) based on the manufacturer's instructions. Short interfering RNA duplex (siRNA duplex, BIONEER) for PDIA3 and DNAJC3 was used for PDIA3 and DNAJC3 knockdown experiments. siRNA oligonucleotides were transfected in HEK293 cells stably expressing BiFC-tau using Lipofectamine RNAiMAX (ThermoFisher Scientific) and Opti-MEM (Gibco) based on the manufacturer's instructions.

The oligonucleotide sequences for PDIA3 and DNAJC3 are the same as-

```
siPDIA3 #1 sense
5'-CGUCCUUCACAUCUCACUA-3'

antisense
5'-UAGUGAGAUGUGAAGGACG-3'

siPDIA3 #2 sense
5'-GAAAUACCAGGACCAGUUU-3'

antisense
5'-AAACUGGUCCUGGUAUUUC-3'

siDNAJC3 #1 sense
5'-CUGCUAUAGCCUUCCUUGA-3'

antisense
5'-UCAAGGAAGGCUAUAGCAG-3'
```

-continued siDNAJC3 #2 sense
5'-GUGAUGGCUUUUACCUACU-3' antisense
5'-AGUAGGUAAAAGCCAUCAC-3'

1-5. Monitoring of Tau Assembly and Screening of Compounds Using the BiFC-Tau Venus HEK293 Cell Line Phenotype-based screening to monitor tau assembly was performed using BiFC-tau Venus HEK293 cells in a high-throughput manner. Cells were seeded in 384-well plates at a density of $2.8\times10^3$ cells/well in 40 μL medium for 24 hours. Cells were treated with 80 nM thapsigargin (Sigma-Aldrich) in 10 μL medium and then ~3,000 pDOS library compounds (10 μM), including compounds according to the present invention, using a 0.1 μL pinning tool. For knock-down experiments, cells were transfected with 5 or 10 nM siRNA using Lipofectamine RNAiMAX and incubated for 48 hours before thapsigargin treatment. After incubation at 37° C. in a 5% $CO_2$ incubator for 24 hours, nuclei were stained with medium-diluted Hoechst 33342 (2 μg/mL, ThermoFisher) for 20 minutes. Plates were scanned on an INCell Analyzer 2000 (GE Healthcare) at $\lambda_{ex}/\lambda_{em}$=490/525 nm for Venus fluorescence (for the FITC channel) and $\lambda_{ex}/\lambda_{em}$=350/455 nm for nuclei (for the DAPI channel). Bright-field images were taken to confirm cell morphology, and images were analyzed to quantify Venus intensity per cell using developer software (GE Healthcare).

1-6. Flow Cytometry Analysis Using the HEK293 DsRed-IRES-Tau-EGFP Cell Line

HEK293 DsRed-IRES-tau-EGFP cells were either treated with each compound for the indicated times or transfected with siRNA using Lipofectamine RNAiMAX. Cells were trypsinized, suspended in phosphate buffered saline (PBS) and subjected to FACS analysis using Aira II. Data were analyzed to determine the fluorescence intensity ratio of EGFP to DsRed per cell using flowing software 2.5.1. Mean values of GFP and DsRed fluorescence intensities per cell with double positive gating were used for analysis.

1-7. Immunoblotting

Cells were collected and lysed in modified radioimmunoprecipitation assay(RIPA) buffer 50 mM Tris-HCl, pH 7.8, 150 μM NaCl, 1% NP-40, 0.5% deoxycholate, 5 mM NaF, 2 mM $Na_3VO_4$, and 1× Protease Inhibitor Cocktail (Roche). The concentration of total protein in each lysate was then determined using a whole cell assay and Pierce BCA Protein Assay Kit (ThermoFisher Scientific). Centrifugation was performed at 200 g for 10 minutes at 4° C. for measurement. Equal amounts of each lysate were fractionated by PAGE, transferred to a PVDF membrane (Bio-Rad), and blocked with 2% bovine serum albumin (BSA, MP Biomedicals) in Tris Buffered Saline supplemented with Tween20 (TBST, Sigma) for 1 hour at room temperature.

Membranes were probed with protein-specific antibodies overnight at 4° C. The following day, membranes were washed three times in TBST and incubated with 2% BSA in TBST for 1 hour at room temperature with anti-rabbit or anti-mouse horseradish peroxidase secondary antibodies (Cell Signaling Technology). After washing, membranes were exposed to detection reagents (GE Healthcare) and quantified via chemiluminescence (Bio-Rad).

The following antibodies were used as primary antibodies for immunoblot studies:

rabbit anti-ph(T982)-PERK polyclonal antibody (Abcam, ab192591);

rabbit anti-PERK monoclonal antibody (Cell Signaling Technology, 3192);

rabbit anti-EIF2S1 (phospho S51) polyclonal antibody (Abcam, Ab32157);

rabbit anti-ph-eIF2α (Ser51) monoclonal antibody (Cell Signaling Technology, 3597);

mouse anti-eIF2α monoclonal antibody (santa cruz, sc-133132); rabbit anti-ATF4 monoclonal antibody (Cell Signaling Technology, 11815);

mouse anti-CHOP monoclonal antibody (Cell Signaling Technology, 2895); mouse anti-Tau-5 monoclonal antibody (Abcam, ab80579);

mouse anti-Tau-5 monoclonal antibody (Invitrogen, AHB0042);

rabbit anti-Tau (phospho S199) monoclonal antibody (Abcam, ab81268);

rabbit anti-Tau (phospho T231) monoclonal antibody (Abcam, ab151559);

rabbit anti-Tau (phospho S396) monoclonal antibody (Abcam, ab109390);

rabbit anti-DNAJC3 monoclonal antibody (Cell Signaling Technology, 2940);

rabbit anti-ERp57 polyclonal antibody (Abcam, ab10287);

mouse anti-P4HB monoclonal antibody (Abcam, ab2792);

mouse anti-GFP monoclonal antibody (Cell Signaling Technology, 2955);

rabbit anti-SQSTM1/p62 polyclonal antibody (Cell Signaling Technology, 51145);

rabbit anti-LC3B polyclonal antibody (Abcam, ab51520);

rabbit anti-BDNF monoclonal antibody (Abcam, ab108319);

rabbit anti-GAPDH monoclonal antibody (Cell Signaling Technology, 2118).

1-8. TS-FITGE

HEK293 BiFC-tau cells were treated with dimethylsulfoxide (DMSO, 0.1%) and a compound according to the present invention (10 μM) in the presence of thapsigargin (200 nM) for 3 hours. The cell suspension was heated at the indicated temperature range for 3 minutes and then at 25° C. for 3 minutes. The heated cells were washed with PBS and resuspended in lysis buffer A (0.4% NP-40 in PBS supplemented with protease inhibitor cocktail). For cell lysis, cell suspensions were freeze-thawed in liquid nitrogen three times. The cell lysate was washed by centrifugation at 20000 g, 4° C. for 20 minutes. Protein concentration of the soluble fraction was quantified by Pierce BCA protein assay. After precipitating 50 μg of protein with cold acetone, it was centrifuged at 2000° C. and 4° C. for 7 minutes. The residual pellet was resuspended in 10 μl of conjugation buffer (30 mM Tris-HCl at pH 8.6, 30 mM thiourea, 7 M urea and 4% w/v CHAPS). 1 μl of 0.4 mM Cy2-N-hydroxysuccinimide (Cy2-NHS) (for DMSO-treated group), Cy3-NHS (for SB1607-treated group) or Cy5-NHS (for SB1617-treated group) was mixed with the protein and incubated at 4° C. for 45 minutes. Dye-conjugated proteomes were precipitated with cold acetone and resuspended in 50 μl of rehydration buffer (7 M urea, 2 M thiourea, 2% w/v CHAPS, 40 mM DTT and 1% IPG buffer). Equal amounts of DMSO-treated, SB1607-treated and SB1617-treated samples were mixed and then a total of 150 μg (50 μg for each Cy2-, Cy3- and Cy5-labeled) of proteome was loaded onto a 24 cm Immobiline Drystrip gel (GE Healthcare). Isoelectric focusing was performed by Ettan IPGphor 3 (GE Healthcare) followed by polyacrylamide gel electrophoresis (PAGE) using the Ettan DALTsix system (GE Healthcare). Gels were scanned with Typhoon Trio (GE Healthcare). Protein spot locations and fluorescence signals were analyzed with DeCyder 2D software ver. 7.2 (GE Healthcare).

1-9. CETSA

HEK293 BiFC-tau cells were treated with DMSO (0.1%) and a compound according to the present invention (10 μM) in the presence of thapsigargin (200 nM) for 3 hours. The cell suspension was heated at the indicated temperature range for 3 minutes and then at 25° C. for 3 minutes. The heated cells were washed with PBS and resuspended in Lysis Buffer A. For cell lysis, cell suspensions were freeze-thawed in liquid nitrogen three times. The cell lysate was washed by centrifugation at 20000 g, 4° C. for 20 minutes. Equal volumes of washed cell lysate were combined with SDS buffer and subjected to immunoblotting.

1-10. Pull-Down Assay

SH-SY5Y cells were seeded in 6-well plates and then treated with 1 μM thapsigargin and 5 μM SB1624 (probe compound) for 2.5 hours with or without 40 μM SB1617. Cells were exposed to 356 nm UV irradiation for 30 min on ice. After washing with cold PBS, cells were lysed in RIPA buffer and removed by centrifugation at 2000° C. for 15 minutes at 4° C. The protein concentration of the supernatant was determined by Pierce BCA Protein Assay Kit and the protein concentration was adjusted to 1 mg/mL. A click reaction to the proteome using biotin-azide (50 μM, Sigma Aldrich), TBTA (100 μM, Sigma Aldrich), $CuSO_4$ (1 mM, Sigma Aldrich), TCEP (1 mM, Sigma Aldrich) and tBuOH (5%) was performed for 1 hour. Cold acetone was added to the mixture at −20° C. for 20 min for protein precipitation. After centrifugation at 15000 g at 4° C. for 10 min, the pellet was dissolved by sonication in PBS containing 1.2% SDS and diluted with 0.2% sodium dodecylsulfate (SDS) by adding PBS. Samples were incubated with 20 μL streptavidin agarose beads (Sigma Aldrich) while rotating for 3 hours at room temperature. Beads were washed 4 times with PBS containing 0.2% SDS. Proteins were eluted by boiling with 3×SDS sample buffer and analyzed by SDS-PAGE and Western blot.

1-11. Surface Plasmon Resonance Assay

Surface plasmon resonance (SPR) assays were performed using a Biacore T100 instrument (GE Healthcare). The recombinant PDIA3 or DNAJC3 protein was immobilized on the CM5 sensor chip (GE Healthcare) through an amide bond by activating the carboxy group on the CM5 sensor chip with a 1:1 mixture of N-ethyl-N'-(3-dimethylaminopropyl)-carbodiimide and N-hydroxysuccinimide. Protein immobilization reactions were performed in PBS containing 0.005% Tween 20 at pH 4.7 and pH 5.0 for PDIA3 and DNAJC3, respectively. Binding between compounds and proteins was monitored by injecting compounds at various concentrations into PBS (pH 7.3) containing 3% DMSO and 0.005% Tween 20 at 25° C. Data were analyzed to calculate kinetic parameters by fitting sensor grams with a 1:1 binding model using Biacore T100 evaluation software (GE Healthcare).

1-12. PEG Maleimide Modification Assay

Cysteine modification analysis using PEG maleimide was performed according to the paper (P. Kranz, F. Neumann, A. Wolf, F. Classen, M. Pompsch, T. Ocklenburg, J. Baumann, K. Janke, M. Baumann, K. Goepelt, H. Riffkin, E. Metzen, U. Brockmeier, PDI is an essential redox-sensitive activator of PERK during the unfolded protein response (UPR). *Cell Death Dis.* 8, e2986 (2017)).

After compound treatment, BiFC-tau HEK293 cells were washed with cold PBS, incubated with 20 mM N-ethylmaleimide (NEM, Sigma Aldrich) in PBS for 20 minutes on ice to alkylate the reduced form of cysteine, and after washing with cold PBS, the cells were lysed in RIPA buffer. For whole cell analysis, the lysate was centrifuged at 200 g for 5 min at 4° C. to remove insoluble material. Protein concentration in the supernatant was analyzed by Pierce BCA Protein Assay Kit. Equal amounts of each lysate were treated with 12 mM tris(2-carboxyethyl)phosphine (TCEP, Sigma Aldrich) for 20 minutes at room temperature to reduce the form of oxidized PDI. Lysates were incubated with 15 mM methoxy polyethylene glycol 5000 maleimide (mPEG-mal5000, Sigma Aldrich) for 1 hour at room temperature. After adding SDS sample buffer to the lysates and brief vortex, the SDS samples were directly used for SDS-PAGE and Western blot.

1-13. RNA Extraction and Quantitative Real-Time PCR (qRT-PCR)

To analyze the level of autophagy-related genes, SH-SY5Y cells were treated with 1 μM thapsigargin for 8 h in the presence or absence of 5 μM SB1617. Total RNA was extracted using the RNeasy kit (Qiagen) according to the manufacturer's instructions. RNA was quantified using NanoVue (GE Healthcare) and cDNA was prepared with AccuPower CycleScript RT PreMix dT20 (Bioneer) according to the manufacturer's instructions. Quantitative RT-polymerase chain reaction (qRT-PCR) experiments were performed using KAPA SYBR FAST ABI Prism qPCR Master Mix (KAPA Biosystems). Data were analyzed with the comparative Ct method and normalized to housekeeping genes.

1-14. Laboratory Animal

CD-1 (ICR) male mice (2-3 months old, 25-35 g body weight; DBL, Korea) were used in the TBI study. Mice were maintained in a controlled environment (22±2° C., 55±5% humidity, 12 h light/dark cycle with lights on at 8:00 am) and received a standard diet by Purina, Korea. All mice were fed water and food ad libitum. In order to avoid and minimize transport-related stress, experiments were initiated after a period of one week following transport to allow the animals to acclimatize to environmental conditions. Animal care protocols and experimental procedures were approved by the Animal Research and Research Committee of Hallym University (Protocol #Hallym 2018-82), in accordance with the guidelines of the National Institutes of Health.

1-15. Pharmacokinetics Test

After intravenous or intraperitoneal administration (5 mg/kg, 3.3 mL/kg) of the compound (SB1617, 5% DMSO/35% PEG-400/65% DW) according to the present invention to CD-1 (ICR) male mice (7 weeks old, KOATECH, Korea), blood was collected at designated time points from the orbital venous plexus. The concentration of the compound (SB1617) according to the present invention was examined from the plasma samples using an LC-MS/MS analyzer (Agilent 1200, 4000 Qtrap). Pharmacokinetic parameters were obtained from plasma concentration-time plots using WinNonlin software (Pharsight, USA).

1-16. Blood-Brain Barrier Penetration Test

After intraperitoneal administration (5 mg/kg, 3.3 mL/kg) of the compound (SB1617, 5% DMSO/35% PEG-400/65% DW) according to the present invention to CD-1 (ICR) male mice (7 weeks old, KOATECH, Korea), blood samples were collected using heparinized tubes at designated time points (0.5 and 3 hours) in the orbital venous plexus, mice were sacrificed, and brain tissues were harvested. Plasma and brain homogenate samples were analyzed with an LC-MS/MS analyzer (Agilent 1260, Agilent 6460). The proportion of the compound according to the invention (SB1617) in brain and plasma was calculated.

1-17. Experimental Controlled Cortical Impact Model for Traumatic Brain Injury (TBI)

An experimental controlled cortical impact (CCI) model for TBI was performed as follows. Using an isoflurane vaporizer (VetEquip), the mouse was deeply anesthetized with isoflurane inhaled at 3% in a mixture of 70:30 nitrous oxide and oxygen, and placed in a stereotaxic apparatus. Next, it was maintained with 1 to 1.5% isoflurane. An approximately 4 mm incision was made in the right hemisphere using a hand-held drill (midline 2 mm, bregma 1 mm). A controlled cortical impact device (Leica Impact One, Leica Biosystems) was used to accelerate an impact device equipped with a 2 mm flat-tip at a speed of 5 m/sec to a depth of 1.4 mm. All animal models were maintained at a core temperature of 36-37.5° C. using an isothermal blanket control device (Harvard Bioscience) during and after surgery until outpatient. Traumatic brain injury animal models were randomly generated according to an online randomization tool (randomizer.org). Sham-operated groups performed only craniotomy.

1-18. Compound Dosing Test for TBI

To investigate the neuroprotective effect of the compound according to the present invention on brain damage after TBI, the compound according to the present invention (SB1617) was intraperitoneally administered twice a day at a dose of 5 mg/kg (5% DMSO/50% PEG-400/45% DW). Control mice were intraperitoneally administered with the same volume of vehicle.

1-19. Tissue Preparation

Mice were deeply anesthetized by intraperitoneal administration of a mixture of urethane (1.5 g/kg) in saline (0.9% NaCl) at 0.01 mL/g per body weight. The effect of anesthesia was assessed using a toe pinch. Subsequently, saline was perfused into the heart of the mouse, and PBS was mixed with 4% paraformaldehyde and then perfused. Brains were fixed in 4% paraformaldehyde for 1 h and immersed in 30% sucrose for cryoprotection. Then, whole brains were frozen and coronary artery sections were formed on a cryostat microtome (CM1850, Leica) with a thickness of 30 μm.

1-20. Immunohistochemistry

Sections were immersed in 1.2% $H_2O_2$ for 20 minutes at room temperature to inhibit endogenous peroxidase activity. After washing in PBS, sections were incubated overnight with a mouse monoclonal anti-NeuN antibody (1:500 dilution, Millipore) in PBS containing 0.3% Triton X-100 at 4° C. to assess neuronal loss after TBI. After washing with PBS, sections were incubated in biotinylated anti-mouse IgG (1:250 dilution, Vector) at room temperature for 2 hours after TBI to detect NeuN antibody and biotinylated anti-rat IgG (1:250 dilution, Vector) to examine the degree of leakage of endogenous immunoglobulin G. Then, the sections were immersed in an avidin-biotin-peroxidase complex (Vector) for 2 hours at room temperature. Between incubations, sections were washed with PBS. The immune response was visualized with 3,3'-diaminobenzidine (Sigma-Aldrich) in 0.01 M PBS containing 0.015% $H_2O_2$, and sections were mounted on gelatin-coated slides. Immunoreactivity was observed under an Olympus IX70 inverted microscope.

1-21. Immunofluorescence Assay

Immunofluorescence labeling was performed according to a conventionally known general immunostaining procedure. Sections were immersed in 1.2% $H_2O_2$ for 15 minutes at room temperature to inhibit endogenous peroxidase activity. After washing with PBS, the sections were incubated with each specific type of polyclonal or monoclonal primary antibody with PBS containing 0.3% Triton X-100 overnight at 4° C.

The primary antibodies used in this test are the same as follows:

- mouse monoclonal anti-4-hydroxynonenal (4-HNE; diluted 1:500; Alpha Diagnostic International),
- mouse monoclonal anti-Tau (Tau5; diluted 1:500; Abcam),
- mouse monoclonal anti-phospho Tau (Ser202, Thr205; AT8; diluted 1:200; Invitrogen),
- mouse monoclonal anti-PDI (diluted 1:100; Abcam),
- rabbit polyclonal anti-ERp57 (diluted 1:100; Abcam), and
- goat polyclonal anti-Iba-1 antibody (diluted 1:500; Abcam).

After washing with PBS, fluorescent-conjugated secondary antibodies (1:250 dilution, Invitrogen) were applied to the sections. Sections were counterstained with 4,6-diamidino-2-phenylindole (DAPI, 1:1000 dilution; Invitrogen). Fluorescence-stained sections were mounted on gelatin-coated slides and coverslipped with DPX [Sigma-Aldrich]. Sections were photographed using a confocal microscope (LSM 710; Carl Zeiss).

1-22. IHC/IF Data Quantification

To count NeuN-positive cells, every sixth section was collected posterior to bregma from 1.2 to 2.1 mm at 180 μm intervals. Five coronal sections from each mouse were analyzed using a microscope with a 20×objective. These sections were then coded and provided to a blinded experimenter to count total NeuN-positive cells in hippocampal CA1 and cortex from hippocampal hemispheres. Data were expressed as the average number of NeuN-positive cells per area. To quantify the PDI-, ERp57-, Tau5-, AT8-, and 4HNE-immunofluorescence intensities, five coronal sections were evaluated by a blinded experimenter using ImageJ (National Institute of Health). Images were loaded into ImageJ and changed to 8-bit via the menu options (Image/Color/Split Channels). Images were binarized, menu options (Analyze/Measure) selected, and each immunofluorescence signal was plotted as the mean gray value. To analyze microglia activation, 5 coronal sections from each mouse were evaluated for scoring. Microglia activation criteria were established based on the number and intensity of Iba-1 immunoreactive cells and their morphology according to a method modified from the protocol described above.

The number of Iba-1 immunoreactive cells with continuous processes per 200 $\mu m^2$ was manually counted using images at higher magnification (30×objective) according to the following criteria:

- 0, no cells with continuous stained processes;
- 1, 1 to 9 cells with continuous processes;
- 2, 10-20 cells with continuous processes;
- 3, >20 Cells with continuous processes.

The morphology of Iba-1 immunoreactive cells was analyzed according to the following criteria:

- 0, 0% activated morphology (amoeboid morphology with enlarged soma and thick processes);
- 1, 1-45% of Iba-1 immunoreactive cells are activated;
- 2, 45-90% of Iba-1 immunoreactive cells are activated form;
- 3, >90% of Iba-1 immunoreactive cells are activated form.

The intensity of Iba-1 immunoreactive cells was analyzed according to the following criteria:

- 0, no expression;
- 1, weak expression;
- 2, mean expression;
- 3, strong expression.

The total score ranges from 0 to 9 by adding the scores of the above three items.

1-23. Neurological Deficit Assessment

In order to evaluate whether the neurological deficit induced by TBI was attenuated by administration of the compound (SB1617) according to the present invention, neurological function was evaluated using a neurological severity score (NSS). Assessments were performed every 1, 12, 24, 48, and 72 hours, and 7 days after TBI induction or sham surgery. The NSS evaluated the functional neurological status of mice based on reflex behavior and motor performance (muscle status, abnormal movements), and behavioral tasks such as beam walking, beam balance, and spontaneous locomotion. Assessment was performed on a scale of 0 to 10 (0=normal function to 10=maximum loss). One point is awarded for failure to perform a specific task or no reflex action tested. Thus, higher scores mean more serious injuries.

1-24. Pole Climbing Test

A pole climbing test was performed to analyze motor coordination of mice. The mouse was placed on the vertical end of the pole (60 cm above the ground). Then, the time it took to turn the body completely downward (turning time) and the time all four feet touched the floor (finishing time) were recorded. The maximum test time is 60 seconds. At certain time points, each mouse was tested 3 times and then the average was calculated and used for statistical analysis.

1-25. Statistical Analysis

All statistical analyzes were performed using GraphPad Prism software (GraphPad, San Diego, CA, USA).

Example 2: Synthesis Reagent

[Compound 1]

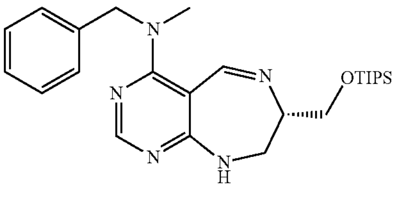

The synthesis and characterization of compound 1 are the same as previously reported [Reference: Kim, J. et al. Diversity-Oriented Synthetic Strategy for Developing Chemical Modulator of Protein-Protein Interaction. *Nat. Commun.* 7, 13196 (2016)].

[Compound 2]

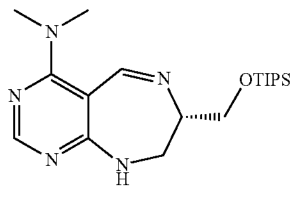

light yellow solid; $R_f$=0.15 (DCM/MeOH=20:1); 62% overall yield;

$^1$H NMR (400 MHz, $CDCl_3$): 8.04 (br d, J=2.0 Hz, 1H), 7.98 (s, 1H), 6.68 (br s, 1H), 4.16 (dd, J=9.8, 4.7 Hz, 1H), 3.83 (m, 2H), 3.64 (t, J=10.0 Hz, 1H), 3.28 (ddd, J=12.8, 6.9, 2.2 Hz, 1H), 3.09 (S, 6H), 1.10 (m, 21H);

$^{13}$C NMR (100 MHz, $CDCl_3$): 167.4, 162.2, 157.7, 157.1, 92.4, 65.2, 64.5, 47.4, 42.0, 18.1, 12.0;

HRMS(ESI+): Calcd for $C_{19}H_{36}N_5OSi^+$ $[M+H]^+$ 378.2684, found 378.2682, Δppm −0.53; mp: 76-78° C.

[Compound 3]

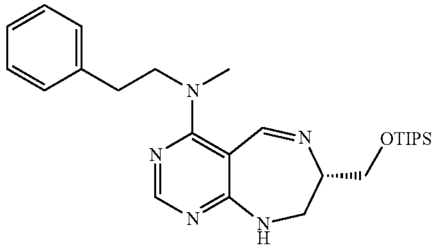

yellow oil; $R_f$=0.36 (DCM/MeOH=20:1); 61% overall yield;

$^1$H NMR (400 MHz, $CDCl_3$): 8.01 (s, 1H), 7.96 (s, 1H), 7.27 (m, 2H), 7.20 (m, 3H), 6.74 (br s, 1H), 4.18 (dd, J=9.8, 4.3 Hz, 1H), 3.89 (m, 3H), 3.67 (t, J=10.2 Hz, 1H), 3.60 (m, 1H), 3.30 (dd, J=11.0, 7.4 Hz, 1H), 3.09 (s, 3H), 2.96 (m, 2H), 1.13 (m, 21H);

$^{13}$C NMR (100 MHz, $CDCl_3$): 167.1, 162.1, 157.8, 157.0, 139.0, 128.8, 128.6, 126.5, 92.7, 65.2, 64.4, 54.8, 47.5, 40.8, 34.1, 18.1, 12.0;

HRMS(ESI+): Calcd for $C_{26}H_{42}N_5OSi^+$ $[M+H]^+$ 468.3153, found 468.3151, Δppm −0.43;

[Compound 4]

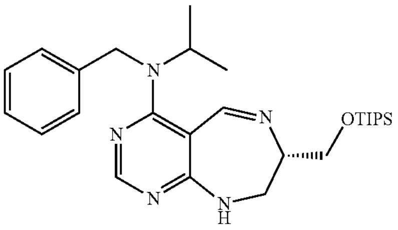

yellow oil; $R_f$=0.42 (DCM/MeOH=20:1); 57% overall yield;

$^1$H NMR (400 MHz, $CDCl_3$): 8.24 (d, J=2.0 Hz, 1H), 8.00 (s, 1H), 7.27-7.15 (m, 5H), 6.40 (br s, 1H), 4.85 (d, J=15.3 Hz, 1H), 4.38 (d, J=15.3 Hz, 1H), 4.19 (dd, J=9.6, 4.5 Hz, 1H), 4.04 (m, 1H), 3.78 (m, 2H), 3.65 (t, J=9.8 Hz, 1H), 3.25 (ddd, J=12.9, 7.0, 2.3 Hz, 1H), 1.37 (d, J=6.3 Hz, 3H), 1.24 (d, J=6.7 Hz, 3H), 1.12 (m, 21H);

$^{13}$C NMR (100 MHz, $CDCl_3$): 168.1, 162.3, 157.2, 157.1, 139.8, 128.3, 127.6, 126.7, 96.4, 65.2, 64.8, 56.7, 47.2, 45.9, 21.2, 20.7, 18.1, 12.0;

HRMS(ESI+): Calcd for $C_{27}H_{44}N_5OSi^+$ $[M+H]^+$ 482.3310, found 482.3313, Δppm +0.62;

[Compound 5]

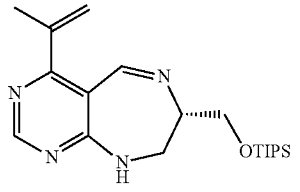

The synthesis and characterization of compound 5 are the same as previously reported [Reference: J. Kim, J. Jung, J. Koo, W. Cho, W. S. Lee, C. Kim, W. Park, S. B. Park, Diversity-oriented synthetic strategy for developing a chemical modulator of protein-protein interaction. *Nat. Commun.* 7, 13196 (2016)].

[Compound 6]

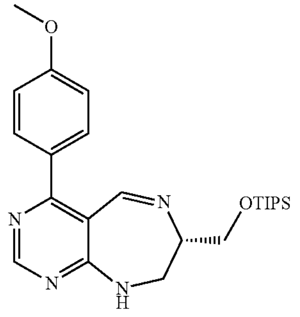

yellow oil; $R_f$=0.5 (DCM/MeOH=20:1); 61% overall yield;

$^{1}$H NMR (500 MHz, $CDCl_3$): 8.52 (s, 1H), 8.27 (s, 1H), 7.58 (d, J=8.3 Hz, 2H), 7.35 (br d, J=5.4 Hz, 1H), 7.01 (d, J=8.3 Hz, 2H), 4.32 (dd, J=9.5, 4.6 Hz, 1H), 4.01 (dd, J=12.7, 6.4 Hz, 1H), 3.95 (br s, 1H), 3.88 (s, 3H), 3.76 (t, J=10.3 Hz, 1H), 3.28 (dd, J=12.7, 7.3 Hz, 1H), 1.17 (m, 21H);

$^{13}$C NMR (100 MHz, $CDCl_3$): 168.9, 161.3, 161.1, 159.0, 158.1, 131.9, 129.7, 113.9, 107.2, 64.94, 64.92, 55.5, 47.9, 18.08, 18.07, 12.0;

HRMS(ESI+): Calcd for $C_{24}H_{37}N_4O_2Si^+$ $[M+H]^+$ 441.2680, found 441.2679, Δppm −0.22.

[Compound 7]

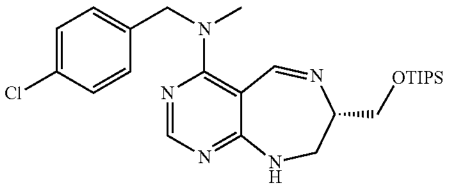

light yellow oil; $R_f$=0.39 (DCM/MeOH=20:1); 73% overall yield;

$^{1}$H NMR (400 MHz, $CDCl_3$): 8.15 (s, 1H), 8.05 (s, 1H), 7.30 (d, J=8.0 Hz, 2H), 7.23 (d, J=8.0 Hz, 2H), 6.86 (br s, 1H), 4.75, 4.68 (ABq, $J_{AB}$=15.6 Hz, 2H), 4.18 (dd, J=9.8, 4.3 Hz, 1H), 3.87 (m, 2H), 3.66 (t, J=10.0 Hz, 1H), 3.33 (dd, J=11.0, 7.4 Hz, 1H), 3.02 (s, 3H), 1.12 (m, 21H);

$^{13}$C NMR (100 MHz, $CDCl_3$): 167.3, 162.5, 157.2, 157.1, 136.0, 133.3, 129.2, 128.9, 92.8, 65.2, 64.6, 55.8, 47.3, 40.4, 18.1, 12.0;

HRMS(ESI+): Calcd for $C_{25}H_{39}ClN_5OSi^+$ $[M+H]^+$ 488.2607, found 488.2608, Δppm +0.20.

[Compound 8]

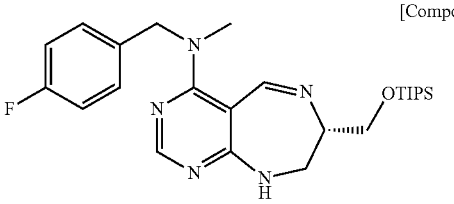

yellow oil; $R_f$=0.35 (DCM/MeOH=20:1); 76% overall yield;

$^{1}$H NMR (500 MHz, $CDCl_3$): 8.12 (d, J=2.4 Hz, 1H), 8.03 (s, 1H), 7.23 (m, 2H), 6.99 (m, 2H), 6.86 (d, J=2.9 Hz, 1H), 4.73, 4.66 (ABq, $J_{AB}$=12.2 Hz, 2H), 4.16 (dd, J=9.8, 4.9 Hz, 1H), 3.86 (m, 2H), 3.64 (t, J=10.0 Hz, 1H), 3.31 (ddd, J=13.0, 7.1, 2.9 Hz, 1H), 2.99 (s, 3H), 1.09 (m, 21H);

$^{13}$C NMR (100 MHz, $CDCl_3$): 167.4, 162.5, 162.3 (d, $^{1}J_{c,f}$=244.4 Hz), 157.19, 157.17, 133.1 (d, $^{4}J_{c,f}$=3.0 Hz), 129.5 (d, $^{3}J_{c,f}$=7.6 Hz), 115.6 (d, $^{2}J_{c,f}$=21.2 Hz), 92.8, 65.2, 64.6, 55.7, 47.3, 40.2, 18.1, 12.0;

HRMS(ESI+): Calcd for $C_{25}H_{39}FN_5OSi^+$ $[M+H]^+$ 472.2902, found 472.2904, Δppm +0.42.

[Compound 9]

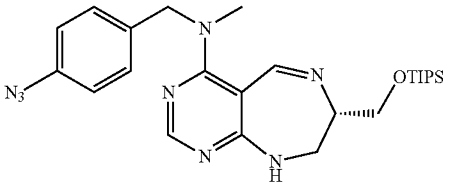

yellow oil; $R_f$=0.35 (DCM/MeOH=20:1); 67% overall yield;

$^{1}$H NMR (400 MHz, $CDCl_3$): 8.14 (s, 1H), 8.05 (s, 1H), 7.27 (d, J=8.2 Hz, 2H), 6.99 (d, J=8.2 Hz, 2H), 6.80 (br s, 1H), 4.76, 4.68 (ABq, $J_{AB}$=15.4 Hz, 2H), 4.18 (dd, J=9.8, 4.3 Hz, 1H), 3.87 (m, 2H), 3.66 (t, J=10.0 Hz, 1H), 3.33 (m, 1H), 3.02 (s, 3H), 1.16 (m, 21H);

$^{13}$C NMR (100 MHz, $CDCl_3$): 167.3, 162.4, 157.2, 157.1, 139.3, 134.2, 129.3, 119.3, 92.8, 65.1, 64.5, 55.9, 47.3, 40.2, 18.1, 12.0; HRMS(ESI+):

Calcd for $C_{25}H_{39}N_8OSi^+$ $[M+H]^+$ 495.3011, found 495.3011.

[Compound 10]

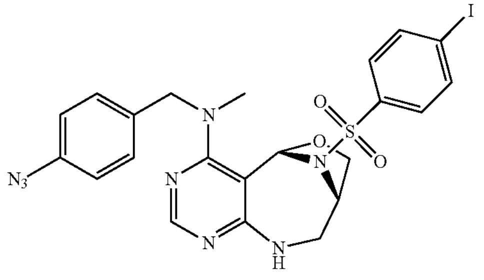

pale yellow; $R_f$=0.45 (EtOAc); 73.0 mg, 61% overall yield;

$^1$H NMR (500 MHz, $CDCl_3$): 8.12 (s, 1H), 7.79 (d, J=8.3 Hz, 2H), 7.36 (d, J=8.3 Hz, 2H), 7.28 (d, J=8.3 Hz, 2H), 7.07 (d, J=8.3 Hz, 2H), 6.62 (s, 1H), 5.90 (br d, J=3.9 Hz, 1H), 4.66, 4.62 (ABq, $J_{AB}$=16.8 Hz, 2H), 4.49 (br s, 1H), 3.81 (d, J=6.8 Hz, 1H), 3.56 (d, J=13.0 Hz, 1H), 3.43 (dt, J=13.6, 5.0 Hz, 1H), 3.06 (t, J=6.8 Hz, 1H), 2.97 (s, 3H);

$^{13}$C NMR (100 MHz, $CDCl_3$): 166.3, 163.5, 156.2, 139.2, 138.7, 137.7, 135.0, 129.2, 129.0, 119.4, 103.4, 101.6, 87.7, 66.9, 58.0, 56.4, 48.7, 40.3;

IR (neat) $\nu_{max}$: 2969, 2107, 1736, 1567, 1351, 1166, 733 $cm^{-1}$;

HRMS(ESI+): Calcd for $C_{22}H_{22}IN_8O_3S^+$ [M+H]$^+$ 605.0575, found 605.0577, Δppm +0.33; mp: 98-100° C.

Example 3: Synthesis of Pyrimidodiazepine Derivatives

3-1. Synthesis of Compound 101 (compound SB1601)

Compound 101 (SB1601), a pyrimidodiazepine derivative according to the present invention, was synthesized according to the following Reaction Formula 1:

[Reaction Formula 1]

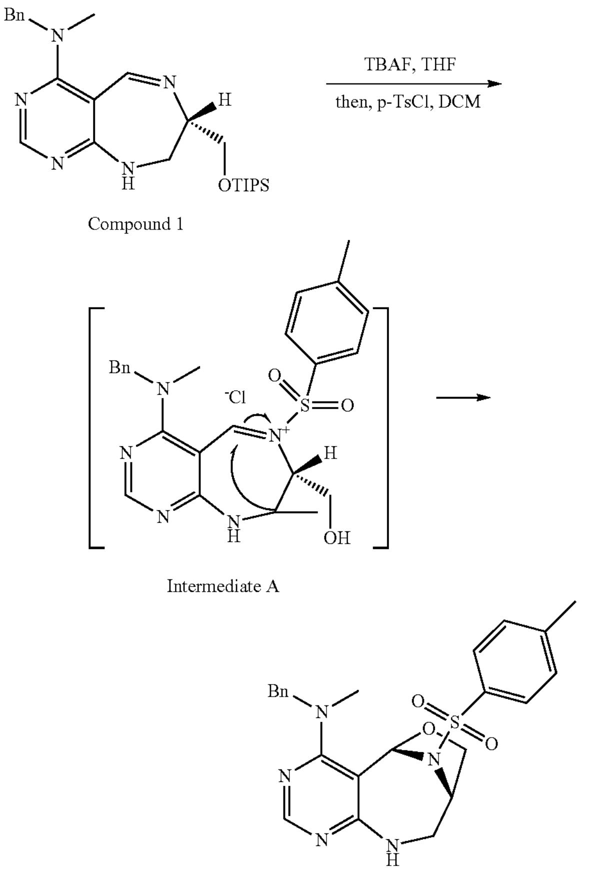

Compound 1

Intermediate A

SB1601

A solution of tetra-n-butylammonium fluoride (1.0 M solution in TBAF, THF, 0.257 ml, 0.257 mmol) was added to a solution of compound 1 (90.0 mg, 0.198 mmol) mixed in tetrahydrofuran (THF, 4 ml), and the mixture was stirred at room temperature (rt). After completion of the reaction, the reaction mixture was quenched with saturated $NaHCO_3$ (aq). The product was extracted twice with dichloromethane (DCM), dried over anhydrous $Na_2SO_4$ (s), filtered and concentrated in vacuo.

To a solution of the crude product in 4 ml of DCM was added p-toluenesulfonyl chloride (p-TsCl, 49.1 mg, 0.257 mmol) and the mixture was stirred at room temperature. After completion of the reaction indicated by TLC, the solvent was removed under reduced pressure and the residue was purified by silica-gel flash column chromatography to obtain the desired product SB1 601 (59.9 mg, 67% overall yield) as a white solid.

Compound 101: SB1601

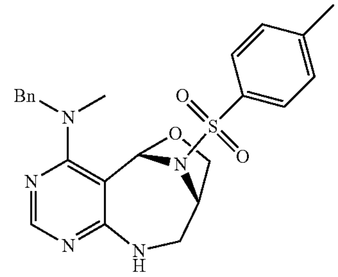

$R_f$=0.39 (EtOAc);

$^1$H NMR (500 MHz, $CDCl_3$): 8.12 (s, 1H), 7.44-7.32 (m, 7H), 7.18 (d, J=7.8 Hz, 2H), 6.62 (s, 1H), 5.71 (br d, J=4.9 Hz, 1H), 4.73, 4.69 (ABq, $J_{AB}$=16.5 Hz, 2H), 4.49 (br s, 1H), 3.75 (d, J=6.8 Hz, 1H), 3.56 (d, J=13.2 Hz, 1H), 3.40 (dt, J=13.2, 4.9 Hz, 1H), 3.00 (s, 3H), 2.95 (t, J=6.8 Hz, 1H), 2.39 (s, 3H);

$^{13}$C NMR (100 MHz, $CDCl_3$): 166.3, 163.5, 156.0, 144.7, 138.2, 134.9, 130.0, 128.8, 127.8, 127.7, 127.3, 103.5, 87.7, 66.8, 58.6, 56.4, 48.8, 40.0, 21.7;

IR (neat) $\nu_{max}$: 3249, 1737, 1559, 1336, 1166, 678 $cm^{-1}$;

HRMS(ESI+): Calcd for $C_{23}H_{26}N_5O_3S^+$ [M+H]$^+$ 452.1751, found 452.1753, Δppm +0.44; mp: 150-152° C.

3-2. Synthesis of Compound 102 (SB1602)

SB1 602 was synthesized according to the synthesis procedure of SB1 601 of Example 3-1 using 4-methoxybenzenesulfonyl chloride instead of p-toluenesulfonyl chloride.

Compound 102: SB1602

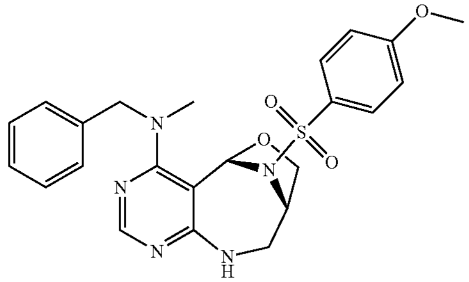

white solid; $R_f$=0.30 (EtOAc); 65.7 mg, 71% overall yield;

$^1$H NMR (500 MHz, $CDCl_3$): 8.11 (s, 1H), 7.43-7.37 (m, 6H), 7.32 (m, 1H), 6.83 (m, 2H), 6.61 (s, 1H), 5.93 (br d, J=5.4 Hz, 1H), 4.73, 4.67 (ABq, $J_{AB}$=16.3 Hz, 2H), 4.46 (br t, J=4.9 Hz, 1H), 3.82 (s, 3H), 3.75 (dd, J=7.3, 2.0 Hz, 1H), 3.55 (d, J=13.2 Hz, 1H), 3.39 (dt, J=13.3, 5.1Hz, 1H), 2.99 (s, 3H), 2.96 (t, J=7.1Hz, 1H);

$^{13}$C NMR (100 MHz, $CDCl_3$): 166.2, 163.6, 163.5, 155.9, 138.2, 129.9, 129.3, 128.7, 127.6, 127.2, 114.5, 103.3, 87.8, 66.8, 58.6, 56.3, 55.7, 48.7, 40.0;

IR (neat) $v_{max}$: 3388, 2952, 1739, 1572, 1533, 1357, 1159, 673 $cm^{-1}$;

HRMS(ESI+): Calcd for $C_{23}H_{26}N_5O_4S^+$ [M+H]$^+$ 468.1700, found 468.1703, Δppm +0.64; mp: 121-123° C.

3-3. Synthesis of Compound 10$^3$ (SB1603)

SB1603 was synthesized according to the synthesis procedure of SB1601 of Example 3-1 using 2-nitrobenzenesulfonyl chloride instead of p-toluenesulfonyl chloride.

Compound 103: SB1603

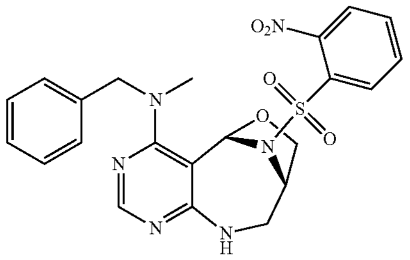

yellow solid; $R_f$=0.30 (EtOAc); 55.4 mg, 58% overall yield;

$^1$H NMR (400 MHz, $CDCl_3$): 8.09 (s, 1H), 7.62 (m, 1H), 7.52 (d, J=8.2 Hz, 2H), 7.45 (m, 1H), 7.37 (m, 2H), 7.31 (m, 3H), 6.74 (s, 1H), 6.06 (br s, 1H), 4.88 (br s, 1H), 4.60 (s, 2H), 3.99 (d, J=7.4 Hz, 1H), 3.58-3.45 (m, 3H), 2.91 (s, 3H);

$^{13}$C NMR (100 MHz, $CDCl_3$): 166.4, 163.9, 156.1, 148.2, 137.9, 134.5, 132.0, 131.7, 130.7, 128.7, 127.8, 127.4, 124.2, 102.0, 87.9, 68.3, 58.1, 56.7, 48.1, 40.0;

IR (neat) $v_{max}$: 2912, 1540, 1353, 1169, 738, 699 $cm^{-1}$;

HRMS(ESI+): Calcd for $C_{22}H_{23}N_6O_5S^+$ [M+H]$^+$ 483.1445, found 483.1443, Δppm −0.41; mp: 80-82° C.

3-4. Synthesis of Compound 104 (SB1604)

The synthesis and characterization of SB1604 are the same as previously reported [Reference: Kim, J. et al. Diversity-Oriented Synthetic Strategy for Developing Chemical Modulator of Protein-Protein Interaction. *Nat. Commun.* 7, 13196 (2016)].

Compound 104: SB1604

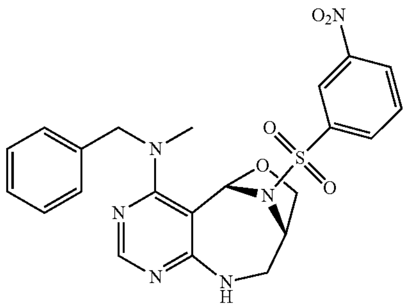

3-5. Synthesis of Compound 105 (SB1605)

SB1605 was synthesized according to the synthesis procedure of SB1601 of Example 3-1 using 4-nitrobenzenesulfonyl chloride instead of p-toluenesulfonyl chloride.

Compound 105: SB1605

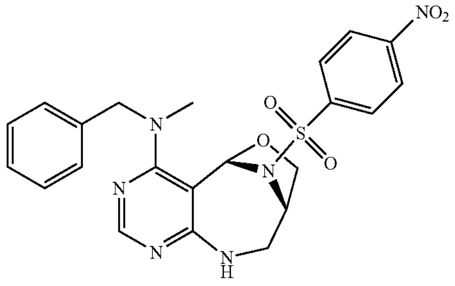

pale yellow solid; $R_f$=0.3 (EtOAc); 53.5 mg, 59% overall yield;

$^1$H NMR (400 MHz, $CDCl_3$): 8.16-8.14 (m, 3H), 7.51-7.40 (m, 7H), 6.54 (s, 1H), 5.65 (d, J=3.9 Hz, 1H), 4.71 (s, 2H), 4.53 (br s, 1H), 3.82 (dd, J=7.4, 2.0 Hz, 1H), 3.64 (d, J=13.3 Hz, 1H), 3.45 (m, 1H), 3.05-3.01 (m, 4H);

$^{13}$C NMR (100 MHz, $CDCl_3$): 166.4, 163.3, 156.2, 150.5, 143.6, 138.2, 129.1, 129.0, 127.5, 127.4, 124.5, 102.5, 87.5, 66.8, 58.9, 56.6, 48.6, 39.5;

IR (neat) $v_{max}$: 2970, 1739, 1558, 1530, 1400, 1351, 1169, 738 $cm^{-1}$; HRMS(ESI+):

Calcd for $C_{22}H_{23}N_6O_5S^+$ [M+H]$^+$ 483.1445, found 483.1439, Δppm −1.24; mp: 97-99° C.

3-6. Synthesis of Compound 106 (SB1606)

SB1606 was synthesized according to the synthesis procedure of SB1601 of Example 3-1 using 4-fluorobenzenesulfonyl chloride instead of p-toluenesulfonyl chloride.

Compound 106: SB1606

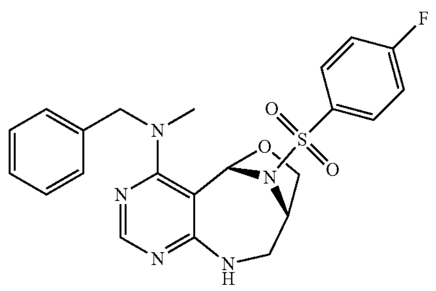

white solid; $R_f$=0.4 (EtOAc); 56.8 mg, 63% overall yield;

$^1$H NMR (500 MHz, $CDCl_3$): 8.12 (s, 1H), 7.45-7.39 (m, 6H), 7.34 (m, 1H), 7.03 (m, 2H), 6.57 (s, 1H), 5.97 (br s, 1H), 4.72, 4.69 (ABq, $J_{AB}$=16.5 Hz, 2H), 4.47 (br s, 1H), 3.77 (dd, J=7.6, 2.2 Hz, 1H), 3.58 (d, J=13.2 Hz, 1H), 3.40 (dt, J=13.2, 4.9 Hz, 1H), 2.99 (s, 3H), 2.97 (d, J=7.5 Hz, 1H);

$^{13}$C NMR (100 MHz, $CDCl_3$): 166.3, 165.6 (d, $^1J_{c,f}$=255.1Hz), 163.4, 156.0, 138.2, 133.9 (d, $^4J_{c,f}$=3.0 Hz), 130.5 (d, $^3J_{c,f}$=9.9 Hz), 128.8, 127.5, 127.3, 116.7 (d, $^2J_{c,f}$=22.0 Hz), 103.0, 87.6, 66.7, 58.7, 56.4, 48.7, 39.7;

IR (neat) $v_{max}$: 3245, 2921, 1571, 1351, 1169, 1155, 679 $cm^{-1}$;

HRMS(ESI+): Calcd for $C_{22}H_{23}FN_5O_3S^+$ [M+H]$^+$ 456.1500, found 456.1501, Δppm +0.22; mp: 105-107° C.

3-7. Synthesis of Compound 107 (SB1607)

SB1607 was synthesized according to the synthesis procedure of SB1601 of Example 3-1 using methanesulfonyl chloride instead of p-toluenesulfonyl chloride.

Compound 107 SB1607

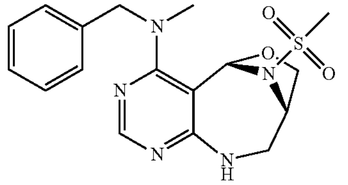

white solid; $R_f$=0.25 (EtOAc); 55.8 mg, 75% overall yield;

$^1$H NMR (400 MHz, $CDCl_3$): 8.14 (s, 1H), 7.37-7.26 (m, 5H), 6.58 (s, 1H), 5.92 (br d, J=4.3 Hz, 1H), 4.73 (d, J=16.0 Hz, 1H), 4.64 (br s, 1H), 4.55 (d, J=16.0 Hz, 1H), 4.10 (dd, J=7.6, 1.8 Hz, 1H), 3.92 (t, J=7.4 Hz, 1H), 3.60-3.47 (m, 2H), 2.96 (s, 3H), 2.73 (s, 3H);

$^{13}$C NMR (100 MHz, $CDCl_3$): 166.6, 163.5, 156.1, 138.0, 128.7, 127.6, 127.3, 102.5, 87.3, 67.1, 58.2, 56.6, 48.7, 40.4, 38.5;

IR (neat) $\nu_{max}$: 2912, 2109, 1571, 1538, 1350, 1168, 738 cm-;

HRMS(ESI+): Calcd for $C_{17}H_{22}N_5O_3S^+$ [M+H]$^+$ 376.1438, found 376.1437, Δppm −0.27; mp: 136-138° C.

3-8. Synthesis of Compound 108 (SB1608)

The SB11608 was synthesized according to the synthesis procedure of SB1601 of Example 3-1 using the benzenesulfonyl chloride instead of p-toluenesulfonyl chloride.

Compound 108: SB1608

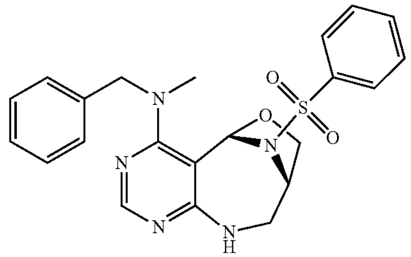

white solid; $R_f$=0.38 (EtOAc); 67.6 mg, 78% overall yield;

$^1$H NMR (500 MHz, $CDCl_3$): 8.12 (s, 1H), 7.56 (m, 1H), 7.56 (m, 2H), 7.44-7.37 (m, 6H), 7.33 (m, 1H), 6.63 (s, 1H), 5.95 (br d, J=4.9 Hz, 1H), 4.73, 4.69 (ABq, $J_{AB}$=16.3 Hz, 2H), 4.50 (br t, J=4.9 Hz, 1H), 3.75 (dd, J=7.3, 1.5 Hz, 1H), 3.56 (d, J=12.7 Hz, 1H), 3.40 (dt, J=13.2, 5.0 Hz, 1H), 3.00 (s, 3H), 2.93 (t, J=6.8 Hz, 1H);

$^{13}$C NMR (100 MHz, $CDCl_3$): 166.3, 163.5, 155.9, 138.2, 137.9, 133.6, 129.4, 128.8, 127.7, 127.6, 127.2, 103.2, 87.7, 66.8, 58.6, 56.3, 48.7, 40.0;

IR (neat) $\nu_{max}$: 3380, 1739, 1536, 1352, 1170, 974, 723, 696 cm$^{-1}$;

HRMS(ESI+): Calcd for $C_{22}H_{24}N_5O_3S^+$ [M+H]$^+$ 438.1594, found 438.1595, Δppm +0.23; mp: 120-122° C.

3-9. Synthesis of Compound 109 (SB1609)

SB1609 was synthesized according to the synthesis procedure of SB1601 of Example 3-1 using the benzylsulfonyl chloride instead of p-toluenesulfonyl chloride.

Compound 109: SB1609

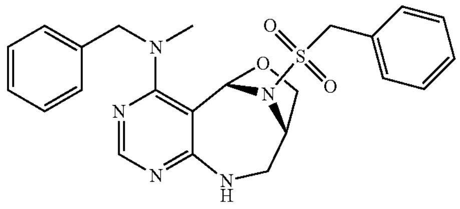

white solid; $R_f$=0.32 (EtOAc); 54.5 mg, 61% overall yield;

$^1$H NMR (400 MHz, $CDCl_3$): 8.11 (s, 1H), 7.39-7.35 (m, 2H), 7.30-7.21 (m, 8H), 6.60 (s, 1H), 5.76 (br s, 1H), 4.66, 4.50 (ABq, $J_{AB}$=15.6 Hz, 2H), 4.32 (br s, 1H), 4.09 (s, 2H), 3.97 (d, J=7.4 Hz, 1H), 3.72 (t, J=6.8 Hz, 1H), 3.28 (m, 2H), 2.81 (s, 3H);

$^{13}$C NMR (100 MHz, $CDCl_3$): 166.4, 163.6, 156.0, 138.0, 131.0, 129.1, 128.8, 128.7, 127.9, 127.7, 127.3, 102.2, 87.0, 68.0, 59.4, 57.7, 57.2, 48.1, 40.1;

IR (neat) $\nu_{max}$: 2970, 1741, 1558, 1403, 1349, 1161, 1049, 969, 696 cm$^{-1}$;

HRMS(ESI+): Calcd for $C_{23}H_{26}N_5O_3S^+$ [M+H]$^+$ 452.1751, found 452.1747, Δppm −0.88; mp: 78-80° C.

3-10. Synthesis of Compound 110 (SB1610)

SB1610 was synthesized according to the synthesis procedure of SB1601 of Example 3-1 using pyridine-3-sulfonyl chloride instead of p-toluenesulfonyl chloride.

Compound 110: SB1610

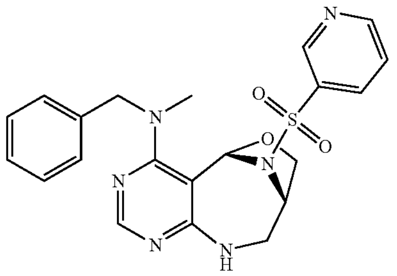

white solid; $R_f$=0.15 (EtOAc); 53.8 mg, 62% overall yield;

$^1$H NMR (600 MHz, DMSO-$d_6$, 77° C.): 8.93 (s, 1H), 8.86 (d, J=4.0 Hz, 1H), 8.05 (m, 2H), 7.56 (dd, J=7.3, 5.1Hz, 1H), 7.38 (m, 2H), 7.30 (m, 3H), 6.97 (br s, 1H), 6.66 (s, 1H), 4.80 (br s, 1H), 4.66 (d, J=15.6 Hz, 1H), 4.66 (d, J=15.6 Hz, 1H), 3.71 (br d, J=6.6 Hz, 1H), 3.52 (m, 1H), 3.33 (d, J=13.9 Hz, 1H), 3.04 (br s, 1H), 2.90 (s, 3H);

$^{13}$C NMR (150 MHz, DMSO-$d_6$, 77° C.): 165.5, 162.9, 155.3, 153.8, 147.2, 137.9, 134.9, 134.2, 128.0, 127.1, 126.6, 124.0, 101.7, 86.7, 66.4, 57.0, 55.6, 47.6, 39.8; IR (neat) $\nu_{max}$: 3313, 1732, 1555, 1353, 1171, 980, 957, 690 $cm^{-1}$;

HRMS(ESI+): Calcd for $C_{21}H_{23}N_6O_3S^+$ $[M+H]^+$ 439.1547, found 439.1553; Δppm +1.37, mp: 185-187° C.

3-11. Synthesis of Compound 111 (SB1611)

The following SB1611 was synthesized according to the synthesis procedure of SB1601 of Example 3-1 using 2-thiophenesulfonyl chloride instead of p-toluenesulfonyl chloride.

Compound 111: SB1611

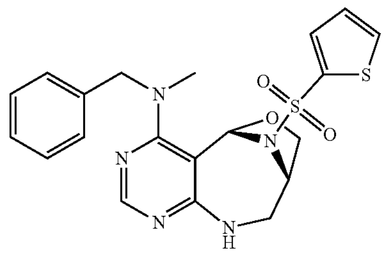

white solid; $R_f$=0.33 (EtOAc); 51.8 mg, 59% overall yield;

$^1$H NMR (500 MHz, DMSO-$d_6$): 8.10 (dd, J=4.9, 1.5 Hz, 1H), 8.03 (s, 1H), 7.57 (dd, J=3.7, 1.2 Hz, 1H), 7.39-7.36 (m, 2H), 7.30-7.28 (m, 3H), 7.25 (d, J=4.9 Hz, 1H), 7.22 (dd, J=4.9, 3.9 Hz, 1H), 6.60 (s, 1H), 4.75 (br s, 1H), 4.66 (d, J=15.7 Hz, 1H), 4.49 (d, J=15.7 Hz, 1H), 3.63 (dd, J=7.3, 1.5 Hz, 1H), 3.52 (dt, J=13.9, 5.0 Hz, 1H), 3.28 (d, J=13.2 Hz, 1H), 2.93 (t, J=7.1Hz, 1H), 2.86 (s, 3H);

$^{13}$C NMR (100 MHz, DMSO-$d_6$): 165.6, 163.3, 155.7, 138.1, 136.9, 135.5, 134.1, 128.5, 127.5, 127.0, 102.0, 87.1, 66.6, 57.4, 56.1, 47.9, 40.2;

IR (neat) $\nu_{max}$: 3241, 1739, 1577, 1542, 1355, 1166, 1026, 970, 674 $cm^{-1}$;

HRMS(ESI+): Calcd for $C_{20}H_{22}N_5O_3S_2^+$ $[M+H]^+$ 444.1159, found 444.1159; mp: 112-114° C.

3-12. Synthesis of Compound 112 (SB1612)

The following SB1612 was synthesized by using Compound 2 instead of Compound 1 in accordance with the synthesis procedure of SB1601 in Example 3-1.

Compound 112: SB1612

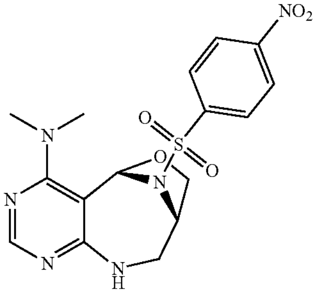

yellow solid; $R_f$=0.27 (EtOAc); 41.8 mg, 52% overall yield;

$^1$H NMR (400 MHz, $CDCl_3$): 8.37 (d, J=8.6 Hz, 2H), 8.12 (d, J=9.0 Hz, 2H), 8.06 (s, 1H), 6.69 (s, 1H), 5.93 (br s, 1H), 4.54 (br s, 1H), 3.85 (dd, J=7.6, 1.4 Hz, 1H), 3.46 (m, 2H), 3.07 (s, 6H), 3.01 (t, J=7.0 Hz, 1H);

$^{13}$C NMR (100 MHz, $CDCl_3$): 166.8, 163.4, 156.1, 150.7, 144.2, 129.3, 124.6, 102.1, 88.3, 67.1, 56.5, 48.5, 43.2;

IR (neat) $\nu_{max}$: 3409, 2924, 1579, 1524, 1351, 1313, 1171, 738, 685 $cm^{-1}$;

HRMS(ESI+): Calcd for $C_{16}H_{19}N_6O_5S^+$ $[M+H]^+$ 407.1132, found 407.1130, Δppm −0.49; mp: 118-120° C.

3-13. Synthesis of Compound 113 (SB1613)

The following SB1613 was synthesized in accordance with the synthesis procedure of SB1601 in Example 3-1 using 4-nitrobenzenesulfonyl chloride instead of p-toluenesulfonyl chloride, and Compound 3 instead of Compound 1.

Compound 113: SB1613

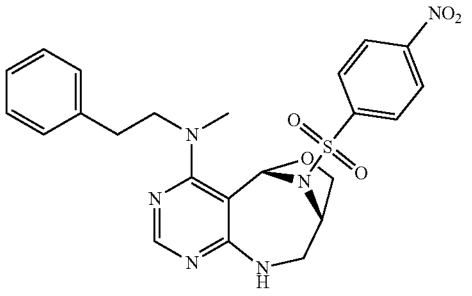

light yellow solid; $R_f$=0.45 (EtOAc); 61.0 mg, 62% overall yield;

$^1$H NMR (400 MHz, $CDCl_3$): 8.33 (d, J=8.6 Hz, 2H), 8.08 (s, 1H), 7.99 (d, J=8.6 Hz, 2H), 7.30-7.21 (m, 5H), 6.55 (s, 1H), 6.08 (br s, 1H), 4.54 (br s, 1H), 3.97 (m, 1H), 3.84 (d, J=7.0 Hz, 1H), 3.46 (m, 3H), 3.09 (s, 3H), 3.00 (m, 2H), 2.89 (m, 1H);

$^{13}$C NMR (100 MHz, $CDCl_3$): 166.5, 163.5, 156.0, 150.6, 144.1, 139.6, 129.2, 128.9, 128.5, 126.2, 124.5, 102.6, 88.1, 67.0, 56.5, 54.5, 48.4, 42.5, 33.8;

IR (neat) $\nu_{max}$: 3411, 1739, 1580, 1524, 1354, 1169, 738 $cm^{-1}$;

HRMS(ESI+): Calcd for $C_{23}H_{25}N_6O_5S^+$ $[M+H]^+$ 497.1602, found 497.1603, Δppm +0.20; mp: 108-110° C.

3-14. Synthesis of Compound 114 (SB1614)

The following SB1614 was synthesized in accordance with the synthesis procedure of SB1601 in Example 3-1 using 4-nitrobenzenesulfonyl chloride instead of p-toluenesulfonyl chloride, and Compound 4 instead of Compound 1.

Compound 114: SB1614

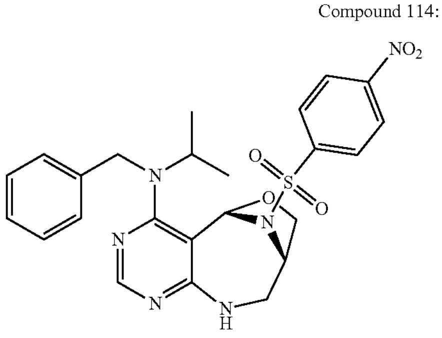

light yellow solid; $R_f$=0.5 (EtOAc); 51.6 mg, 51% overall yield;

$^1$H NMR (400 MHz, $CDCl_3$):8.28 (d, J=8.2 Hz, 2H), 8.05 (s, 1H), 7.92 (d, J=7.8 Hz, 2H), 7.37 (d, J=7.4 Hz, 2H), 7.28 (m, 2H), 7.18 (m, 1H), 6.85 (s, 1H), 5.82 (br s, 1H), 4.59 (m, 2H), 4.49 (d, J=14.8 Hz, 1H), 3.96 (m, 1H), 3.85 (d, J=7.8 Hz, 1H), 3.55 (d, J=13.3 Hz, 1H), 3.38 (m, 1H), 3.27 (t, J=7.2 Hz, 1H), 1.34 (d, J=6.3 Hz, 3H), 1.29 (d, J=6.3 Hz, 3H);

$^{13}$C NMR (100 MHz, $CDCl_3$):167.0, 163.4, 155.9, 150.5, 144.2, 140.3, 128.9, 128.3, 127.9, 126.6, 124.6, 106.9, 87.5, 67.2, 56.7, 56.6, 48.3, 46.3, 20.7, 20.0;

IR (neat) $\nu_{max}$: 2970, 1738, 1568, 1531, 1348, 1169, 1061, 737 $cm^{-1}$;

HRMS(ESI+): Calcd for $C_{24}H_{27}N_6O_5S^+$ [M+H]$^+$ 511.1758, found 511.1761, Δppm +0.59; mp: 85-87° C.

3-15. Synthesis of Compound 115 (SB1615)

The following SB1615 was synthesized in accordance with the synthesis procedure of SB1601 in Example 3-1 using 4-nitrobenzenesulfonyl chloride instead of p-toluenesulfonyl chloride, and Compound 5 instead of Compound 1.

Compound 115: SB1615

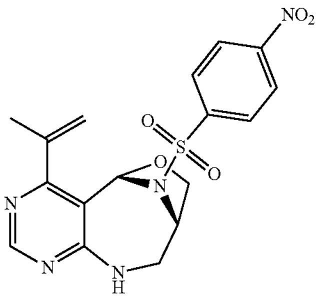

light yellow solid; $R_f$=0.35 (EtOAc); 44.7 mg, 56% overall yield;

$^1$H NMR (400 MHz, $CDCl_3$): 8.46 (s, 1H), 8.41 (d, J=8.6 Hz, 2H), 8.09 (d, J=9.0 Hz, 2H), 6.85 (s, 1H), 5.74 (br d, J=3.9 Hz, 1H), 5.56 (s, 1H), 5.17 (s, 1H), 4.63 (br s, 1H), 3.91 (dd, J=7.6, 1.8 Hz, 1H), 3.66 (d, J=12.5 Hz, 1H), 3.50 (m, 1H), 3.25 (t, J=7.2 Hz, 1H), 2.17 (s, 3H);

$^{13}$C NMR (100 MHz, $CDCl_3$):167.4, 162.8, 157.0, 150.8, 143.8, 142.1, 129.1, 124.9, 119.5, 114.5, 87.9, 67.0, 56.2, 48.9, 22.9;

IR (neat) $\nu_{max}$: 3290, 2977, 1740, 1557, 1529, 1346, 1170, 907, 737 $cm^{-1}$;

HRMS(ESI+): Calcd for $C_{17}H_{18}N_5O_5S^+$ [M+H]$^+$ 404.1023, found 404.1023; mp: 200-202° C.

3-16. Synthesis of Compound 116 (SB1616)

The following SB1616 was synthesized in accordance with the synthesis procedure of SB1601 in Example 3-1 using 4-nitrobenzenesulfonyl chloride instead of p-toluenesulfonyl chloride, and Compound 6 instead of Compound 1.

Compound 116: SB1616

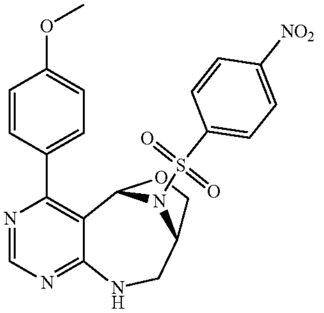

white solid; $R_f$=0.35 (EtOAc); 41.8 mg, 45% overall yield;

$^1$H NMR (500 MHz, DMSO-$d_6$): 8.41 (m, 3H), 8.03 (d, J=8.3 Hz, 2H), 7.65 (br d, J=4.4 Hz, 1H), 7.52 (d, J=8.3 Hz, 2H), 7.09 (d, J=8.3 Hz, 2H), 6.47 (s, 1H), 4.89 (br s, 1H), 3.87 (s, 3H), 3.70 (d, J=7.3 Hz, 1H), 3.55 (m, 1H), 3.39 (d, J=14.0 Hz, 1H), 3.08 (t, J=7.3 Hz, 1H);

$^{13}$C NMR (100 MHz, DMSO-$d_6$):163.3, 162.5, 160.2, 156.6, 150.6, 142.5, 131.2, 129.6, 129.1, 125.1, 113.7, 113.5, 87.5, 66.9, 55.7, 55.3, 48.1;

IR (neat) $\nu_{max}$: 3244, 3109, 3005, 1739, 1570, 1528, 1352, 1168, 740 $cm^{-1}$;

HRMS(ESI+): Calcd for $C_{21}H_{20}N_5O_6S^+$ [M+H]$^+$ 470.1129, found 470.1127, Δppm −0.43; mp: 250-252° C.

3-17. Synthesis of Compound 117 (SB1617)

The following SB1617 was synthesized in accordance with the synthesis procedure of SB1 601 in Example 3-1 using 4-nitrobenzenesulfonyl chloride instead of p-toluenesulfonyl chloride, and Compound 7 instead of Compound 1.

Compound 117: SB1617

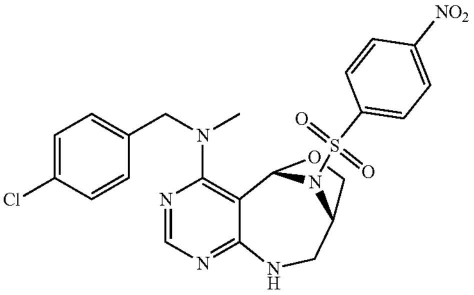

light yellow; $R_f$=0.40 (EtOAc); 58.3 mg, 57% overall yield;

$^1$H NMR (400 MHz, $CDCl_3$): 8.24 (d, J=8.6 Hz, 2H), 8.13 (s, 1H), 7.63 (d, J=8.6 Hz, 2H), 7.42, 7.35 (ABq, $J_{AB}$=8.2 Hz, 4H), 6.56 (s, 1H), 5.73 (d, J=3.9 Hz, 1H), 4.67, 4.62 (ABq, $J_{AB}$=17.0 Hz, 2H), 4.54 (br s, 1H), 3.84 (d, J=7.4 Hz, 1H), 3.61 (d, J=13.3 Hz, 1H), 3.45 (dt, J=13.3, 4.7 Hz, 1H), 3.07 (t, J=7.0 Hz, 1H), 2.99 (s, 3H);

$^{13}$C NMR (100 MHz, $CDCl_3$):166.4, 163.4, 156.3, 150.6, 143.7, 136.8, 133.2, 129.1, 129.03, 128.95, 124.6, 102.8, 87.5, 67.0, 58.0, 56.5, 48.6, 40.1;

IR(neat) $\nu_{max}$: 3248, 3016, 1739, 1565, 1529, 1350, 1169, 738 cm-;

HRMS(ESI+): Calcd for $C_{22}H_{22}ClN_6O_5S^+$ [M+H]$^+$ 517.1055, found 517.1053, Δppm −0.39; mp: 110-112° C.

3-18. Synthesis of Compound 118 (SB1618)

The following SB1618 was synthesized in accordance with the synthesis procedure of SB1601 in Example 3-1 using 4-nitrobenzenesulfonyl chloride instead of p-toluene-sulfonyl chloride, and Compound 8 instead of Compound 1.

Compound 118: SB1618

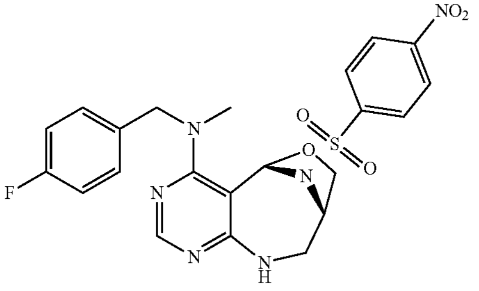

light yellow; $R_f$=0.39 (EtOAc); 54.5 mg, 55% overall yield;

$^1$H NMR (500 MHz, $CDCl_3$): 8.24 (d, J=8.8 Hz, 2H), 8.12 (s, 1H), 7.69 (d, J=8.8 Hz, 2H), 7.36 (dd, J=8.1, 5.6 Hz, 2H), 7.12 (t, J=8.6 Hz, 2H), 6.61 (s, 1H), 5.76 (br d, J=4.4 Hz, 1H), 4.64 (s, 2H), 4.54 (br s, 1H), 3.84 (dd, J=7.8, 1.5 Hz, 1H), 3.59 (d, J=13.2 Hz, 1H), 3.45 (dt, J=13.7, 4.9 Hz, 1H), 3.07 (t, J=7.1Hz, 1H), 2.98 (s, 3H);

$^{13}$C NMR (100 MHz, $CDCl_3$):166.4, 163.4, 162.3 (d, $^1J_{c,f}$=244.4 Hz), 156.3, 150.6, 143.8, 133.8 (d, $^4J_{c,f}$=3.8 Hz), 129.3 (d, $^3J_{c,f}$=7.6 Hz), 129.0, 124.5, 115.7 (d, $^2J_{c,f}$=21.3 Hz), 102.8, 87.6, 67.0, 57.9, 56.5, 48.6, 40.0;

IR (neat) $\nu_{max}$: 3246, 3018, 1739, 1567, 1533, 1498, 1349, 1170, 739 $cm^{-1}$;

HRMS(ESI+): Calcd for $C_{22}H_{22}FN_6O_5S^+$ $[M+H]^+$ 501.1351, found 501.1353, Δppm +0.40; mp: 102-104° C.

3-19. Synthesis of Compound 119 (SB1619)

The following SB1619 was synthesized in accordance with the synthesis procedure of SB1601 in Example 3-1 using 4-nitrobenzenesulfonyl chloride instead of p-toluene-sulfonyl chloride, and Compound 9 instead of Compound 1.

Compound 119: SB1619

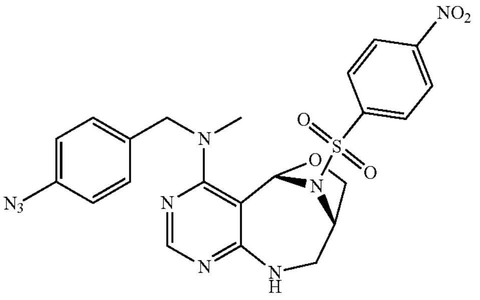

light yellow solid; $R_f$=0.40 (EtOAc); 61.2 mg, 59% overall yield;

$^1$H NMR (400 MHz, $CDCl_3$):8.24 (d, J=8.6 Hz, 2H), 8.11 (s, 1H), 7.72 (d, J=8.6 Hz, 2H), 7.37 (d, J=8.2 Hz, 2H), 7.09 (d, J=8.2 Hz, 2H), 6.61 (s, 1H), 5.86 (br d, J=4.3 Hz, 1H), 4.64 (s, 2H), 4.54 (br s, 1H), 3.84 (d, J=7.8 Hz, 1H), 3.59 (d, J=13.2 Hz, 1H), 3.45 (dt, J=13.4, 4.8 Hz, 1H), 3.08 (t, J=7.0 Hz, 1H), 2.98 (s, 3H);

$^{13}$C NMR (100 MHz, $CDCl_3$):166.4, 163.5, 156.2, 150.6, 143.8, 139.3, 134.9, 129.2, 129.0, 124.5, 119.4, 102.8, 87.6, 67.0, 58.0, 56.5, 48.6, 40.1;

IR (neat) $\nu_{max}$: 2900, 2109, 1572, 1530, 1349, 1168, 738 $cm^{-1}$;

HRMS(ESI+): Calcd for $C_{22}H_{22}N_9O_5S^+$ $[M+H]^+$ 524.1459, found 524.1460, Δppm +0.19; mp: 88-90° C.

3-20. Synthesis of Compound 120 (SB1620)

The following SB1620 was synthesized in accordance with the synthesis procedure of SB1601 in Example 3-1 using 4-fluorobenzenesulfonyl chloride instead of p-toluene-sulfonyl chloride, and Compound 7 instead of Compound 1.

Compound 120: SB1620

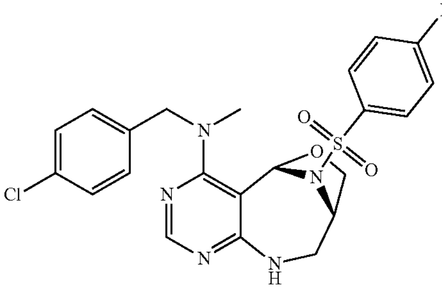

white solid; $R_f$=0.40 (EtOAc); 57.2 mg, 59% overall yield;

$^1$H NMR (400 MHz, $CDCl_3$): 8.11 (s, 1H), 7.50 (dd, J=8.6, 4.7 Hz, 2H), 7.39, 7.33 (ABq, $J_{AB}$=8.4 Hz, 4H), 7.10 (t, J=8.4 Hz, 2H), 6.56 (s, 1H), 5.92 (br d, J=4.7 Hz, 1H), 4.65 (s, 2H), 4.48 (br s, 1H), 3.78 (d, J=7.4 Hz, 1H), 3.56 (d, J=13.2 Hz, 1H), 3.41 (dt, J=13.5, 4.8 Hz, 1H), 2.99 (m, 4H);

$^{13}$C NMR (100 MHz, $CDCl_3$):166.2, 165.7 (d, $^1J_{c,f}$=255.8 Hz), 163.5, 156.1, 136.8, 133.9 (d, $^4J_{c,f}$=3.0 Hz), 133.0, 130.5 (d, $^3J_{c,f}$=9.9 Hz), 129.1, 129.0, 116.8 (d, $^2J_{c,f}$=22.8 Hz), 103.3, 87.6, 66.8, 57.9, 56.3, 48.7, 40.2;

IR (neat) $\nu_{max}$: 3015, 1739, 1570, 1491, 1351, 1231, 1171, 1157, 678 $cm^{-1}$;

HRMS(ESI+): Calcd for $C_{22}H_{22}ClFN_5O_3S^+$ $[M+H]^+$ 490.1110, found 490.1112, Δppm +0.41; mp: 150-152° C.

3-21. Synthesis of Compound 121 (SB1621)

The following SB1621 was synthesized in accordance with the synthesis procedure of SB1601 in Example 3-1 using 4-methoxybenzenesulfonyl chloride instead of p-toluenesulfonyl chloride, and Compound 7 instead of Compound 1.

Compound 121: SB1621

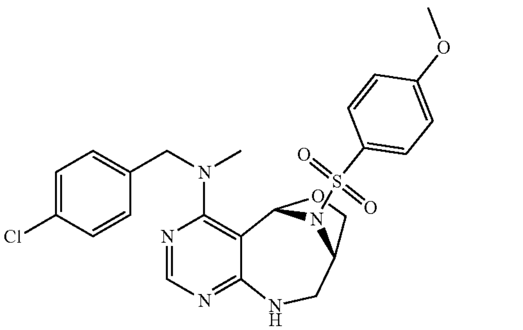

white solid; $R_f$=0.35 (EtOAc); 61.6 mg, 62% overall yield;

$^1$H NMR (400 MHz, $CDCl_3$):8.10 (s, 1H), 7.45 (d, J=8.6 Hz, 2H), 7.37, 7.32 (ABq, $J_{AB}$=8.2 Hz, 4H), 6.88 (d, J=8.6 Hz, 2H), 6.57 (s, 1H), 5.85 (br s, 1H), 4.65 (s, 2H), 4.47 (br s, 1H), 3.85 (s, 3H), 3.75 (d, J=7.4 Hz, 1H), 3.54 (d, J=13.3 Hz, 1H), 3.40 (dt, J=13.2, 4.9 Hz, 1H), 2.99 (m, 4H);

$^{13}$C NMR (100 MHz, $CDCl_3$):166.1, 163.7, 163.5, 156.0, 136.9, 132.9, 129.9, 129.3, 129.2, 128.9, 114.6, 103.7, 87.7 (C11, d, J=2.3 Hz), 66.9, 57.9, 56.3, 55.8 (C25, d, J=2.3 Hz), 48.8, 40.3;

IR (neat) $\nu_{max}$: 2970, 1739, 1574, 1496, 1349, 1161, 680 $cm^{-1}$;

HRMS(ESI+): Calcd for $C_{23}H_{25}ClN_5O_4S^+$ $[M+H]^+$ 502.1310, found 502.1310; mp: 156-158° C.

3-22. Synthesis of Compound 122 (SB1622)

SB11622, the pyrimidiazepine derivative according to the present invention, was synthesized according to the following Reaction Formula 2.

[Reaction Formula 2]

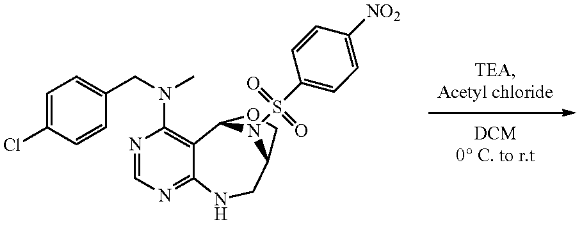

SB1617

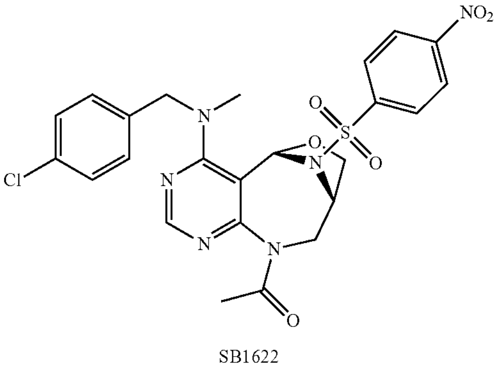

SB1622

$Et_3N$ (0.032 ml, 0.226 mmol) and acetyl chloride (AcCl, 0.010 ml, 0.147 mmol) were sequentially added to a solution obtained by mixing SB1617 (58.3 mg, 0.113 mmol) with dichloromethane (5 ml). The resulting mixture was stirred and heated to room temperature. After completion of the reaction, the resultant was quenched with saturated $NaHCO_3$ (aq) and extracted twice with dichloromethane. The combined organic layer was dried with anhydrous $Na_2SO_4$(s), the filtrate was decompressed and concentrated, and the target product SB1622 (51.2 mg, 81% yield, a white solid) was obtained using silica gel flash column chromatography.

Compound 122: SB1622

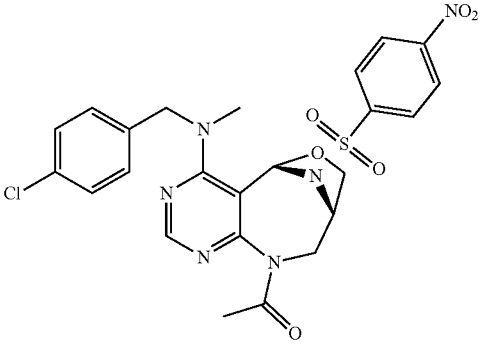

$R_f$=0.2 (Hexane/EtOAc=1:1);

$^1$H NMR (400 MHz, $CDCl_3$):8.50 (s, 1H), 8.24 (d, J=9.0 Hz, 2H), 7.59 (d, J=9.0 Hz, 2H), 7.45, 7.39 (ABq, $J_{AB}$=8.2 Hz, 4H), 6.47 (s, 1H), 4.81-4.65 (m, 3H), 4.45 (br s, 1H), 3.80 (d, J=8.2 Hz, 1H), 3.38 (br s, 1H), 3.14 (s, 3H), 2.96 (dd, J=7.8, 5.5 Hz, 1H), 2.06 (s, 3H);

$^{13}$C NMR (100 MHz, $CDCl_3$):171.1, 165.8, 161.0, 156.1, 150.6, 144.0, 135.7, 133.7, 129.3, 128.9, 128.6, 124.8, 86.3, 69.1, 58.2, 57.6, 46.1, 40.2, 23.6;

IR (neat) $\nu_{max}$: 2970, 1739, 1674, 1559, 1530, 1350, 1229, 1169, 738 $cm^{-1}$;

HRMS(ESI+): Calcd for $C_{24}H_{24}ClN_6O_6S^+$ $[M+H]^+$ 559.1161, found 559.1175, Δppm +2.50, mp: 105-107° C.

3-23. Synthesis of Compound 123 (SB1623)

The following SB1623 was synthesized in accordance with the synthesis procedure of SB1 622 of Example 3-22, by using cyclopropane carbonyl chloride instead of acetyl chloride.

Compound 123: SB1623

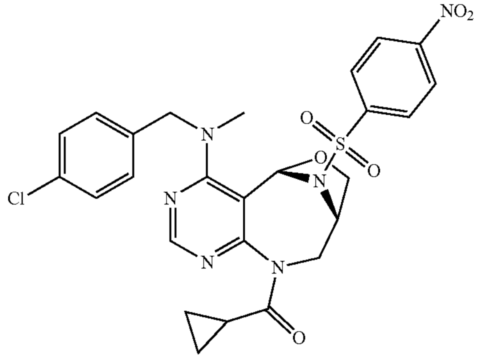

light yellow; $R_f$=0.35 (Hexane/EtOAc=1:1); 56.2 mg, 85% overall yield;

$^1$H NMR (400 MHz, $CDCl_3$):8.53 (s, 1H), 8.23 (d, J=8.6 Hz, 2H), 7.59 (d, J=9.0 Hz, 2H), 7.45, 7.40 (ABq, $J_{AB}$=8.2 Hz, 4H), 6.51 (s, 1H), 4.74 (m, 3H), 4.45 (br s, 1H), 3.75 (d, J=7.8 Hz, 1H), 3.40 (br d, J=8.6 Hz, 1H), 3.14 (s, 3H), 2.94 (m, 1H), 1.63 (m, 1H), 1.05 (m, 2H), 0.81 (m, 1H), 0.70 (m, 1H);

$^{13}$C NMR (100 MHz, $CDCl_3$): 174.8, 165.9, 161.0, 156.1 (C2, d, J=3.8 Hz), 150.6, 144.0, 135.7, 133.7, 129.3, 128.9, 128.7, 124.8, 86.4, 69.0, 58.2, 57.6, 46.5, 40.2 (C25, d, J=3.7 Hz), 14.0;

IR (neat) $\nu_{max}$: 2970, 1739, 1665, 1558, 1530, 1398, 1350, 1168, 738 $cm^{-1}$;

HRMS(ESI+): Calcd for $C_{26}H_{26}ClN_6O_6S^+$ [M+H]$^+$ 585.1318, Δppm +1.03; found 585.1324; mp: 124-126° C.

3-24. Synthesis of Compound 124 (SB1624)

SB11624, the pyrimidiazepine derivative according to the present invention, was synthesized according to Reaction Formula 3.

[Reaction Formula 3]

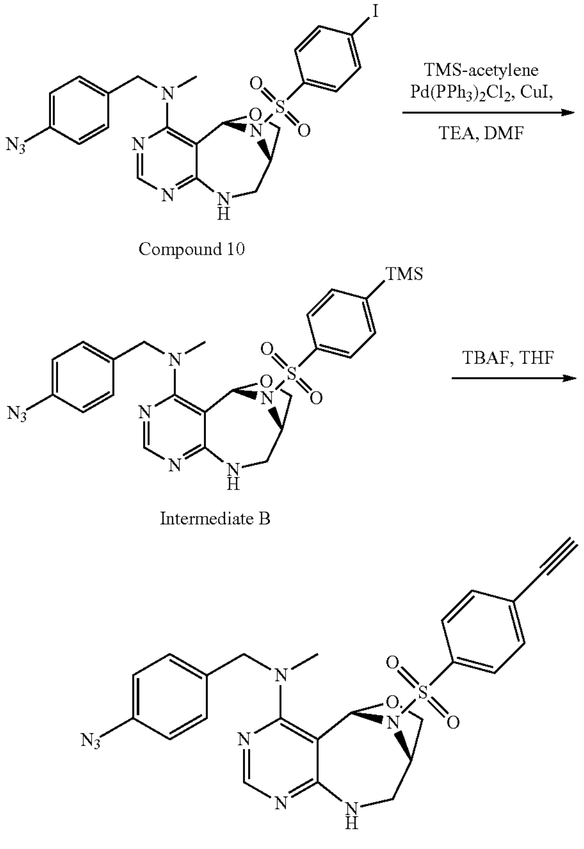

Compound 10

Intermediate B

SB1624

Trimethylsilyl acetylene (0.033 mL, 0.242 mmol), $Pd(PPh_3)_2Cl_2$(8.50 mg, 0.012 mmol, 10 mol %), copper iodide(CuI, 11.6 mg, 0.061 mmol), and trimethylaminetrimethylamine; TEA, 0.051 mL, 0.363 mmol) were added to a solution obtained by mixing compound 10 (73.0 mg, 0.121 mmol) with dimethylformamide (DMF, 6 mL), and the resulting mixture was stirred at room temperature. After completion of the reaction, the reaction mixture was quenched with saturated $NH_4Cl$ (aq), and the resulting product was extracted twice with ethyl acetate. The organic layer was dried with anhydrous $Na_2SO_4$ (s) and filtered. After the filtrate was concentrated under reduced pressure, intermediate B (54.0 mg, 81% yield) was obtained using silica gel flash column chromatography. TBAF (1.0 M solution in THF, 0.127 mL, and 0.127 mmol) was added to a solution in which THF (2 mL) was mixed with intermediate B (54.0 mg, 0.098 mmol). Then, the reaction mixture was stirred at room temperature. After completion of the reaction, the solvent was removed under reduced pressure, and the residue was purified by silica gel flash column chromatography to obtain the following SB1624 (25.1 mg, 51% yield, 41% total yield, and yellow solid).

Compound 124: SB1624

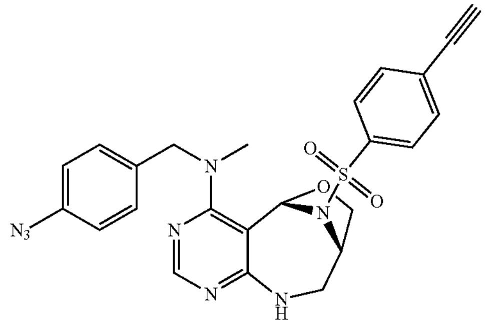

$R_f$=0.45 (EtOAc);

$^1$H NMR (400 MHz, $CDCl_3$):8.14 (s, 1H), 7.53 (s, 4H), 7.37 (d, J=8.0 Hz, 2H), 7.08 (d, J=8.0 Hz, 2H), 6.63 (s, 1H), 5.57 (br s, 1H), 4.66 (s, 2H), 4.49 (br s, 1H), 3.81 (d, J=8.0 Hz, 1H), 3.57 (d, J=12.0 Hz, 1H), 3.43 (m, 1H), 3.31 (s, 1H), 3.02 (m, 4H);

$^{13}$C NMR (100 MHz, $CDCl_3$):166.3, 163.3, 155.9, 139.2, 137.9, 135.0, 133.0, 129.3, 128.0, 127.7, 119.4, 103.4, 87.7, 81.80, 81.78, 66.9, 58.0, 56.4, 48.8, 40.3;

IR (neat) $\nu_{max}$: 3373, 3215, 2955, 2102, 1737, 1574, 1353, 1166, 973 cm-;

HRMS(ESI+): Calcd for $C_{24}H_{23}N_8O_3S^+$ [M+H]$^+$ 503.1608, found 503.1607, Δppm −0.20; mp: 139-141° C.

3-25. Synthesis of Compound 125 (SB1625) to Compound 136 (SB1636)

[Compound 125] SB1625

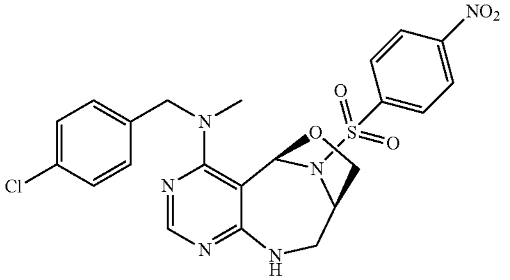

light yellow solid;

$^1$H NMR (400 MHz, $CDCl_3$): 8.29-8.22 (m, 2H), 8.15 (s, 1H), 7.66-7.60 (m, 2H), 7.44 (d, J=8.4 Hz, 2H), 7.36 (d,

J=8.5 Hz, 2H), 6.56 (s, 1H), 5.49 (m, 1H), 4.66 (m, 2H), 4.54 (m, 1H), 3.85 (m, 1H), 3.62 (m, 1H), 3.52-3.42 (m, 1H), 3.08 (m, 1H), 3.00 (s, 3H);

LRMS(ESI+): Calcd for $C_{22}H_{22}ClN_6O_5S^+$ [M+H]$^+$ 517.11, found 517.05

[Compound 126] SB1626

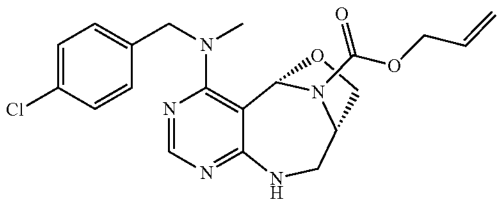

white solid;

$^1$H NMR (500 MHz, $CDCl_3$): 8.13 (s, 1H), 7.32-7.28 (m, 2H), 7.27-7.25 (m, 2H), 6.71 (s, 1H), 5.88 (m, 1H), 5.54 (m, 1H), 5.29 (m, 1H), 5.23 (m, 1H), 4.83 (m, 1H), 4.62-4.56 (m, 4H), 4.07-4.01 (m, 1H), 3.90 (m, 1H), 3.56 (m, 1H), 3.48 (m, 1H), 2.96 (s, 3H);

LRMS(ESI+): Calcd for $C_{20}H_{23}ClN_5O_3^+$ [M+H]$^+$ 416.15, found 416.05

[Compound 127] SB1627

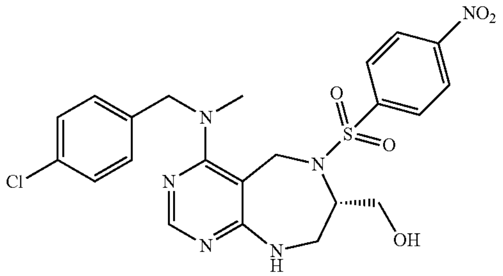

white solid;

$^1$H NMR (500 MHz, $CDCl_3$:MeOD=95:5, MeOD shim): 8.04-7.99 (m, 2H), 7.66 (s, 1H), 7.51-7.48 (m, 2H), 7.38 (m, 4H), 4.77 (m, 4H), 4.28 (m, 1H), 4.22 (m, 1H), 3.81-3.69 (m, 2H), 3.34 (m, 1H), 2.89 (s, 3H);

LRMS(ESI+): Calcd for $C_{22}H_{24}ClN_6O_5S^+$ [M+H]$^+$ 519.12, found 519.05

[Compound 128] SB1628

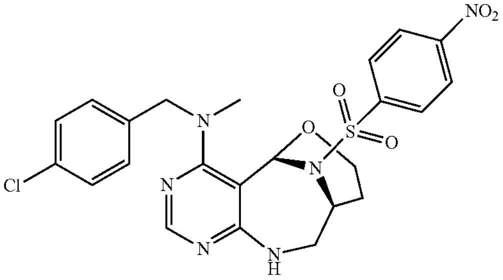

white solid;

$^1$H NMR (500 MHz, $CDCl_3$:MeOD=2:1, MeOD shim): 8.13-8.09 (m, 2H), 7.73 (s, 1H), 7.58-7.54 (m, 2H), 7.42-7.38 (m, 2H), 7.35-7.31 (m, 2H), 6.08 (s, 1H), 4.83-4.70 (m, 2H), 3.97 (m, 1H), 3.67 (m, 1H), 3.49 (m, 1H), 3.39 (m, 1H), 3.36 (m, 1H), 3.16 (s, 3H), 1.99 (m, 1H), 1.78 (m, 1H);

LRMS(ESI+): Calcd for $C_{23}H_{24}ClN_6O_5S^+$ [M+H]$^+$ 531.12, found 531.05

[Compound 129] SB1629

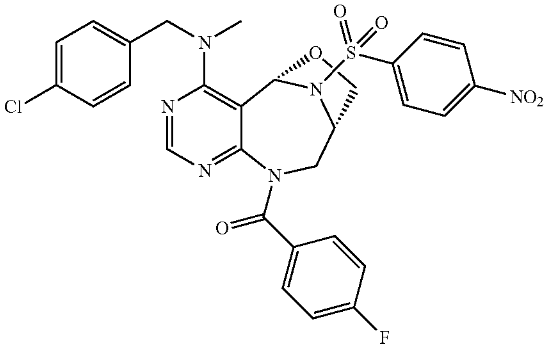

white solid;

$^1$H NMR (500 MHz, $CDCl_3$): 8.29 (m, 2H), 8.06 (s, 1H), 7.69 (m, 2H), 7.48-7.43 (m, 2H), 7.43 (s, 2H), 7.38 (m, 2H), 6.92 (m, 2H), 6.68 (s, 1H), 5.08 (m, 1H), 4.83 (m, 1H), 4.69-4.60 (m, 2H), 3.87 (m, 1H), 3.44 (m, 1H), 3.09 (m, 4H).

LRMS(ESI+): Calcd for $C_{29}H_{25}ClFN_6O_6S^+$ [M+H]$^+$ 639.12, found 639.10

[Compound 130] SB1630

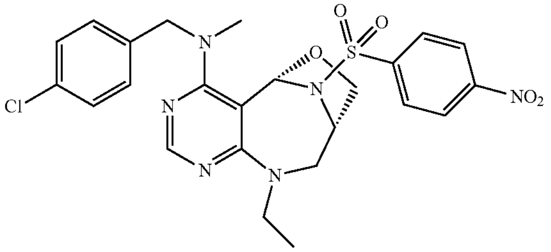

white solid;

$^1$H NMR (400 MHz, $CDCl_3$): 8.32 (d, J=8.4 Hz, 2H), 8.25 (s, 1H), 7.93 (d, J=8.4 Hz, 2H), 7.34 (d, J=8.1Hz, 2H), 7.28 (m, 2H), 6.71 (s, 1H), 4.71 (m, 1H), 4.52 (m, 2H), 3.97 (m, 1H), 3.75 (m, 1H), 3.58 (m, 1H), 3.46 (m, 1H), 3.38 (m, 1H), 3.05 (m, 1H), 2.97 (s, 3H), 1.19 (t, J=7.0 Hz, 3H);

LRMS (ESI+): Calcd for $C_{24}H_{26}ClN_6O_5S^+$ [M+H]$^+$ 545.14, found 545.05

[Compound 131] SB1631

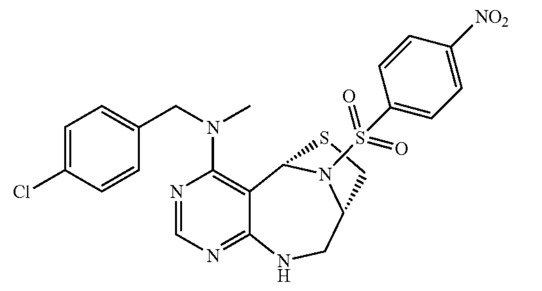

white solid;

$^{1}H$ NMR (400 MHz, $CDCl_3$): 8.25 (d, J=8.6 Hz, 2H), 8.14 (s, 1H), 7.70 (d, J=8.5 Hz, 2H), 7.42 (d, J=8.2 Hz, 2H), 7.33 (d, J=8.1Hz, 2H), 6.56 (s, 1H), 5.53 (m, 1H), 4.91 (s, 1H), 4.81 (d, J=16.1Hz, 1H), 4.58 (d, J=16.2 Hz, 1H), 3.53 (m, 1H), 3.35 (m, 1H), 3.01 (s, 3H), 2.98 (m, 1H), 2.54 (m, 1H);

LRMS (ESI+): Calcd for $C_{22}H_{22}ClN_6O_4S_2^+$ $[M+H]^+$ 533.08, found 533.15

[Compound 132] SB1632

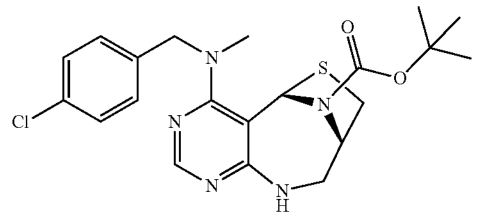

white solid;

$^{1}H$ NMR (400 MHz, $CDCl_3$): 8.12 (s, 1H), 7.30 (d, J=8.2 Hz, 2H), 7.24 (d, J=8.2 Hz, 2H), 6.75 (s, 1H), 5.52 (m, 1H), 5.14 (m, 1H), 4.69 (d, J=15.1Hz, 1H), 4.44 (d, J=15.2 Hz, 1H), 3.58 (m, 1H), 3.25 (m, 1H), 3.19 (m, 1H), 3.06 (m, 1H), 2.95 (s, 3H), 1.43 (s, 9H);

LRMS(ESI+): Calcd for $C_{21}H_{27}ClN_5O_2S^+$ $[M+H]^+$ 448.16, found 448.25

[Compound 133] SB1633

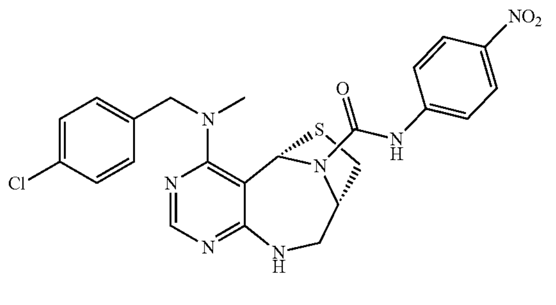

white solid;

$^{1}H$ NMR (500 MHz, $CDCl_3$): 8.28 (s, 1H), 8.17-8.13 (m, 2H), 7.38-7.33 (m, 2H), 7.30-7.27 (m, 2H), 7.25 (m, 2H), 6.96 (s, 1H), 6.67 (s, 1H), 5.43 (m, 1H), 5.25 (m, 1H), 4.42 (d, J=14.8 Hz, 2H), 3.66 (m, 1H), 3.44-3.34 (m, 2H), 3.17 (m, 1H), 2.91 (s, 3H);

LRMS (ESI+): Calcd for $C_{23}H_{23}ClN_7O_3S^+$ $[M+H]^+$ 512.13, found 512.05

[Compound 134] SB1634

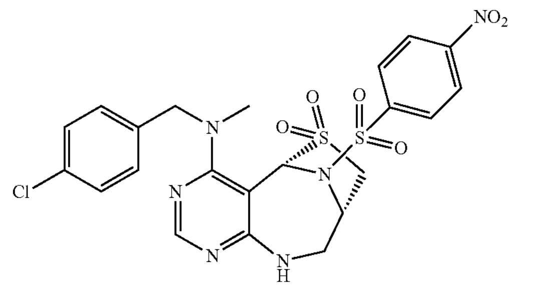

white solid;

$^{1}H$ NMR (500 MHz, $CDCl_3$): 8.33-8.25 (m, 3H), 7.52 (m, 2H), 7.45 (m, 2H), 7.36 (m, 2H), 5.79 (s, 1H), 5.53 (m, 1H), 4.94 (m, 2H), 4.48 (m, 1H), 3.59 (m, 1H), 3.42 (m, 1H), 3.10 (m, 1H), 3.03 (s, 3H), 2.92 (m, 1H);

LRMS(ESI+): Calcd for $C_{22}H_{22}ClN_6O_6S_2^+$ $[M+H]^+$ 565.07, found 565.00

[Compound 135] SB1635

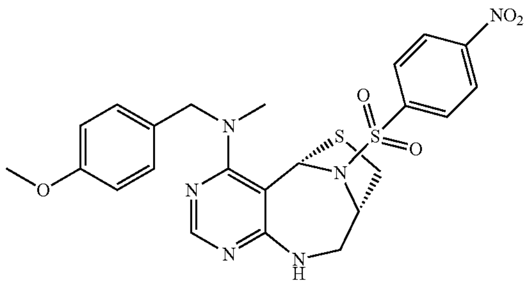

white solid;

$^{1}H$ NMR (500 MHz, $CDCl_3$): 8.18 (m, 2H), 8.14 (s, 1H), 7.56 (m, 2H), 7.33 (m, 2H), 7.01 (m, 2H), 6.56 (s, 1H), 5.62 (m, 1H), 4.63 (m, 2H), 4.55 (m, 1H), 3.87 (s, 3H), 3.84 (m, 1H), 3.63 (m, 1H), 3.47 (m, 1H), 3.07 (m, 1H), 2.99 (s, 3H);

LRMS(ESI+): Calcd for $C_{23}H_{25}N_6O_6S^+$ $[M+H]^+$ 513.16, found 513.10

[Compound 136] SB1636

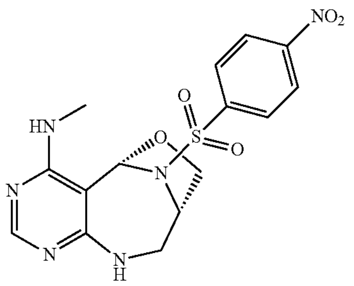

white solid;

$^{1}H$ NMR (400 MHz, $CDCl_3$): 8.42 (m, 2H), 8.13 (m, 2H), 8.12 (s, 1H), 6.46 (s, 1H), 5.02 (m, 1H), 4.89 (m, 1H), 4.44 (m, 1H), 3.92 (m, 1H), 3.65 (m, 1H), 3.44 (m, 1H), 3.21 (m, 1H), 3.07 (d, J=4.7 Hz, 3H);

LRMS(ESI+): Calcd for $C_{15}H_{17}N_6O_5S^+$ $[M+H]^+$ 393.10, found 393.00

Experimental Example 1: Confirmation of Tau Aggregation Inhibitory Effect 1-1. According to the method described in Examples 1-15 above, the expression of Venus-based bimolecular fluorescence complemented-tau (BiFC-tau) was confirmed using HEK293 human embryonic kidney cells, thereby phenotyping the phenotype-based screening was performed.

Figure 1:
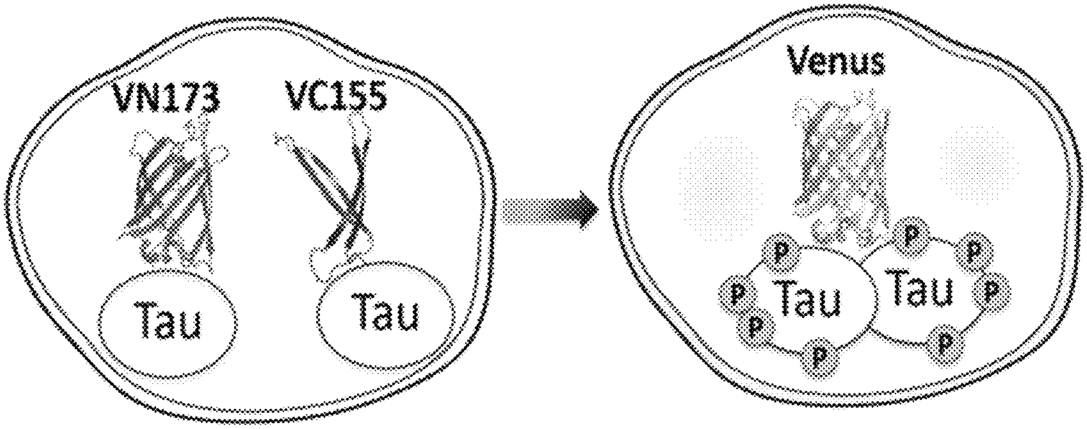
FIG. 1 shows a BiFC-tau Venus HEK293 cell system for monitoring tau aggregation according to an embodiment of the present invention.

FIG. 1 shows the BiFC-tau Venus HEK293 cell system for monitoring tau aggregation according to this example. The N-terminal Venus (VN173) and C-terminal Venus (VC155) fragment sequences are fused with the full-length human tau (hTau441) sequence to form the BiFC-tau Venus HEK293 cell system. Soluble tau dimers can be measured by monitoring the turn-on/off signal of Venus fluorescence through co-expression of the two fused vectors, hTau441-VN173 and hTau441-VC1 55.

As a stimulator of tau aggregation, thapsigargin (TG; an ER stress inducer), a direct inhibitor of sarco/endoplasmic reticulum $Ca_2^+$-ATPase, was used. This disrupts calcium homeostasis. Thapsigargin treatment induces tau dimerization (tau aggregation), which can be confirmed by BiFC-tau Venus fluorescence turn-on.

Figure 2:
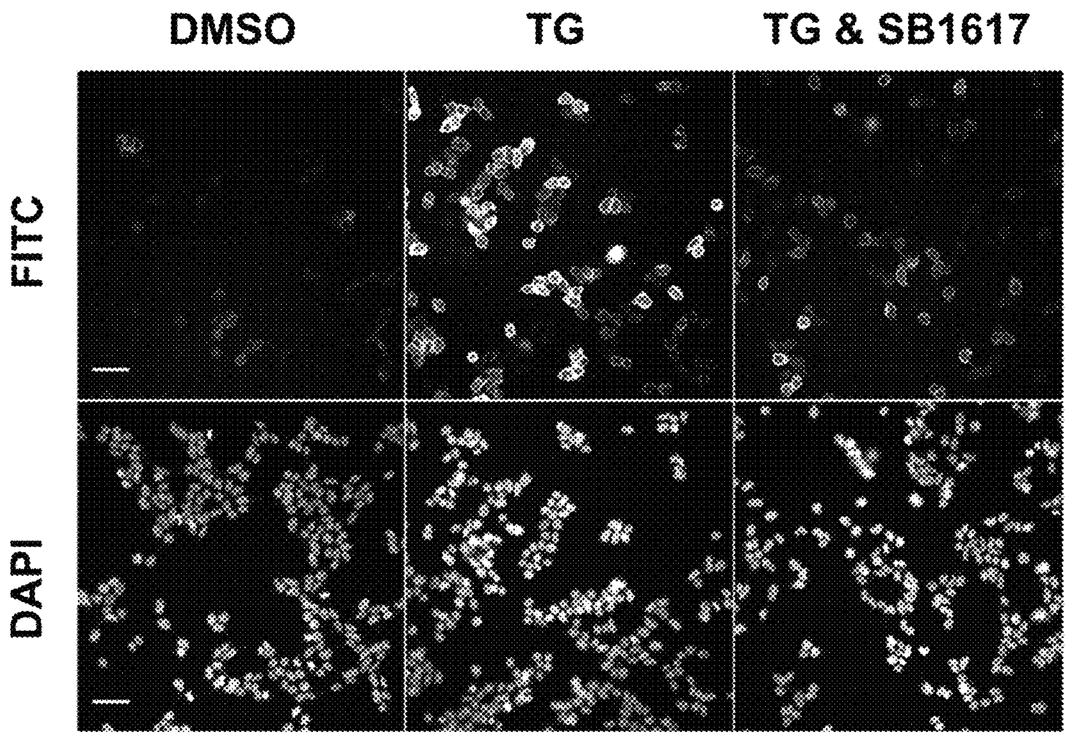
FIG. 2 is an image of observing the inhibitory effect of tau aggregation of the pyrimidodiazepine derivative (SB1617) according to the present invention using the BiFC-tau Venus HEK293 cell system.

Cells were co-treated with 80 nM thapsigargin and 10 μM of SB1617 compound for 24 hours. The FITC channel image shows fluorescence of BiFC-Venus, and the DAPI channel image shows cell nuclei in the same area as the FITC channel. As shown in FIG. 2, it was confirmed that SB1617 suppresses BiFC-Venus fluorescence induced by thapsigargin (TG) treatment, as shown in the FITC channel image.

In addition, as shown in the following Table 1 through compound screening, it was confirmed that the pyrimidodiazepine derivatives effectively inhibit BiFC-tau Venus fluorescence, and in the following Table 1, the fluorescence intensity of BiFC-tau-Venus was expressed as a percentage value when HEK293-BiFC-tau-Venus cells were co-treated with 10 μM SB16xx series compound and 80 nM thapsigargin for 24 hours.

TABLE 1

| compound number | BiFC-tau intensity (%), ($IC_{50}$) |
|---|---|
| 101 (SB1601) | 65, (9.1 ± 0.9) |
| 102 (SB1602) | 79 |
| 103 (SB1603) | 102 |
| 104 (SB1604) | 115 |
| 105 (SB1605) | 46, (5.2 ± 0.5) |
| 106 (SB1606) | 81 |
| 107 (SB1607) | 94 |
| 108 (SB1608) | 105 |
| 109 (SB1609) | 84 |
| 110 (SB1610) | 130 |
| 111 (SB1611) | 110 |
| 112 (SB1612) | 90 |
| 113 (SB1613) | 71 |
| 114 (SB1614) | 47, (6.9 ± 0.9) |
| 115 (SB1615) | 99 |
| 116 (SB1616) | 135 |
| 117 (SB1617) | 36, (1.9 ± 0.5) |
| 118 (SB1618) | 55, (7.6 ± 1.2) |
| 119 (SB1619) | 56, (4.6 ± 2.1) |
| 120 (SB1620) | 81 |
| 121 (SB1621) | 51, (6.6 ± 0.6) |
| 122 (SB1622) | 81 |
| 123 (SB1623) | 78 |
| 124 (SB1624) | 50, (8.1 ± 0.6) |
| 125 (SB1625) | 98 |
| 126 (SB1626) | 100 |
| 127 (SB1627) | 100 |
| 128 (SB1628) | 95 |
| 129 (SB1629) | 70 |

TABLE 1-continued

| compound number | BiFC-tau intensity (%), ($IC_{50}$) |
|---|---|
| 130 (SB1630) | 70 |
| 131 (SB1631) | 98 |
| 132 (SB1632) | 80 |
| 133 (SB1633) | 94 |
| 134 (SB1634) | 100 |
| 135 (SB1635) | 57 |
| 136 (SB1636) | 10 |

In particular, it was found that SB1617 effectively suppressed BiFC-tau Venus fluorescence with a half-maximal inhibitory concentration ($IC_{50}$) of 1.9 μM.

Additionally, to confirm the aggregation effect depending on the dose, the change in Venus fluorescence intensity was examined when BiFC-tau Venus HEK293 cells were co-treated with various concentrations of SB1617 or SB1607 and 80 nM TG for 20 hours. As a result, as shown in FIG. 3, it was confirmed that the effect of SB1617 was dose dependent. On the other hand, when the chemical structure of SB1617 was simplified by removing the aromatic ring from the sulfonamide group of SB1617 (SB1607), the activity was lost, indicating that the inhibitory effect of tau aggregation depends on specific compound-target interactions.

1-2. According to the immunoblotting method described in Examples 1-7, BiFC-tau venus HEK293 cells were treated with SB1617, SB1607, and 80 nM thapsigargin for 20 hours, and total tau (Tau5) and phospho-tau (S199, T231) levels were measured. As a result, as shown in FIG. 4, it was confirmed that thapsigargin treatment increased the total tau level as well as p-tau, whereas SB1617 treatment decreased all tau levels.

1-3. Increase in total tau levels upon thapsigargin treatment appears to be due to stimulation of protein synthesis. Similarly, expression of aggregation-prone proteins such as prions and mutant tau was promoted by ER stress. In order to exclude the influence of transcriptional changes upon stress stimulation, flow cytometric analysis was performed using DsRed-IRES-tau EGFP, a bicistronic cell containing an internal ribosome entry site (IRES) between the DsRed and tau EGFP sequences, according to the method described in Examples 1-6 above. As a result, as shown in FIG. 5, it was confirmed that the change in the EGFP-to-DsRed fluorescence ratio during compound treatment represents the change in tau level through the clearance pathway regardless of transcriptional alteration.

In addition, as shown in FIGS. 6 and 7, the EGFP-to-DsRed signal ratio was slightly increased when thapsigargin was treated, but the EGFP-to-DsRed signal ratio decreased, indicating that SB1617 promoted tau clearance and regulated tau protein homeostasis when thapsigargin and SB1617 were co-treated. Accordingly, it was found that SB1617 according to the present invention regulates protein homeostasis, thereby inhibiting the aggregation of tau protein, which is overexpressed and prone to aggregation.

Experimental Example 2: Target Protein Analysis 2-1. In order to identify the mechanism of action of the pyrimidodiazepine derivatives according to the present invention, target protein analysis was performed according to the TS-FITGE method described in Examples 1-8

As a result, as shown in FIG. 8, several red spots appeared on the 2D gel electrophoresis image of the sample treated at a higher temperature, indicating that the thermal stability of the protein was improved by the specific interaction with SB1617. However, these proteins were not stabilized by inactive compounds or vehicles. The red spots also disappeared when thermal denaturation was completely gone. The heat stable proteins (red spots) were identified through mass spectrometry, and as a result, it was confirmed that they were DNAJC3 and PDIA3.

2-2. In order to confirm the specific binding between the compound (SB1617) according to the present invention and DNAJC3 and PDIA3, the CETSA of Examples 1-9 and the pull-down assay of Examples 1-10 were performed. As a result, as shown in FIGS. 9 and 10, it was confirmed that the compound (SB1617) according to the present invention specifically binds to DNAJC3 and PDIA3.

Additionally, it was confirmed whether SB1617 directly binds to PDIA3 and DNAJC3 through surface plasmon resonance (SPR) of Examples 1-11. As a result, as shown in FIG. 11, it was confirmed that the degree of binding to PDIA3 (FIG. 11A) and DNAJC3 (FIG. 11B) increased as the concentration of SB1617 increased. Through the above results, it was found that the compound (SB1617) according to the present invention binds directly to DNAJC3 and PDIA3.

Experimental Example 3: Verification of Interaction with Target Protein 3-1. According to the method described in Examples 1-4 above, siRNAs that inhibit the expression of PDIA3 and DNAJC3 were introduced into BiFC-tau cells and DsRed-IRES-EGFP-tau HEK293 cells, and 48 hours after introduction, they were treated with 100 nM TG, and then, changes in tau-Venus intensity, p-tau level, and EGFP-to-DsRed intensity ratio were measured. At this time, BiFC-tau cells were treated for 20 hours and DsRed-IRES-EGFP-tau HEK293 cells were treated for 18 hours. As a result, as shown in FIGS. 12 to 14, it was confirmed that when the expression of PDIA3 and DNAJC3 was suppressed, the tau-Venus intensity, p-tau level, and EGFP-to-DsRed intensity ratio decreased, resulting in the same phenotype as the intracellular activity of SB1617.

3-2. Since PDIA3 is a known PDI reductase, PDIA3 knockdown should promote PDI oxidation. Therefore, in order to evaluate whether the interaction of PDIA3 and SB1617 can enhance PDI oxidation, the PEG-maleimide modification assay described in Examples 1-12 was performed. More specifically, BiFC-tau HEK293 cells were treated with 200 nM TG and 40 μM SB1617 for 3.5 hours. As controls for the reduced and oxidized forms of PDI, 10 mM 1,4-dithiothreitol (DTT) and 5 mM tetramethylazodicarboxamide (DA) were each added to the cells for 15 minutes. Free thiols in cysteine are pre-alkylated to low molecular weight maleimide molecules, leaving oxidized or disulfide-linked cysteines. The cysteine was alkylated with high molecular weight PEG-maleimide (5 kDa) after a disulfide reduction step. Maleimides with two different molecular weights allow the bands of oxidized and reduced forms of PDI to be readily separated by electrophoresis. As a result, as shown in FIG. 15, it was confirmed that the PDI form was significantly converted from the reduced form to the oxidized form when SB1617 and thapsigargin were co-treated, compared to the case where thapsigargin was treated alone. From this, it was found that SB1617 disrupts the cellular function of PDIA3.

Experimental Example 4: Prevention Effect on PERK Signaling Inhibition 4-1. Both PDIA3 and DNAJC3 have been reported to inhibit the activation of protein kinase-like endoplasmic reticulum kinase (PERK) signaling, an ER stress sensor on the ER membrane. To confirm the functional role of DNAJC3 and PDIA3 in suppressing PERK signaling, siRNA was introduced into BiFC-tau HEK293 cells, and 48 hours after introduction, 200 nM TG was treated for 6 hours, and then the alteration of the PERK downstream pathway was confirmed through immunoblot analysis.

As a result, as shown in FIG. 16, it was confirmed that inhibition of PDIA3 or DNAJC3 suppresses the abnormal increase of p-tau upon thapsigargin treatment in tau-overexpressing cells, and phosphorylation of eIF2a (eukaryotic translation initiation factor), which inhibits the functions of PDIA3 and DNAJC3 in the PERK signaling pathway, and downstream signals of PERK including ATF4 were upregulated.

4-2. PDIA3 and DNAJC3 play a role in regulating tau aggregation by inhibiting the PERK signaling pathway. Accordingly, human neuroblastoma SH-SY5Y cells were treated with 10 μM SB1617, treated with or without thapsigargin, and PERK activation was confirmed over time. As a result, as shown in FIG. 17, it was confirmed that SB1617 prolonged PERK activation, continuously maintained the levels of p-PERK and p-eIF2a, and upregulated ATF4 under stress conditions induced by thapsigargin treatment.

On the other hand, as shown in FIG. 18, in the absence of cell stress, activation of downstream PERK signaling by SB1617 was not significant. The stress-response potency of SB1617 may be due to upregulation of PDIA3 and DNAJC3 levels or changes in the redox state of partner proteins under ER stress conditions.

Experimental Example 5: Checking Protein Homeostasis Regulatory Ability 5-1. Phosphorylation of eIF2a results in the inhibition of translation of most mRNAs, significantly reducing the ER load, enabling cells to survive. To assure this, SH-SY5Y cells were treated with 10 μM SB1617 for directed time, and then the newly synthesized protein was labeled with 10 μg/mL furomycin for 10 minutes and visualized by anti-furomycin antibody staining. As a result, as shown in FIG. 19, it was found that protein synthesis was temporarily suppressed during thapsigargin treatment and recovered at a later moment. On the other hand, when SB1617 was treated with thapsigargin, inhibition of protein synthesis was enhanced and extended, consistent with the level of p-eIF2a.

5-2. When 10 μM SB1617 was treated in the presence or absence of 200 nM TG and 20 μg/mL cycloheximide in HEK293 BiFC-tau cells for 8 hours, the total tau level was confirmed through immunoblotting analysis. As a result, as shown in FIGS. 20 and 21, when HEK293 BiFC-tau cells were pre-treated with cycloheximide, a translation inhibitor, SB1617 treatment did not cause a significant change in tau level.

5-3. ATF4 is a transcription factor, which rises during eIF2a-phosphorylation and upregulates genes related to autophagy and oxidation/reduction control as a recovery mechanism during ER stress. To assure this, 5 μM SB1617 was treated in SH-SY5Y cells for 8 hours in the presence or absence of 1 μM thapsigargin, and then autophagy-related genes regulated by ATF4 were identified with RT-qPCR.

As a result, as shown in FIG. 22, it was confirmed that the treatment of SB1617 and thapsigargin increased the transcription level of autophagy-related genes regulated by ATF4 compared to cells treated with tapsigargin alone. From the above results, it was found that SB1617 promoted autophagy.

5-4. When 5 μM SB1617 was treated in HEK293 BiFC-tau cells for 6 hours in the presence or absence of 500 nM TG, conversion from LC3-I to LC3-II and p62 levels were confirmed through immunoblot analysis, and as a result with FIG. 23, conversion from light chain 3-1 (LC3-I) to LC3-II was confirmed.

5-5. The total tau level of treatment with SB1617 and TG in the absence and presence of 3-methyl adenine (3-MA, authophagy inhibitor) and bafilomycin A1 (Baf) in HEK293 BiFC-tau cells was confirmed through immunoblot analysis. As a result, as shown in FIGS. 24 and 25, when the autophagy process is blocked by the treatment of 3-methyladenine and bafilomycin A1 to interfere with the initial and late autophagy stages, the effect of SB1617 on the reduction of tau level is reduced, but does not completely diminish. This means that the SB1617 effect in tau clearance is less affected than the translation regulation characteristics for protein homeostatic control.

5-6. From the results of Test Examples 5-1 to 5-5, it was hypothesized that if SB1617, a pyrimidiazepine derivative from this invention, regulates protein homeostasis, it will be able to effectively control the level of other proteins that tend to be folded and accumulated incorrectly under ER stress conditions. To confirm this, changes in the level of other aggregation-oriented proteins according to SB1617 treatment were confirmed.

As a result, as shown in FIG. 26, it was revealed that the mutation levels of tau P301L, Htt-Q74 and SOD (G93A) were downregulated according to SB1617 treatment. Tau P301L is found in FTD patients with Parkinson's disease and is known to accelerate tau aggregation and accumulation in the mouse brain. Htt-Q74 refers to a polyglutamine dilated mutation that causes Huntington's disease. The SOD1 (G93A) mutation level is one of the clinical characteristics of ALS patients.

Experimental Example 6: Validation of Efficacy on TBI Mouse Models 6-1. In order to evaluate the suitability of the compound (SB1617) according to this invention in vivo, pharmacokinetic properties and blood-brain barrier penetration properties were identified using male ICR mice according to the methods described in Examples 1-15 and 1-16.

As a result, as shown in FIG. 27 and Table 2 below, intraperitoneal injected blood SB1617 showed appropriate pharmacodynamic behavior with a half-life of about 6.6 hours and sufficient blood-brain barrier crossing.

TABLE 2

| Parameters | I.V., 5 mg/kg | I.P., 5 mg/kg |
|---|---|---|
| $T_{max}$ (h) | NA | 1.67 ± 2.02 |
| $C_{max}$ (μg/mL) | NA | 0.857 ± 0.339 |
| $T_{1/2}$ (h) | 5.51 ± 1.86 | 6.57 ± 0.0563 |
| $AUC_t$ (μg · h/mL) | 4.19 ± 0.112 | 6.07 ± 2.81 |
| $AUC_\infty$ (μg · h/mL) | 4.49 ± 0.15 | 5.65 ± 3.32 |
| CL (L/h/kg) | 1.12 ± 0.038 | NA |
| $V_{ss}$ (L/kg) | 6.27 ± 0.928 | NA |

NA, not applicable

In addition, as shown in FIG. 28 and Table 3, it was confirmed that at least 50% of SB1617 was detected in the brain compared to plasma.

TABLE 3

| Time | Concentration (ng/mL) | | |
|---|---|---|---|
| (h) | Plasma | Brain tissue | Brain/Plasma ratio |
| 0.5 | 885 ± 187 | 421 ± 58.2 | 0.50 ± 0.14 |
| 3 | 92.4 ± 29.8 | 55.9 ± 5.00 | 0.66 ± 0.21 |

6-2. Traumatic brain injury (TBI) leads to the development of tau and Aβ pathologies combined with ER stress, and causes severe brain damage by impairing neural function and cognitive ability. The potential therapeutic effect of SB1617 on TBI mice was identified by identifying tau, p-tau, oxidative stress, ER stress, neuroinflammatory, neuronal viability, and behavior improvement levels, and the design for the experiment is schematically shown in FIG. 29.

Firstly, immunofluorescence staining of the ipsilateral hippocampal CA1 and cortex was performed to check for improvement of ER stress and oxidative stress, and as shown in FIGS. 30 and 31, ER stress and oxidative stress were significantly increased in the TBI mouse model, but these symptoms were confirmed when SB1617 was administered to TBI mice (5 mg/kg, 2 times a day).

6-3. Immunofluorescence staining of ipsilateral hippocampal CA1 and cortex was performed to confirm changes in total tau and p-tau levels, and as shown in Figure. 32 and 33, after 24 hours of TBI, total tau and p-tau levels increased rapidly in hippocampa and cortex areas. However, it was confirmed that these symptoms were improved when SB1617 was administered to TBI mice (5 mg/kg weight, 2 times a day).

6-4. Immunofluorescence staining of ipsilateral hippocampal CA1 and cortex was performed to confirm nerve protection activity, and as shown in FIG. 34, neuronal death was observed after 3 days of TBI, but these symptoms could be confirmed when SB1617 was administered to TBI mice (5 mg/kg, 2 times a day).

In addition, neurologic severity score (NSS) was evaluated according to SB1617 treatment, and as shown in FIG. 35, SB1617 maintained nerve protection activity even after 1, 4, 24, 48, 72 hours and 7 days after TBI.

6-5. In order to check the behavior improvement level, the pole climbing test of Example 1-24 was conducted, and as shown in FIG. 36, in the case of mice administered SB1617 after TBI induction, both the time to turn the head downward (FIG. 36A) and the time to descend the pole (FIG. 36B) were significantly reduced compared to mice administered only with those administered with vehicle.

6-6. Immunofluorescence staining of ipsilateral hippocampal CA1 and cortex was performed to check the level of neuroinflammatory improvement, and as shown in FIG. 37, Iba-1 levels were increased in hippocampa and cortex areas after 72 hours, but SB1617 could be improved 2 kg/day in TBI symptoms.

In addition, the level of microglial activation was confirmed in ipsilateral hemisphere, and as shown in FIG. 38, it was confirmed that the activity of microglial cells was improved in mice administered SB1617 after TBI.

6-7. Western blotting analysis confirmed the transition from p62, LC3-I to LC3-II, BDNF, and CHOP levels in ipsileral perilament cortex of mice treated with vehicle or SB1617 at 12 and 24 hours after sham surgery or TBI induction. As a result, as shown in FIG. 39, PERK stimulation by SB1617 was demonstrated by an increase in p62 protein level during SB1617 treatment, and p62 protein level was lower in the TBI group than in the sham group. In addition, it was confirmed that the conversion rate from LC3-I to LC3-II was improved when SB1617 was administered, which means that SB1617 promotes autophagy in TBI mice.

Experimental Example 7: Validation of Efficacy in Acute Alzheimer's Mouse Model 7-1. Potential therapeutic effect of SB1617 in an acute Alzheimer's mouse model was identified, and the design for the experiment is schematically shown in FIG. 40.

7-2. As a result of confirming the treatment efficacy through an Acquisition test, as shown in FIG. 41, it was confirmed that the learning ability according to drug administration appeared in the order of WT >Donepezil >SB-1617>Vehicle. On the other hand, as a result of confirming the difference in learning ability according to the route of administration, as shown in FIG. 42, it was confirmed that the effect of the excipient according to the route of administration was not significant.

7-3. As a result of confirming the treatment efficacy through a probe test, after removing the platform, it was performed by recording how many times the mouse passed the position where the platform was First, as a result of comparing the time to reach the platform, as shown in FIG. 43, when compared to the vehicle, it was confirmed that the SB-1617 administered group showed a significantly lower value, showing a result close to the WT.

Next, as a result of comparing the number of times passing the virtual platform, as shown in FIG. 43, when compared to the vehicle, it was confirmed that the SB-1617 administered group showed a significantly higher value, showing a result close to the WT.

Next, as a result of comparing the percentage (%) of the time spent in the quadrant where the platform exists, it was confirmed that the group administered with SB-1617 remembered the location of the platform well.

In addition, as a result of confirming the number of times of entering the SW quadrant space where the platform existed, as shown in FIG. 43, when compared to the vehicle, it was confirmed that the group administered with SB-1617 showed a significantly higher value, showing a result close to that of WT.

The description of the present invention described above is for illustrative purposes, and those skilled in the art to which the present invention pertains will understand that it can be easily modified into other specific forms without changing the technical spirit or essential characteristics of the present invention. Therefore, the Examples described above should be understood as illustrative in all respects and not limiting.

What is claimed is:

1. A compound represented by the following Formula 1, or a pharmaceutically acceptable salt thereof:

[Formula 1]

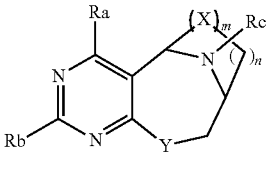

wherein

X is $CH_2$; CO; $COCF_3$; NH; $NCH_3$; O; or $SO_2$;

Y is O; S; SO; $SO_2$; or NRy;

m is an integer of 0 or 1;

n is an integer of 0, 1 or 2;

Ry is hydrogen; $C_1$-$C_{20}$ linear or branched alkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; —COR'; —$SO_2$R'; —SOR'; —COOR'; —CONHR'; or —CONR'R";

Ra is hydrogen; $C_1$-$C_{20}$ linear or branched alkyl; $C_1$-$C_{20}$ linear or branched alkenyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; 5- to 6-membered heterocyclyl containing 1 to 2 N atoms in which any one or more hydrogens are substituted with $C_1$-$C_5$ linear or branched alkyl, or 6- to 10-membered aryl; or —$NRa_1Ra_2$;

Rb is hydrogen; $C_1$-$C_{20}$ linear or branched alkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; —NR'R"; —SR'; —$SO_2$R'; or —SOR';

Rc is hydrogen; $C_1$-$C_{20}$ linear or branched alkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy branched alkoxy, and azide; —COR'; —SOR'; —$SO_2R'$; —COOR'; —CONHR'; or —CONR'R";

$Ra_1$ and $Ra_2$ of —$NRa_1Ra_2$ in the definition of Ra are each independently hydrogen; $C_1$-$C_{20}$ linear or branched alkyl; $C_1$-$C_{10}$ linear or branched aminoalkyl in which at least one hydrogen is substituted with an amine; arylalkyl in which any one hydrogen of $C_1$-$C_{10}$ linear or branched alkyl is substituted with $C_6$-$C_{20}$ aryl substituted with one or more substituents selected from the group consisting of halogen, $C_1$-$C_{10}$ linear or branched alkyl, $C_1$-$C_{10}$ linear or branched alkoxy, and azide; heteroarylalkyl in which any one hydrogen of $C_1$-$C_5$ alkyl is substituted with 6-membered heteroaryl containing one N; phenoxyalkyl in which any one hydrogen of $C_1$-$C_{10}$ linear or branched alkyl is substituted with a phenoxy group; $C_6$-$C_{20}$ aryl unsubstituted or substituted with one or more selected from the group consisting of $C_1$-$C_{10}$ linear or branched alkoxy and azide; —COR'; —$SO_2R'$; —SOR'; —COR'R"; or —COOR'; and R' and R" in the definitions of Ry, Rb, Rc, $Ra_1$ and $Ra_2$ are each independently hydrogen; $C_1$-$C_{10}$ linear or branched alkyl; $C_3$-$C_{10}$ cycloalkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkynyl, $C_1$-$C_{10}$ linear or branched alkoxy, and nitro; benzyl; 5- to 20-membered heteroaryl containing 1 to 3 heteroatoms selected from N, O and S.

2. The compound or a pharmaceutically acceptable salt thereof according to claim 1, wherein the compound of Formula 1 is represented by any one of the following Formulas 2 to 10:

[Formula 2]

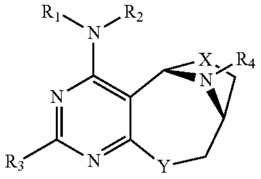

[Formula 3]

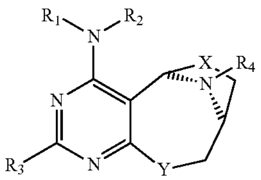

[Formula 4]

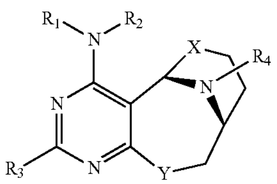

[Formula 5]

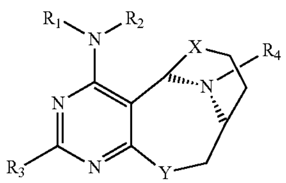

-continued

[Formula 6]

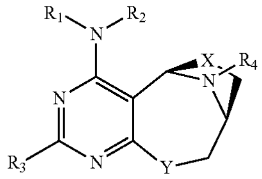

[Formula 7]

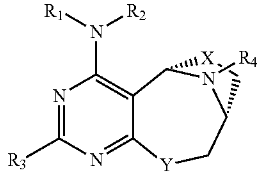

[Formula 8]

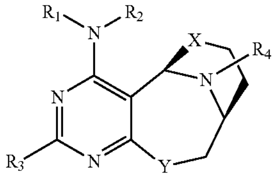

[Formula 9]

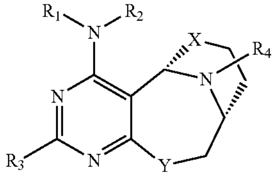

[Formula 10]

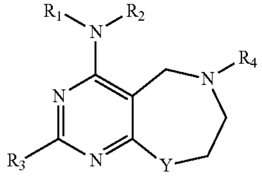

wherein

X and Y are the same as defined in claim 1;

$R_1$ and $R_2$ are each independently hydrogen; $C_1$-$C_{20}$ linear or branched alkyl; $C_1$-$C_{10}$ linear or branched aminoalkyl in which at least one hydrogen is substituted with an amine; $C_6$-$C_{20}$ aryl-$C_1$-$C_{10}$ linear or branched alkyl in which any one hydrogen of $C_1$-$C_{10}$ linear or branched alkyl is substituted with $C_6$-$C_{20}$ aryl substituted with one or more substituents selected from the group consisting of halogen, $C_1$-$C_{10}$ linear or branched alkyl, $C_1$-$C_{10}$ linear or branched alkoxy, and azide; 6-membered heteroaryl-$C_1$-$C_5$ alkyl in which any one hydrogen of $C_1$-$C_5$ alkyl is substituted with a 6-membered heteroaryl containing one N; phenoxy-$C_1$-$C_{10}$ linear or branched alkyl in which any hydrogen of $C_1$-$C_{10}$ linear or branched alkyl is substituted with a phenoxy group; $C_6$-$C_{20}$ aryl unsubstituted or substituted with one or more substituents selected from the group consisting of $C_1$-$C_{10}$ linear or branched alkoxy and azide; —COR'; —$SO_2R'$; —SOR'; —COR'R"; or —COOR';

$R_3$ is hydrogen; $C_1$-$C_{20}$ linear or branched alkyl; $C_6$-$C_{20}$ aryl unsubstituted or substituted with one or more substituents selected from the group consisting of halogen, $C_1$-$C_{10}$ linear or branched alkyl, $C_1$-$C_{10}$ linear or branched alkoxy, and azide; —NR'R"—SR'; —$SO_2R'$; or —SOR';

$R_4$ is hydrogen; $C_1$-$C_{20}$ linear or branched alkyl; $C_6$-$C_{20}$ aryl unsubstituted or substituted with one or more selected from the group consisting of halogen, $C_1$-$C_{10}$ linear or branched alkyl, $C_1$-$C_{10}$ linear or branched alkoxy, and azide; —COR'; —SOR'; —$SO_2$R'; —COOR'; —CONHR'; or —CONR'R";

R' and R" in the definitions of $R_1$ to $R_4$ are each independently hydrogen; $C_1$-$C_{10}$ linear or branched alkyl; $C_3$-$C_{10}$ cycloalkyl; $C_6$-$C_{20}$ aryl unsubstituted or substituted with one or more selected from the group consisting of halogen, $C_1$-$C_{10}$ linear or branched alkyl, $C_1$-$C_{10}$ linear or branched alkynyl, $C_1$-$C_{10}$ linear or branched alkoxy and nitro; benzyl; 5- to 20-membered heteroaryl containing 1 to 3 heteroatoms selected from N, O and S.

3. The compound or a pharmaceutically acceptable salt thereof according to claim 2, wherein X is O or $SO_2$;

Y is NRy, wherein Ry is hydrogen, $C_1$-$C_{10}$ linear or branched alkyl, or —COR', wherein R' is the same as defined in claim 1;

$R_1$ is $C_6$-$C_{20}$ aryl-$C_1$-$C_{10}$ linear or branched alkyl in which any one hydrogen of $C_1$-$C_{10}$ linear or branched alkyl is substituted with $C_6$-$C_{20}$ aryl substituted with one or more substituents selected from the group consisting of halogen, $C_1$-$C_{10}$ linear or branched alkyl, $C_1$-$C_{10}$ linear or branched alkoxy, and azide;

$R_2$ is hydrogen or $C_1$-$C_{20}$ linear or branched alkyl;

$R_3$ is hydrogen or $C_1$-$C_{20}$ linear or branched alkyl; and $R_4$ is —SOR' or —$SO_2$R', wherein R' is the same as defined in claim 2.

4. The compound or a pharmaceutically acceptable salt thereof according to claim 3, wherein $R_1$ is a group represented by the following Formula 11, and $R_4$ is a group represented by the following Formula 12:

[Formula 11]

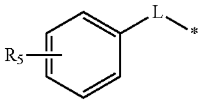

[Formula 12]

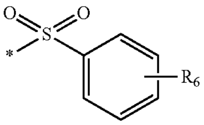

wherein

L is a single bond or $C_1$-$C_{10}$ linear or branched alkyl;

$R_5$ is halogen; G1-$C_{20}$ linear or branched alkyl; $C_1$-$C_{10}$ linear or branched alkoxy; azide; or $C_6$-$C_{20}$ aryl unsubstituted or substituted with one or more substituents selected from the group consisting of $C_1$-$C_{10}$ linear or branched alkyl and halogen;

$R_6$ is halogen, $C_1$-$C_{10}$ linear or branched alkyl, $C_1$-$C_{10}$ linear or branched alkynyl, $C_1$-$C_{10}$ linear or branched alkoxy, or nitro.

5. The compound or a pharmaceutically acceptable salt thereof according to claim 2, wherein the compound is represented by Formula 2.

6. The compound or a pharmaceutically acceptable salt thereof according to claim 1, wherein the compound of Formula 1 is represented by the following Formula 13:

[Formula 13]

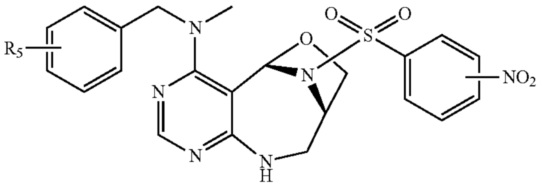

wherein $R_5$ is halogen; $C_1$-$C_{20}$ linear or branched alkyl; $C_1$-$C_{10}$ linear or branched alkoxy; azide; or $C_6$-$C_{20}$ aryl unsubstituted or substituted with one or more substituents selected from the group consisting of $C_1$-$C_{10}$ linear or branched alkyl and halogen.

7. The compound or a pharmaceutically acceptable salt thereof according to claim 6, wherein $R_5$ is halogen; or azide.

8. A compound selected from the group consisting of the following compounds 101 to 103, 105 to 125, and 127:

101

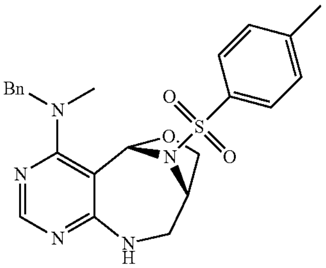

102

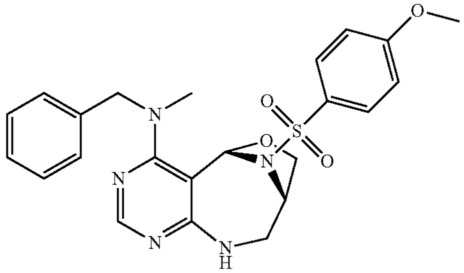

103

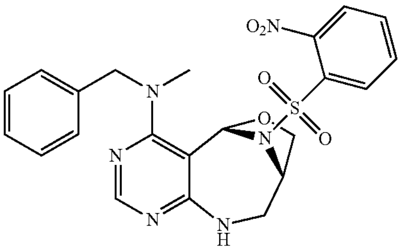

-continued
105
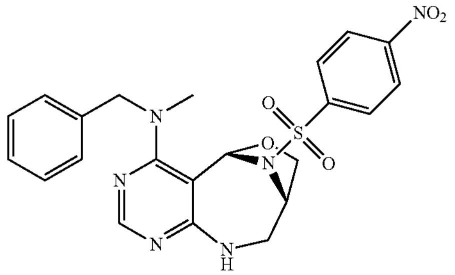
106
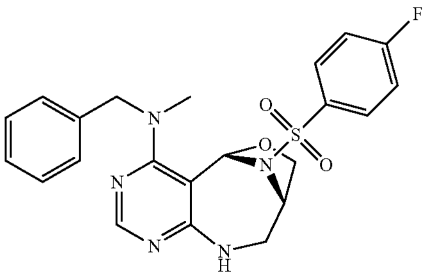
107
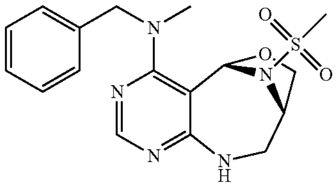
108
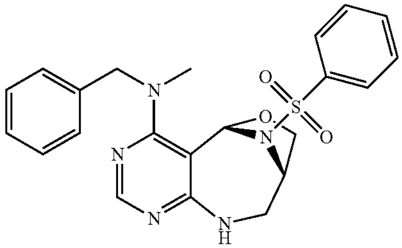
109
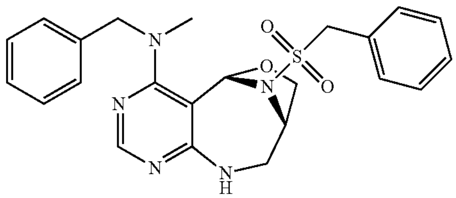
110
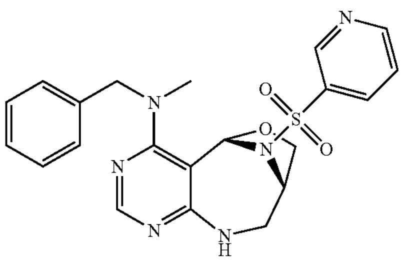
-continued
111
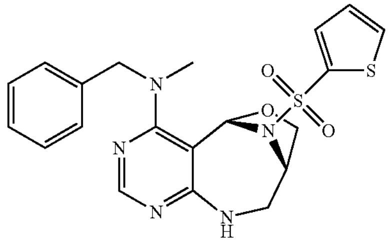
112
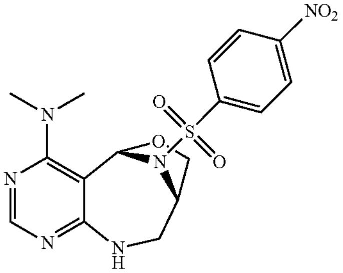
113
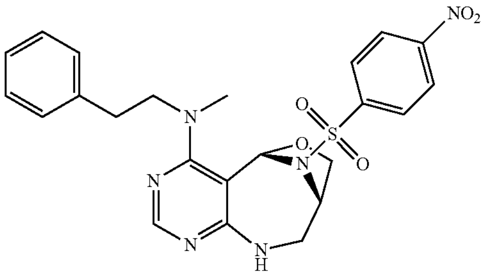
114
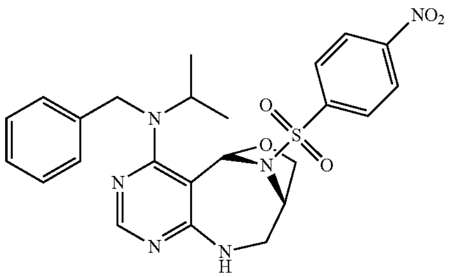
115
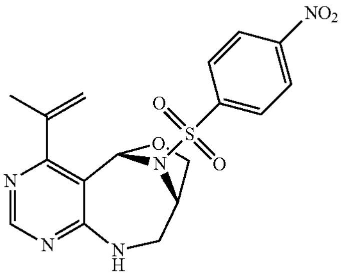

116
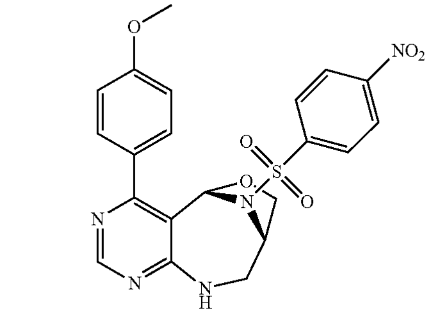
117
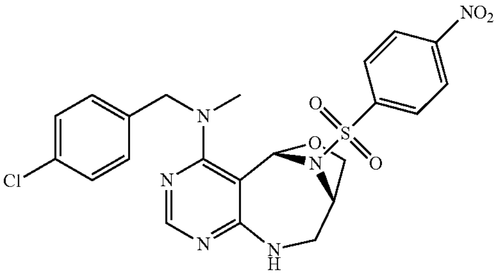
118
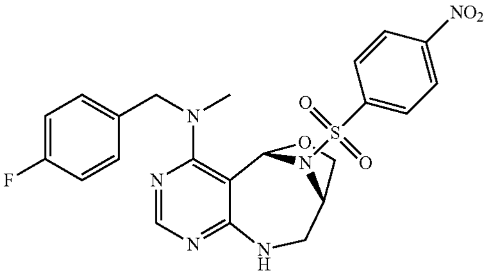
119
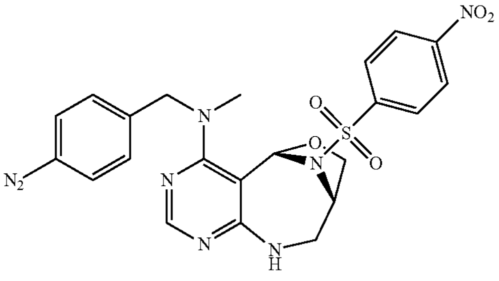
120
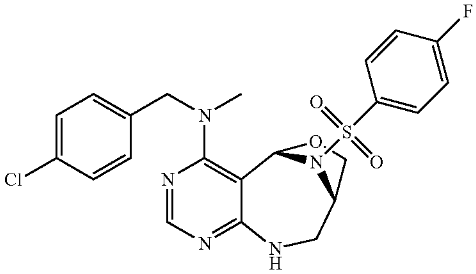
121
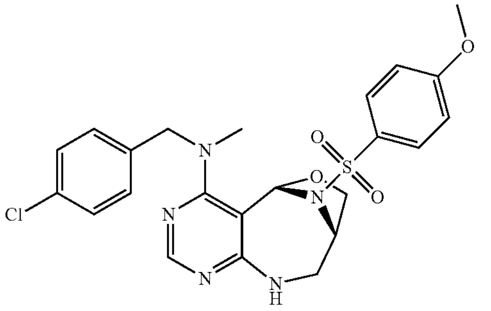
122
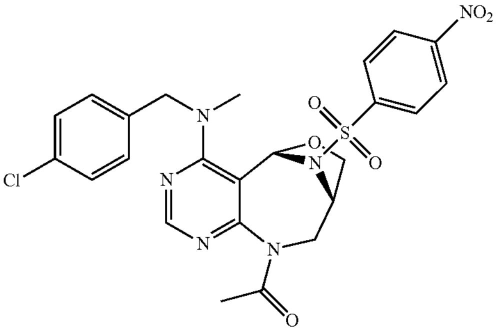
123
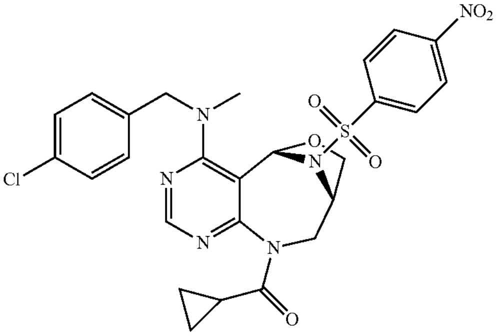
124
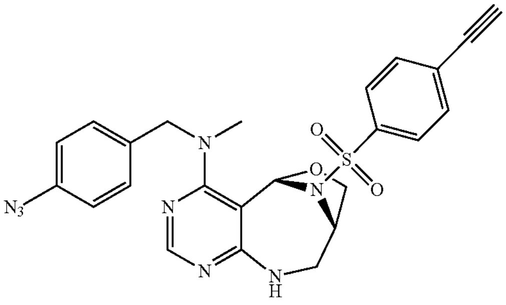
125
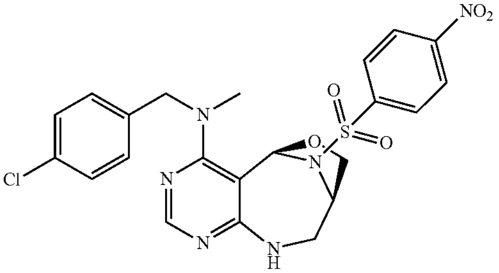

-continued

127

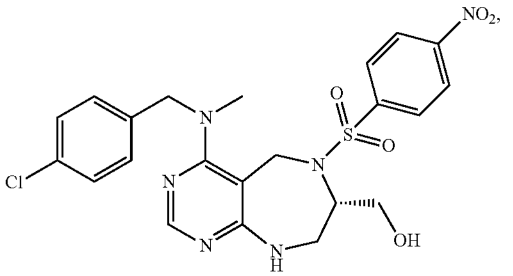

or a pharmaceutically acceptable salt thereof.

9. A tau aggregation inhibitor comprising the compound or a pharmaceutically acceptable salt thereof according to claim 1, which inhibits tau aggregation by preventing inhibition of PERK signal transduction through binding with PDIA3, DNAJC3, or both.

10. A pharmaceutical composition for preventing or treating tauopathies, comprising the compound or a pharmaceutically acceptable salt thereof according to claim 1.

11. The pharmaceutical composition for preventing or treating tauopathies according to claim 10, wherein the tauopathies is any one selected from the group consisting of Alzheimer's disease, frontotemporal dementia, progressive supranuclear palsy, traumatic brain injury, Pick's disease, Chronic traumatic encephalopathy, Argyrophilic grain disease, corticobasal degeneration, Parkinson's disease, Huntingtin's disease, and Amyotrophic lateral sclerosis.

12. A pharmaceutical composition for preventing or treating tauopathies, comprising the compound or a pharmaceutically acceptable salt thereof according to claim 8.

13. The pharmaceutical composition for preventing or treating tauopathies according to claim 12, wherein the tauopathies is any one selected from the group consisting of Alzheimer's disease, frontotemporal dementia, progressive supranuclear palsy, traumatic brain injury, Pick's disease, Chronic traumatic encephalopathy, Argyrophilic grain disease, corticobasal degeneration, Parkinson's disease, Huntingtin's disease, and Amyotrophic lateral sclerosis.

14. A method for preventing or treating tauopathies, comprising administering to a subject in need thereof the compound or a pharmaceutically acceptable salt thereof according to claim 1.

15. The method for preventing or treating tauopathies according to claim 14, wherein the tauopathies is any one selected from the group consisting of Alzheimer's disease, frontotemporal dementia, progressive supranuclear palsy, traumatic brain injury, Pick's disease, Chronic traumatic encephalopathy, Argyrophilic grain disease, corticobasal degeneration, Parkinson's disease, Huntingtin's disease, and Amyotrophic lateral sclerosis.

* * * * *

SEQUENCE LISTING

```
<160> NUMBER OF SEQ ID NOS: 8

<210> SEQ ID NO 1
<211> LENGTH: 19
<212> TYPE: RNA
<213> ORGANISM: Artificial Sequence
<220> FEATURE:
<223> OTHER INFORMATION: synthetic sequence

<400> SEQUENCE: 1

cguccuucac aucucacua                                               19


<210> SEQ ID NO 2
<211> LENGTH: 19
<212> TYPE: RNA
<213> ORGANISM: Artificial Sequence
<220> FEATURE:
<223> OTHER INFORMATION: synthetic sequence

<400> SEQUENCE: 2

uagugagaug ugaaggacg                                               19


<210> SEQ ID NO 3
<211> LENGTH: 19
<212> TYPE: RNA
<213> ORGANISM: Artificial Sequence
<220> FEATURE:
<223> OTHER INFORMATION: synthetic sequence

<400> SEQUENCE: 3

gaaauaccag gaccaguuu                                               19


<210> SEQ ID NO 4
<211> LENGTH: 19
<212> TYPE: RNA
<213> ORGANISM: Artificial Sequence
<220> FEATURE:
<223> OTHER INFORMATION: synthetic sequence
```

-continued

```
<400> SEQUENCE: 4

aaacuggucc ugguauuuc                                               19


<210> SEQ ID NO 5
<211> LENGTH: 19
<212> TYPE: RNA
<213> ORGANISM: Artificial Sequence
<220> FEATURE:
<223> OTHER INFORMATION: synthetic sequence

<400> SEQUENCE: 5

cugcuauagc cuuccuuga                                               19


<210> SEQ ID NO 6
<211> LENGTH: 19
<212> TYPE: RNA
<213> ORGANISM: Artificial Sequence
<220> FEATURE:
<223> OTHER INFORMATION: synthetic sequence

<400> SEQUENCE: 6

ucaaggaagg cuauagcag                                               19


<210> SEQ ID NO 7
<211> LENGTH: 19
<212> TYPE: RNA
<213> ORGANISM: Artificial Sequence
<220> FEATURE:
<223> OTHER INFORMATION: synthetic sequence

<400> SEQUENCE: 7

gugauggcuu uuaccuacu                                               19


<210> SEQ ID NO 8
<211> LENGTH: 19
<212> TYPE: RNA
<213> ORGANISM: Artificial Sequence
<220> FEATURE:
<223> OTHER INFORMATION: synthetic sequence

<400> SEQUENCE: 8

aguagguaaa agccaucac                                               19
```